(12) United States Patent
Casarez et al.

(10) Patent No.: US 10,065,957 B2
(45) Date of Patent: Sep. 4, 2018

(54) BETA-LACTAMASE INHIBITORS

(71) Applicant: Novartis AG, Basel (CH)

(72) Inventors: Anthony Casarez, San Francisco, CA (US); Markus Furegati, Allschwil (CH); Guido Koch, Bettingen (CH); Xiaodong Lin, Orinda, CA (US); Flavio Ossola, Liestal (CH); Folkert Reck, Walnut Creek, CA (US); Robert Lowell Simmons, San Francisco, CA (US); Qingming Zhu, Walnut Creek, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/718,571

(22) Filed: Sep. 28, 2017

(65) Prior Publication Data
US 2018/0086762 A1 Mar. 29, 2018

Related U.S. Application Data

(60) Provisional application No. 62/401,022, filed on Sep. 28, 2016.

(51) Int. Cl.
| | | |
|---|---|---|
| *C07D 471/18* | (2006.01) | |
| *A61K 31/439* | (2006.01) | |
| *A61K 31/5025* | (2006.01) | |
| *A61K 31/407* | (2006.01) | |
| *A61K 31/427* | (2006.01) | |
| *A61K 31/431* | (2006.01) | |
| *A61K 31/496* | (2006.01) | |
| *A61K 31/546* | (2006.01) | |
| *A61K 31/535* | (2006.01) | |
| *A61P 31/04* | (2006.01) | |

(52) U.S. Cl.
CPC .......... *C07D 471/18* (2013.01); *A61K 31/407* (2013.01); *A61K 31/427* (2013.01); *A61K 31/431* (2013.01); *A61K 31/439* (2013.01); *A61K 31/496* (2013.01); *A61K 31/5025* (2013.01); *A61K 31/535* (2013.01); *A61K 31/546* (2013.01); *A61P 31/04* (2018.01); *C07B 2200/13* (2013.01)

(58) Field of Classification Search
CPC . C07D 471/18; A61K 31/439; A61K 31/5025
See application file for complete search history.

(56) References Cited

U.S. PATENT DOCUMENTS

| | | | |
|---|---|---|---|
| 7,288,549 | B2 | 10/2007 | Aszodi |
| 7,439,253 | B2 | 10/2008 | Lampilas |
| 8,148,540 | B2 | 4/2012 | Aszodi |
| 2003/0199541 | A1 | 10/2003 | Lampilas |
| 2004/0157826 | A1 | 8/2004 | Lampilas |
| 2005/0245505 | A1 | 11/2005 | Aszodi |
| 2007/0299108 | A1 | 12/2007 | Aszodi |
| 2009/0018329 | A1 | 1/2009 | Lampilas |
| 2010/0092443 | A1 | 4/2010 | Levasseur |
| 2013/0225554 | A1 | 8/2013 | Maiti |

FOREIGN PATENT DOCUMENTS

| | | |
|---|---|---|
| EP | 1 798 231 | 6/2007 |
| WO | WO 2002/100860 | 12/2002 |
| WO | WO 2004/052891 | 6/2004 |
| WO | WO 2008/039420 | 4/2008 |
| WO | WO 2009/091856 | 7/2009 |
| WO | WO 2010/126820 | 11/2010 |
| WO | WO 2013/038330 | 3/2013 |
| WO | WO 2013/122888 | 8/2013 |
| WO | WO 2013/149121 | 10/2013 |
| WO | WO 2013/149136 | 10/2013 |
| WO | WO 2014/033560 | 3/2014 |
| WO | WO 2014/141132 | 9/2014 |

OTHER PUBLICATIONS

Bonnefoy et al., "In vitro Activity of AVE1330A, an Innovative Broad-Spectrum non-β-Lactam β-Lactamase Inhibitor" *J. Antimicrobial Chemotherapy* 54(2):410-417, Jan. 2004.
Tranquillini et al., "Synthesis and Antimicrobial Activity of 4-Amino Trinems" *Biorganic & Medicinal Chemistry Letters* 6(14):1683-1688, Jul. 1996.
Asli et al., "Distinctive Binding of Avibactam to Penicillin-Binding Proteins of Gram-Negative and Gram-Positive Bacteria" *Antimicrobial Agents and Chemotherapy* 60(2):752-756, 2016.
K. Bush, "A Resurgence of β-lactamase Inhibitor Combinations Effective Against Multidrug-Resistant Gram-Negative Pathogens" *Int. J. Antimicrob. Agents* 46(5):483-493, 2015.
Chu et al., "Carboxylic Acids as a Traceless Activation Group for Conjugate Additions: a Three-Step Synthesis of (±)-Pregabalin" *J. Am. Chem. Society* 136(31):10886-10889, 2014.
Doumith et al., "New Insights into the Regulatory Pathways Associated with the Activation of the Stringent Response in Bacterial Resistance to the PBP2-Targeted Antibiotics, Mecillinam and OP0595/RG6080" *J. Antimicrobial Chemotherapy* 71:2810-2814, 2016.

*Primary Examiner* — Rebecca L Anderson
*Assistant Examiner* — Karen Cheng
(74) *Attorney, Agent, or Firm* — Mark H. Hopkins

(57) ABSTRACT

This invention pertains generally to compounds of Formula (A),

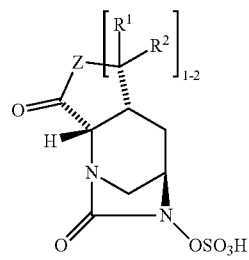

as further described herein, which act as beta-lactamase inhibitors, and salts, crystalline forms and formulations thereof. In certain aspects, the invention pertains to methods of using such compounds in combination with a beta-lactam antibiotic to treat infections caused by Gram-negative bacteria, including drug-resistant strains.

18 Claims, 3 Drawing Sheets

Specification includes a Sequence Listing.

Scanning Electron Microscope image of Crystalline form of Compound of Formula (VII).

BETA-LACTAMASE INHIBITORS

CROSS-REFERENCE TO RELATED APPLICATION

This application claims the benefit of priority to U.S. Provisional Application No. 62/401,022, filed 28 Sep. 2016, the content of which is incorporated herein by reference.

FIELD OF THE INVENTION

This invention relates to compounds that inhibit beta-lactamases, methods to make these compounds, and their use in combination with beta-lactam antibiotics for treatment of bacterial infections.

BACKGROUND

Over the past several decades, the frequency of antimicrobial resistance and its association with serious infectious diseases have increased at alarming rates. The increasing prevalence of resistance among nosocomial pathogens is particularly disconcerting. Of the over 2 million nosocomial infections occurring each year in the United States, 50 to 60% are caused by antimicrobial-resistant strains of bacteria. The high rate of resistance to commonly used antibacterial agents increases the morbidity, mortality, and costs associated with nosocomial infections. In the United States, nosocomial infections are thought to contribute to or cause more than 77,000 deaths per year and cost approximately $5 to $10 billion annually.

Among the most important antibiotics currently available are several classes of compounds that contain a beta-lactam ring, including penicillins, penems, carbapenems, cephalosporins, monobactams and sulfactams. These beta-lactam antibiotics inhibit cell wall biosynthesis by binding to proteins called penicillin-binding proteins (PBPs), which are essential for synthesis of peptidoglycan, the major component of the cell wall of Gram-negative and Gram-positive bacteria. While beta-lactam antibiotics remain extremely important worldwide, their extensive use has led to a large and growing problem: bacteria have developed resistance to beta-lactams, just as they have to most other available antibiotics. Indeed, the World Health Organization (WHO) says antibiotic resistance is a "serious, worldwide threat . . . ."

Several different mechanisms of resistance to beta-lactam antibiotics have been identified: some resistant strains possess efflux pumps to excrete antibiotic, and others develop mutant PBPs that are less sensitive to the antibiotic. An especially troubling form of resistance is development of bacterial enzymes that react with these antibiotics, destroying the antibiotic by opening the beta-lactam ring. These antibiotic-degrading enzymes are called beta-lactamases, and are particularly problematic because they can impart resistance to many different beta-lactam antibiotics, and they can be transferred via plasmids between different bacterial strains and species. Among Gram-negative bacteria, there are four classes of beta-lactamases, the serine beta-lactamases of the classes A, C and D, and the metallo beta-lactamases (class B).

Important causes of resistance to beta-lactam antibiotics include extended-spectrum beta-lactamases (ESBLs), serine carbapenemases of the class A, (e.g. KPC-2) and of class D (e.g. OXA-48) in *Klebsiella pneumoniae, Escherichia coli,* and *Proteus mirabilis,* as well as high-level resistance against third-generation cephalosporins mediated by the class C beta-lactamase AmpC among *Enterobacter* species and *Citrobacter freundii,* and multidrug-resistance strains of *Pseudomonas, Acinetobacter,* and *Stenotrophomonas.* The problem of antibacterial resistance is compounded by the existence of bacterial strains containing multiple beta-lactamases. For example, *Klebsiella pneumonia* harboring NDM-1 metallo-beta-lactamase frequently carries additional serine-beta-lactamases on the same plasmid that carries the NDM-1.

Since beta-lactam antibiotics are among the few classes that are effective against Gram-negative bacteria, many efforts have been made to bolster their ability to control resistant bacterial strains, in order to avoid losing these enormously valuable antibacterials. For example, some beta-lactams have been modified structurally to make them less susceptible to beta-lactamases, although this approach is complicated by the fact that there are already many different beta-lactamases, and new ones arise constantly. Another approach has been to inhibit the beta-lactamase enzymes that degrade these antibiotics by using a small-molecule beta-lactamase inhibitor (BLI) in combination with a beta-lactam antibiotic. These BLIs can be used in combination with an approved beta-lactam antibiotic to treat patients infected with bacteria that are resistant to the antibiotic alone due to beta-lactamase activity. Examples of approved BLIs include clavulanic acid, sulbactam, tazobactam, and avibactam. Others (relebactam, vaborbactam (RPX7009), zidebactam, and nacubactam) are reportedly in development.

In Gram-positive organisms, penicillin resistance mediated by penicillinase-type beta-lactamases is an important mechanism of resistance in *Staphylococcus aureus* (MSSA). Beta-lactamase-mediate resistance to penicillins is also found in anaerobic species, like bacteroides.

The three most commonly used serine beta-lactamase inhibitors, clavulanic acid, tazobactam and sulbactam, have potent activity only against some class A beta-lactamases, excluding serine carbapenemases. Avibactam is a member of the diazabicyclooctane (DBO) class of beta-lactamase inhibitors and has a broad coverage of class A (including KPCs), class C and some inhibition of class D. Along with beta-lactamase inhibition, avibactam also has antibacterial activity against some clinical strains through inhibiting penicillin binding protein 2 (PBP-2) (Asli et al, *Antimicrobial Agents and Chemotherapy,* 60, No 2, 752, 2016). Antibacterial compounds with this mechanism of action, including DBOs, select for resistance at very high frequencies in vitro (Doumith et al, *J. Antimicrobial Chemotherapy* 2016, 71, 2810-2814). Because of this, any potential clinical benefit of the intrinsic antibacterial activity of some DBO beta-lactamase inhibitors is currently unclear. The weak antibacterial activity of avibactam may not be clinically relevant, since the clinical dose of avibactam is fairly low, however, it may complicate in vitro susceptibility testing and/or promote resistance. In vitro susceptibility testing of avibactam/beta-lactam combinations against clinical isolates is typically conducted using a high fixed concentration of avibactam (4 µg/mL) that likely does not reflect the clinically achieved levels. The direct contribution of avibactam to antibacterial activity under these artificial in vitro testing conditions could affect the accuracy in predicting clinical efficacy of avibactam/beta-lactamase combinations. A DBO beta-lactamase inhibitor devoid of significant antibacterial activity would not have this extra confounding activity, and in vitro testing protocols would measure only the reversal of beta-lactamase mediated resistance in clinical isolates, enabling a more accurate prediction of clinical efficacy based on in vitro susceptibility results.

In addition to BLIs currently available for use, other compounds with BLI activity are disclosed in WO2002/100860, US2003/0199541, US2004/0157826, WO2008/039420, and WO2009/091856, US2010092443, WO2010/126820, WO2013/122888, WO2013/038330, US2013/0225554, WO2013149121, WO2013149136, WO2014141132 and WO2014/033560.

The pharmacokinetic and physical properties of previously described BLIs may not be ideal for use with every beta-lactam antibiotic. Moreover, known BLIs are reportedly losing effectiveness over time (K. Bush, *Int. J. Antimicrob. Agents* 46(5), 483-93 (November 2015)), as resistant bacterial strains develop and new beta-lactamase enzymes arise continually. Accordingly, there remains a need for new beta-lactamase inhibitors to extend the usefulness of valuable beta-lactam antibiotics; indeed, novel BLIs may also combat resistance to known BLIs as well as resistance to known and future-developed beta-lactam antibiotics. The present invention provides novel beta-lactamase inhibitors that potentiate the activity of various beta-lactam antibiotics, while they exhibit little intrinsic (direct) antibiotic activity of their own.

SUMMARY

The invention includes novel BLI compounds, pharmaceutical combinations and formulations including these compounds, and methods of using such compounds and compositions for treatment of patients with bacterial infections. The BLIs are used in combination with a beta-lactam antibiotic, e.g. a penicillin derivatives, penem, carbapenem, cephalosporin (cephem), monobactam or sulfactam, and are primarily useful for treatment of Gram-negative bacterial infections, but also are useful for the treatment of Gram-positive and anaerobic infections, where resistance is mediated through production of a beta-lactamase by the bacterium. The invention includes compounds of Formula (A) and variants thereof,

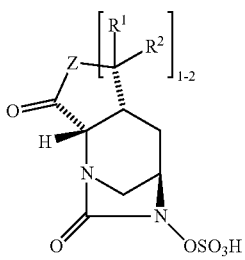

(A)

and the salts of these compounds, including compounds of Formula (I):

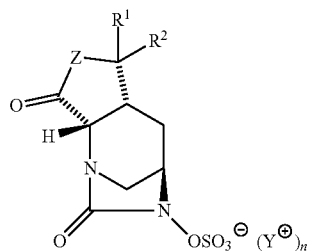

(I)

wherein compounds of Formula (I) may be in a salt or zwitterionic form, as further described herein.

The BLI compounds of the invention are used in combination with a beta-lactam antibiotic, examples of which are disclosed herein, to treat bacterial infections, especially Gram-negative bacterial infections. The BLI and beta-lactam antibiotic can be administered together or separately, and the BLI enhances the effectiveness of the beta-lactam antibiotic against at least on bacterial strains that exhibit resistance to beta-lactam antibiotics, where the resistance is mediated by a beta-lactamase activity. The combinations of beta-lactam antibiotic and BLI of Formula (A) can be used to treat infections caused by Gram-negative bacteria, including Enterobacteriaceae, such as *Salmonella, E. coli, Klebsiella pneumoniae, Proteus, Enterobacter, Serratia*, and *Citrobacter*, non-fermenting bacteria, including *Pseudomonas aeruginosa, Acinetobacter, Burkholderia, Moraxella* and *Stenotrophomonas*, Gram-positive bacteria, such as beta-lactamase producing *Staphylococcus aureus*, as well as anaerobic bacteria, such as *Bacteroides fragilis* or *Bacteroides thetaiotaomicron*.

In one aspect, the invention provides novel compounds of Formula (A) and Formula (I), including their salt or zwitterionic forms, which are effective as inhibitors of one or more bacterial beta-lactamases. The compounds are useful to potentiate the antibacterial activity of a beta-lactam antibiotic. They may thus be used in combination with a beta-lactam antibiotic. The BLI and beta-lactam antibiotic may be administered together or separately; in some embodiments, a BLI of Formula (A) or Formula (I) and a beta-lactam antibiotic are combined in a pharmaceutical composition that typically also comprises at least one pharmaceutically acceptable carrier.

In one aspect, the invention provides methods to make compounds of Formula (A) or Formula (I) and novel precursors useful to make compounds of Formula (A) or Formula (I) as described herein. In particular, the invention provides a process to convert a compound of Formula (V) into a compound of Formula (IV); and a method to convert a compound of Formula (III) into compounds of Formula (I).

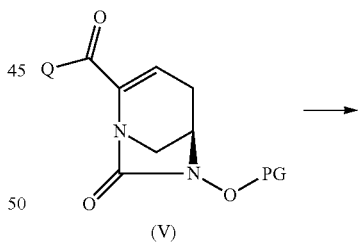

(V)

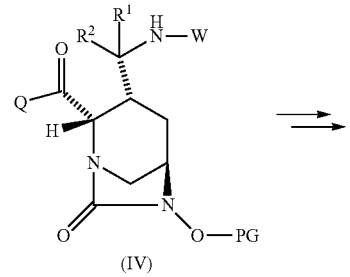

(IV)

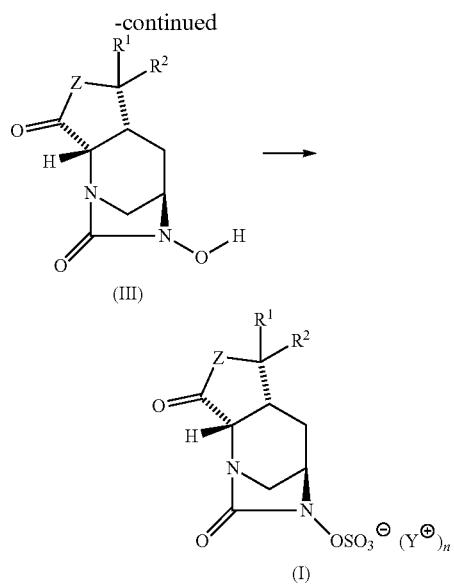

In another aspect, the invention provides pharmaceutical compositions comprising a compound of Formula (A) and Formula (I) admixed with at least one pharmaceutically acceptable carrier or excipient. In some embodiments, the composition comprises two or more such carriers or excipients. Optionally, the pharmaceutical composition further includes a beta-lactam antibiotic, although the BLI compound can be formulated and administered separately from the beta-lactam antibiotic.

In another aspect, the invention provides a method for treating a subject having a bacterial infection, which comprises administering to the subject in need thereof an antibacterially effective amount of a beta-lactam antibiotic and an effective amount of a BLI of Formula (A) or Formula (I), including salt and zwitterionic forms, optionally in combination with a pharmaceutically acceptable carrier. In certain embodiments, the subject is a mammal and in some embodiments, the subject is a human. This aspect provides a compound of Formula (A) or Formula (I), including pharmaceutically acceptable salt or zwitterionic forms, for use to treat a bacterial infection, where the compound is used in combination with a beta-lactam antibiotic. It also includes use of a compound of Formula (A) or Formula (I), or a salt or zwitterionic form thereof, in the manufacture of a medicament. Preferably, the medicament is one for use to treat a Gram-negative bacterial infection, especially one having a beta-lactamase activity sufficient to impart some level of resistance to the beta-lactam antibiotic, where the medicament is adapted for use in combination with a beta-lactam antibiotic such as those described herein. The beta-lactam antibiotic and BLI compound of Formula (A) or Formula (I) may be administered simultaneously or separately and in any order, provided the BLI is present in vivo concurrently with the beta-lactam antibiotic in order to potentiate the effectiveness of the beta-lactam antibiotic.

The Gram-negative bacteria may be of a genus selected from *Citrobacter, Enterobacter, Escherichia, Klebsiella, Morganella, Proteus, Salmonella, Serratia, Pseudomonas, Acinetobacter, Bacteroides, Burkholderia, Campylobacter, Neisseria*, and *Stenotrophomonas*. In particular, a bacterial infection caused by a species of *Citrobacter, Enterobacter, Escherichia, Klebsiella, Morganella, Proteus, Salmonella, Serratia, Pseudomonas*, or *Acinetobacter* is treatable by the methods disclosed herein. Particular bacterial species for such treatment include *Citrobacter freundii, Citrobacter koseri, Enterobacter cloacae, Enterobacter aerogenes, Escherichia coli, Klebsiella pneumoniae, Klebsiella oxytoca, Morganella morganii, Proteus mirabilis, Salmonella* species, *Serratia marcescens, Pseudomonas aeruginosa*, and *Acinetobacter baumannii*, as well as *Bacteroides fragilis, Burkholderia cepacia, Campylobacter jejuni, Neisseria gonorrhoeae*, and *Stenotrophomonas maltophilia*. The Gram-positive bacteria may be, for example, *Enterococcus faecalis, Enterococcus faecium, Staphylococcus aureus* or *Streptococcus pneumoniae*.

In another aspect, the invention provides a method of inhibiting bacterial growth or modulating the virulence of a bacterial infection, wherein the method comprises administering to a patient in need of such inhibition a compound of Formula (A) or Formula (I) and a beta-lactam antibiotic. Suitable beta-lactam antibiotics for use in these methods are described herein.

Pharmaceutical compositions according to the present invention are provided which include any of the compounds described herein and a pharmaceutically acceptable carrier. In some embodiments the composition includes an additional therapeutic agent such as a beta-lactam antibiotic.

Other aspects of the invention are discussed herein.

DETAILED DESCRIPTION

Figure 1:
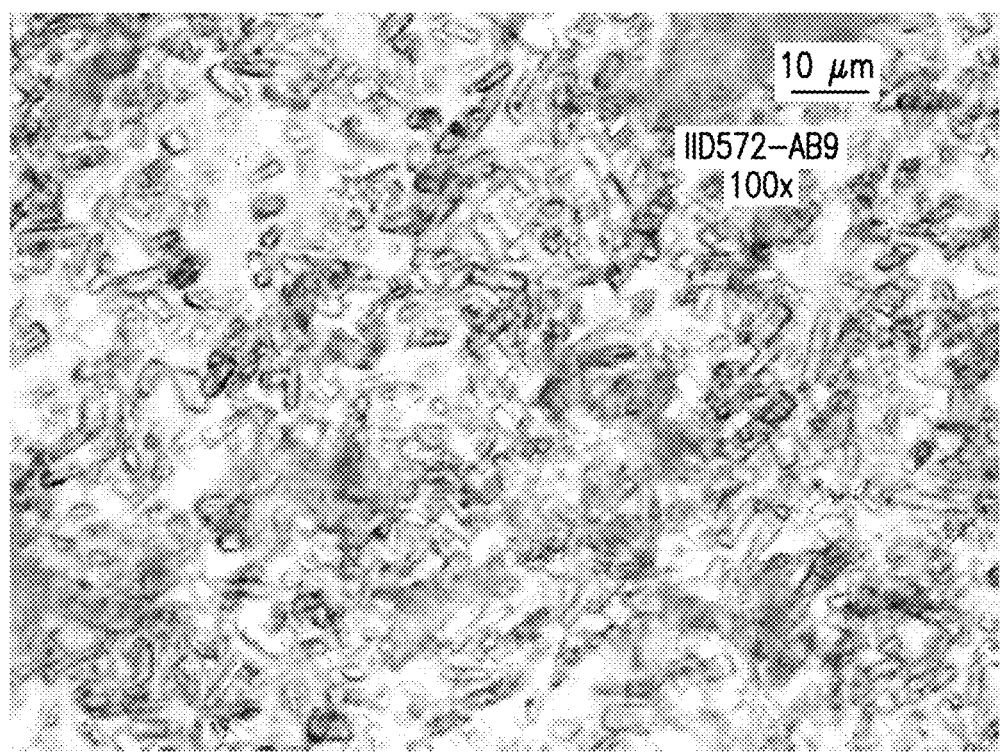
FIG. 1. SEM of Crystalline Compound of Formula (VII).
Figure 2:
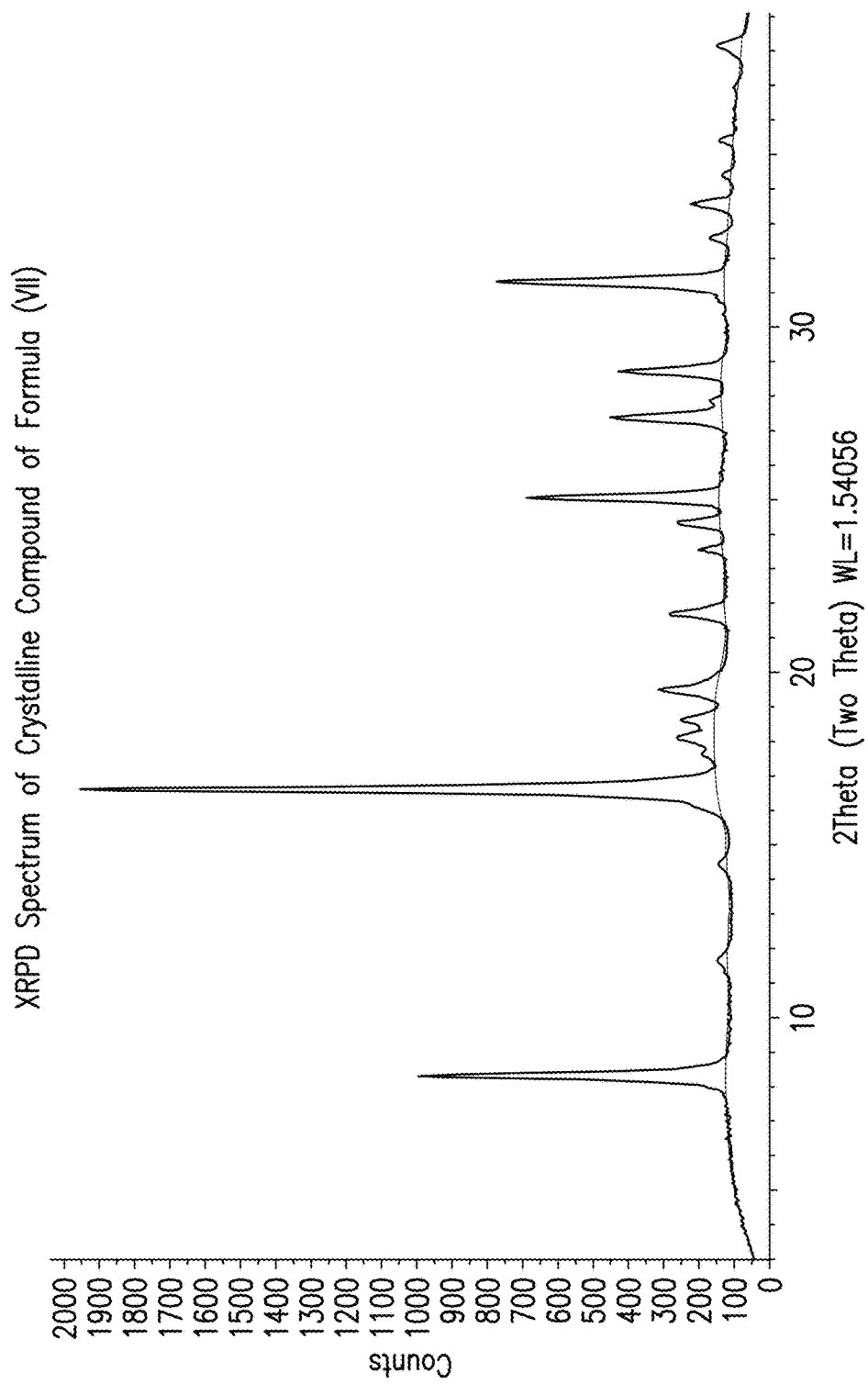
FIG. 2. XRPD of Crystalline Compound of Formula (VII).
Figure 3:
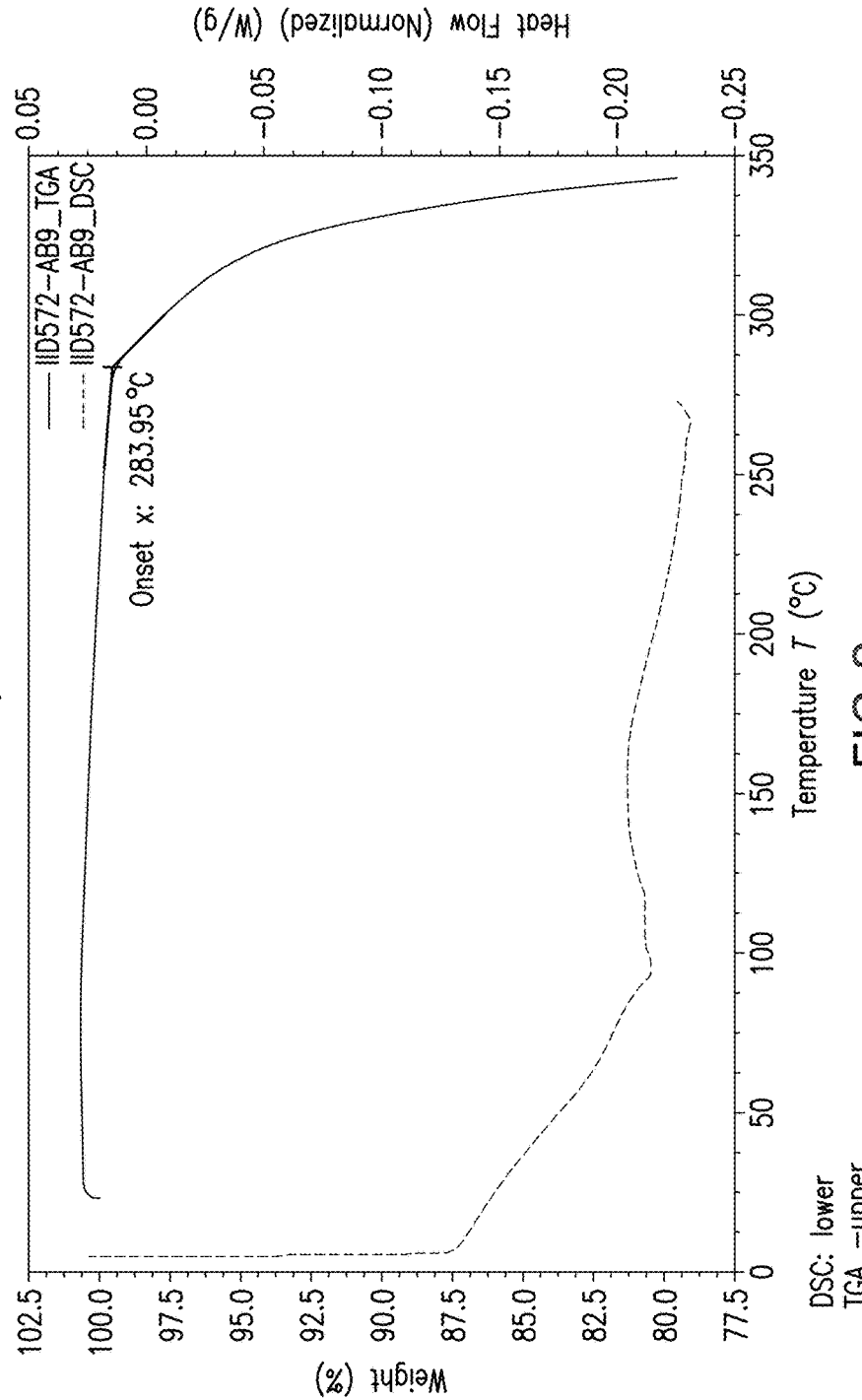
FIG. 3. Thermogravimetric Analysis and Differential Scanning Calorimetry Analysis of Crystalline Compound of Formula (VII).

For purposes of interpreting this specification, the following definitions apply unless specified otherwise or clearly contradicted by context. Whenever appropriate, terms used in the singular will also include the plural and vice versa.

Definitions

Terms used in the specification have the following meanings:

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human.

As used herein, the term "inhibition" or "inhibiting" refers to the reduction or suppression of a given condition, symptom, or disorder, or disease, or a significant decrease in the baseline activity of a biological activity or process, or decrease in the viability, number or growth rate of a bacterial population.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The term "antibacterial agent" refers to agents synthesized or modified in the laboratory that have either bactericidal or bacteriostatic activity. An "active" agent in this context will inhibit the growth of *P. aeruginosa* and/or other Gram-negative bacteria. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated.

The term "beta-lactam antibiotic" refers to an antibacterial agent that contains a 4-membered lactam ring, also referred to as a beta-lactam, that possesses antibacterial activity. Classes of beta-lactam antibiotics include penicillins, cephalosporins, monobactams, carbapenems, oxapenems, cephems, carbacephems, oxacephems, penems, penams, sulbactams and clavams. Particular beta-lactam antibiotics suitable for use in the methods and compositions of the invention are described herein, and include aztreonam, piperacillin, ceftazidime, meropenem, and beta-lactam 5.

The term 'beta-lactamase" as used herein refers to an enzymatic activity possessed or exhibited by a bacterium, which catalyzes the degradation or inactivation of a beta-lactam antibiotic. Typically, it catalyzes hydrolysis of the beta-lactam ring of a monocyclic or bicyclic beta-lactam antibiotic, and is expressed in a Gram-negative or Gram-positive bacterium that can cause infection in mammalian subjects, especially humans. Beta-lactamases of interest include Class A (including extended spectrum beta-lactamases and serine carbapenemases), as well as Class C and D beta-lactamases.

The term "beta-lactamase inhibitor" or "BLI" as used herein refers to a compound that inhibits at least one bacterial beta-lactamase. This means it inhibits at least one member of the classes of serine beta-lactamases, e.g. a Class A, C or D beta-lactamase. By reducing beta-lactamase activity, these compounds enhance the activity of a beta-lactam antibiotic used in combination with the BLI; this effect is referred to herein as potentiation, since the BLI does not have significant antibacterial activity of its own but boosts or potentiates the antibacterial activity of the antibiotic in bacteria that possess beta-lactamase activity. Potentiation results from the fact that the BLI allows the beta-lactam antibiotic to persist longer in vivo within the bacterial periplasmic compartment or in the vicinity of the bacterial pathogens, making the antibiotic more effective, or making it effective at a lower dosage than would be required in the absence of the BLI of Formula (A). Preferably, a BLI is effective at a 50% inhibitory concentration below about 100 µg/mL (micrograms/mL), or below about 50 µg/mL, or below about 25 µg/mL.

Suitable beta-lactam antibiotics for use in combination with the BLIs of the invention include, for example, aztreonam, imipenem, ertapenem, meropenem, doripenem, biapenem, piperacillin, ceftriaxone, cefoperazone, cefotaxime, ceftazidime, ceftolozane, cefepime, panipenem, ticarcillin, ampicillin, amoxicillin, carbenicillin, azlocillin, mezlocillin, ticarcillin, cefoperazone, beta-lactam 5 (shown herein), and the like.

"Optionally substituted" means the group referred to can be substituted at one or more positions by any one or any combination of the radicals listed thereafter. Such substitution involves the replacement of a hydrogen atom of the unsubstituted group with another moiety; thus the number of substituents that can be added to any unsubstituted group is equal to the number of hydrogen atoms on the unsubstituted group. If not otherwise specified, 'optionally substituted' means that up to three non-hydrogen substituent groups can be present.

"Halo" or "halogen", as used herein, may be fluorine, chlorine, bromine or iodine.

"$C_1$-$C_6$ alkyl", or "$C_{1-6}$ alkyl" as used herein, denotes straight chain or branched alkyl having 1-6 carbon atoms. If a different number of carbon atoms is specified, such as $C_8$ or $C_3$, then the definition is to be interpreted accordingly, such as "$C_1$-$C_4$ alkyl" will include methyl, ethyl, propyl, isopropyl, butyl, isobutyl, sec-butyl and tert-butyl.

"$C_1$-$C_6$ alkoxy", or "$C_{1-6}$ alkoxy" as used herein, denotes straight chain or branched alkoxy having 1-6 carbon atoms. If a different number of carbon atoms is specified, such as $C_8$ or $C_3$, then the definition is to be interpreted accordingly, e.g., "$C_1$-$C_4$ alkoxy" will represent methoxy, ethoxy, propoxy, isopropoxy, butoxy, isobutoxy, sec-butoxy and tert-butoxy.

"$C_1$-$C_4$-Haloalkyl" or "$C_{1-4}$ haloalkyl" as used herein, denotes straight chain or branched alkyl having 1-4 carbon atoms, wherein at least one hydrogen has been replaced by a halogen. If a different number of carbon atoms is specified, such as $C_6$ or $C_3$, then the definition is to be interpreted accordingly, thus "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CHCF_3$ or $CF_3CF_2CF_2CF_2$—.

"$C_3$-$C_8$-cycloalkyl" or "$C_{3-8}$ cycloalkyl" as used herein refers to a saturated monocyclic hydrocarbon ring of 3 to 8 carbon atoms. Examples of such groups include cyclopropyl, cyclobutyl, cyclopentyl and cyclohexyl. If a different number of carbon atoms is specified, such as $C_3$-$C_6$, then the definition is to be interpreted accordingly.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refer, respectively, to 4- to 8-membered, 5- to 6-membered, 3- to 10-membered, 3- to 14-membered, 4- to 14-membered and 5- to 14-membered heterocyclic rings containing 1 to 7, 1 to 5 or 1 to 4 heteroatoms selected from the group consisting of nitrogen, oxygen and sulphur, which may be saturated, or partially saturated. "Heterocyclic" may be used interchangeably with "heterocyclyl". The heterocyclic group can be attached at a heteroatom or a carbon atom. The term "heterocyclyl" includes single ring groups, fused ring groups and bridged groups. Examples of such heterocyclyl include, but are not limited to pyrrolidine, piperidine, piperazine, oxazolidine, pyrrolidinone, morpholine, tetrahydrofuran, tetrahydrothiophene, tetrahydrothiopyran, tetrahydropyran, 1,4-dioxane, 1,4-oxathiane, 8-aza-bicyclo[3.2.1]octane, 3,8-diazabicyclo[3.2.1]octane, 3-Oxa-8-aza-bicyclo[3.2.1]octane, 8-Oxa-3-aza-bicyclo[3.2.1]octane, 2-Oxa-5-aza-bicyclo[2.2.1]heptane, 2,5-Diaza-bicyclo[2.2.1]heptane, azetidine, ethylenedioxo, oxetane and thiazolidine. Preferably, a heterocyclic or heterocyclyl group is a saturated or partially saturated monocyclic group unless otherwise specified, and contains 5-7 ring atoms with up to two heteroatoms selected from N, O and S as ring members. In some embodiments, a heterocyclic group further includes bicyclic ring systems containing 1 or 2 heteroatoms such as N, O or S as ring members and comprising two fused 3-, 4-, 5-, or 6-membered rings, such as 3-azabicyclo[3.1.0]hexane, 8-aza-bicyclo[3.2.1]octane, 3,8-diazabicyclo[3.2.1]octane, 3-Oxa-8-aza-bicyclo[3.2.1]octane, 8-Oxa-3-aza-bicyclo[3.2.1]octane, 2-Oxa-5-aza-bicyclo[2.2.1]heptane, 2,5-Di-aza-bicyclo[2.2.1]heptane.

"Heteroaryl" is a completely unsaturated (aromatic) ring. The term "heteroaryl" refers to a 5-14 membered monocyclic- or bicyclic- or tricyclic-aromatic ring system, having 1 to 8 heteroatoms selected from N, O and S. Typically, the heteroaryl is a 5-10 membered ring system (e.g., 5-6 membered monocycle or an 8-10 membered bicycle) or a 5-6 membered ring system. Unless otherwise specified, a heteroaryl is preferably an isolated 5-6 membered ring containing up to 4 heteroatoms selected from N, O and S as ring members. Typical heteroaryl groups include furan, isothiazole, thiadiazole, oxadiazole, indazole, indole, quinoline, 2- or 3-thienyl; 2- or 3-furyl; 2- or 3-pyrrolyl; 1-, 2-, 4-, or 5-imidazolyl; 1, 3-, 4-, or 5-pyrazolyl; 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-(1,2,3-triazolyl), tetrazolyl, triazine, pyrimidine, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "hydroxy" or "hydroxyl" refers to the group —OH, or when used as part of a group name such as hydroxyalkyl, it refers to the named group substituted with an —OH.

A "zwitterion" is a molecule that has both positively-charged and negatively-charged groups but has no overall charge i.e. the + and − charges are balanced within the molecule. To convert an anionic molecule into a neutral molecule then anions would typically be replaced by neutral groups, but to convert an anionic molecule into a zwitterion then a neutral group is replaced by a cationic group.

Compounds of formula (A) exist in free form, as a salt or as zwitterion. In this specification, unless otherwise indicated, language such as "compounds of formula (A)" is to be understood as embracing the compounds in any form, for example free base or acid addition or exchange salt form. Salts which may be unsuitable for pharmaceutical uses but which can be employed, for example, for the isolation or purification of free compounds of formula (A), such as picrates or perchlorates, are also included. For therapeutic use, only pharmaceutically acceptable salts, zwitterions or free compounds are employed (where applicable in the form of pharmaceutical preparations), and are therefore preferred. Salts are preferably physiologically acceptable salts, formed, as applicable, by the addition of an acid or base or by ion exchange.

Compounds of formula (A) may exist in the form of various zwitterions. For example, the compounds of formula (A) may show protonated amino-groups and deprotonated sulfate-groups. In this specification, the drawing of the compound in the free form includes other possible zwitterions as well. The zwitterions of the compounds of formula (A) are also embraced by the invention.

The compounds of formula (A) may exist in optically active form or in form of mixtures of optical isomers, e.g. in form of racemic mixtures or diastereomeric mixtures. In particular, asymmetrical carbon atom(s) may be present in the compounds of formula (A) and their salts. All optical isomers and their mixtures, including the racemic mixtures, are embraced by the invention. Various embodiments of the invention are described herein. It will be recognized that features specified in each embodiment may be combined with other specified features to provide further embodiments. The following numbered embodiments are representative of additional aspects of the invention.

In one embodiment, the invention provides compounds of Formula (A):

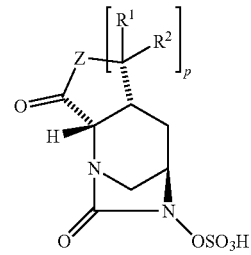

wherein p is 1 or 2;

$R^1$ and $R^2$ are independently selected from H and $C_1$-$C_4$ alkyl optionally substituted with up to three groups selected from halo, CN, —OR, oxo, and —NRR';

Z is $NR^3$ or N—$OR^3$;

$R^3$ is independently selected at each occurrence from H, Cy, and $C_1$-$C_4$ alkyl optionally substituted with up to three groups selected from Cy, halo, CN, —OR, and —NRR';

Cy is a $C_3$-$C_6$ cycloalkyl ring or 4-6 membered heterocyclic ring containing one or two heteroatoms selected from N, O and S as ring members, and Cy is optionally substituted with up to three groups selected from oxo, halo, $C_1$-$C_2$ alkyl, CN, —OR, and —NRR'; and R and R' are independently selected from H and $C_1$-$C_4$ alkyl optionally substituted with one or two groups selected from halo, —OH, —CN, —O—($C_1$-$C_4$ alkyl), oxo, —$NH_2$, —NH($C_1$-$C_4$ alkyl), and —N($C_1$-$C_4$ alkyl)$_2$, or R and R' taken together with the nitrogen atom to which both are attached can form a ring selected from piperidine, morpholine, pyrrolidine, and azetidine, wherein the ring is optionally substituted with one or two groups selected from halo, $C_1$-$C_2$ alkyl, —OH, —CN, —O—($C_1$-$C_4$ alkyl), oxo, —$NH_2$, —NH($C_1$-$C_4$ alkyl), and —N($C_1$-$C_4$ alkyl)$_2$;

or a salt or zwitterionic form thereof.

Particular embodiments of these compounds include compounds the following formulas:

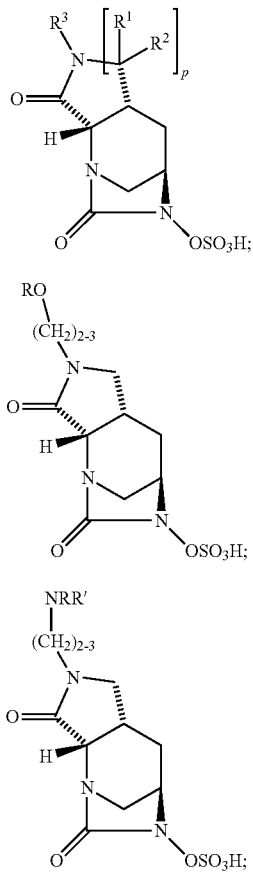

(A-1)

(A-2a)

(A-2b)

or or a salt or zwitterionic form thereof.

An embodiment of special interest is compound of Formula (I):

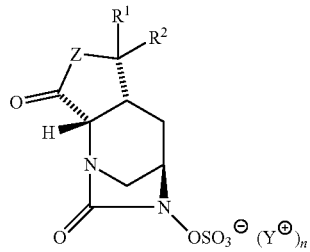

(I)

wherein:

R¹ and R² are independently selected from H and $C_1$-$C_4$ alkyl optionally substituted with up to three groups selected from halo, CN, —OR, oxo, and —NRR';

Z is $NR^3$ or N—$OR^3$;

$R^3$ is independently selected at each occurrence from H, Cy, and $C_1$-$C_4$ alkyl optionally substituted with up to three groups selected from Cy, halo, CN, —OR, and —NRR';

Cy is a $C_3$-$C_6$ cycloalkyl ring, or 4-6 membered heterocyclic ring containing one or two heteroatoms selected from N, O and S as ring members, and Cy is optionally substituted with up to three groups selected from oxo, halo, $C_1$-$C_2$ alkyl, CN, —OR, and —NRR'; and R and R' are independently selected from H and $C_1$-$C_4$ alkyl optionally substituted with one or two groups selected from halo, —OH, —CN, —O—($C_1$-$C_4$ alkyl), oxo, —$NH_2$, —NH($C_1$-$C_4$ alkyl), and —N($C_1$-$C_4$ alkyl)$_2$, or R and R' taken together with the nitrogen atom to which both are attached can form a ring selected from piperidine, morpholine, pyrrolidine, and azetidine, wherein the ring is optionally substituted with one or two groups selected from halo, $C_1$-$C_2$ alkyl, —OH, —CN, —O—($C_1$-$C_4$ alkyl), oxo, —$NH_2$, —NH($C_1$-$C_4$ alkyl), and —N($C_1$-$C_4$ alkyl)$_2$;

Y is a cationic group;

n is 0 or 1; and when n is 0 the compound of Formula I is in a zwitterionic form.

Each of the compounds of the Examples herein is a specific embodiment of the invention.

The compound of any of the preceding embodiments, wherein Z is $NR^3$, and $R^3$ is H or $C_1$-$C_4$ alkyl optionally substituted with —OR or —NRR', or a salt or zwitterionic form thereof.

The compound of embodiment 4, wherein $R^3$ is $C_1$-$C_2$ alkyl optionally substituted with —OR or —NRR', or a salt or zwitterionic form thereof.

The compound of embodiment 4, wherein $R^3$ is H, or a salt or zwitterionic form thereof.

The compound of any one of embodiments 1-6, wherein $R^1$ and $R^2$ are both H, or a salt or zwitterionic form thereof.

The compound of embodiment 1, which has this structure:

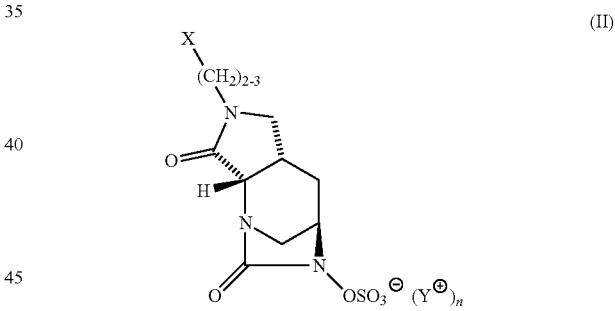

(II)

wherein X is —OR or —NRR';

Y is a cationic group;

n is 0 or 1; and when n is 0 the compound of Formula II is in a zwitterionic form.

The compound of embodiment 1, which is selected from:

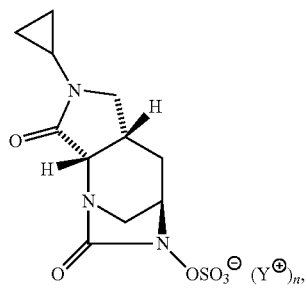

-continued

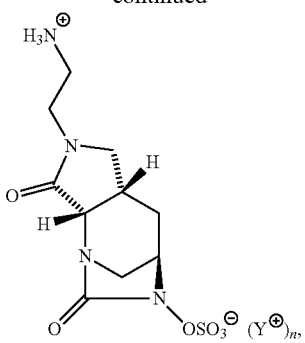

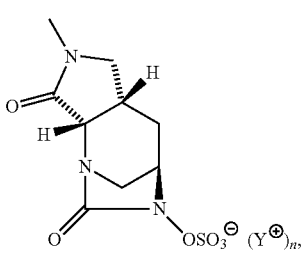

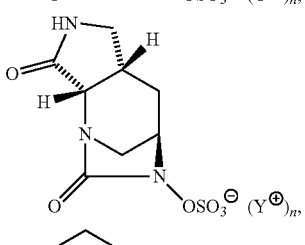

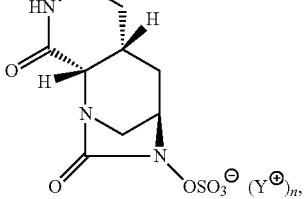

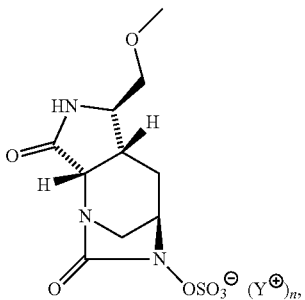

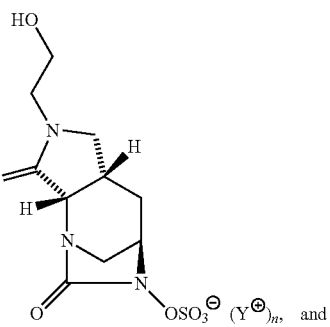 and

-continued

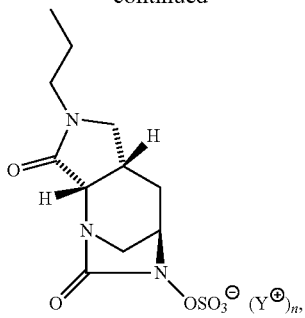

as a salt or zwitterionic form thereof.

The compound of any of the preceding embodiments, wherein n is 1 and Y is selected from sodium, potassium, ammonium, calcium, magnesium, iron, silver, zinc, and copper.

The compound of any of the preceding embodiments, wherein Y is sodium.

The compound of any of the preceding embodiments, which is a pharmaceutically acceptable salt or zwitterion.

An embodiment of special interest is a compound of Formula (VI):

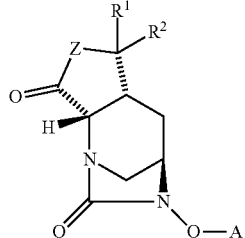

(VI)

wherein:

$R^1$ and $R^2$ are independently selected from H and $C_1$-$C_4$ alkyl optionally substituted with up to three groups selected from halo, CN, —OR, oxo, and —NRR';

Z is $NR^3$ or N—$OR^3$;

$R^3$ is independently selected at each occurrence from H, Cy, and $C_1$-$C_4$ alkyl optionally substituted with up to three groups selected from Cy, halo, CN, —OR, and —NRR';

Cy is a $C_3$-$C_6$ cycloalkyl ring or 4-6 membered heterocyclic ring containing one or two heteroatoms selected from N, O and S as ring members, and Cy is optionally substituted with up to three groups selected from oxo, halo, $C_1$-$C_2$ alkyl, CN, —OR, and —NRR'; and R and R' are independently selected from H and $C_1$-$C_4$ alkyl optionally substituted with one or two groups selected from halo, $C_1$-$C_2$ alkyl, —OH, —CN, —O—($C_1$-$C_4$ alkyl), oxo, —$NH_2$, —NH($C_1$-$C_4$ alkyl), and —N($C_1$-$C_4$ alkyl)$_2$, or R and R' taken together with the nitrogen atom to which both are attached can form a ring selected from piperidine, morpholine, pyrrolidine, and azetidine, wherein the ring is optionally substituted with one or two groups selected from halo, $C_1$-$C_2$ alkyl, —OH, —CN, —O—($C_1$-$C_4$ alkyl), oxo, —$NH_2$, —NH($C_1$-$C_4$ alkyl), and —N($C_1$-$C_4$ alkyl)$_2$;

A is H or —$CH_2$-Ph, where Ph represents phenyl optionally substituted with one or two groups selected from halo, $C_1$-$C_4$ alkyl, $C_1$-$C_4$ alkoxy;

or a salt or zwitterion thereof.

An embodiment of special interest is a compound of the formula (VII):

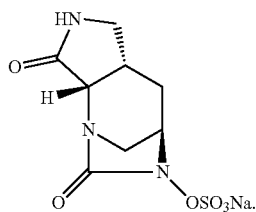

The compound of embodiment 12 in crystalline form.

The compound of embodiment 13, which exhibits an endotherm on differential scanning calorimetry between 283° C. and 350° C.

The compound of embodiment 13, characterized by XRPD peaks at diffraction angles (2Theta) of 8.3 and 16.6 degrees.

The compound of embodiment 15, further characterized by one or more additional XRPD peaks at diffraction angles (2Theta) of 25.1 or 31.3 degrees.

The compound of embodiment 16, further characterized by one or more additional XRPD peaks at diffraction angles (2Theta) of 27.4 or 28.7 degrees.

The compound of embodiment 17, further characterized by additional XRPD peaks at diffraction angles (2Theta) of 19.5 degrees or 21.7 degrees.

A process to make a compound of Formula (I),

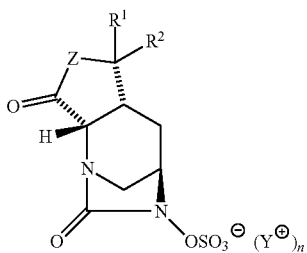 (I)

according to embodiment 3, as a salt or zwitterionic form thereof;

wherein the process comprises contacting a compound of Formula (III)

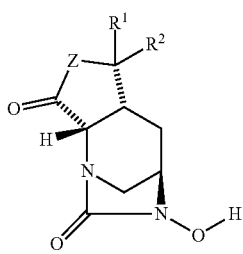 (III)

wherein Z, $R^1$ and $R^2$ and $R^3$ are as defined in embodiment 3, with a sulfonylating agent in the presence of a base.

The process of embodiment 19, wherein Z is $NR^3$, and $R^3$ is H or $C_1$-$C_2$ alkyl optionally substituted with —OR or —NRR', or a pharmaceutically acceptable salt thereof.

The process of embodiment 19 or 20, wherein the compound of Formula (I) is of the formula

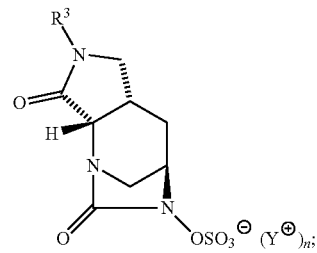

or a salt or zwitterionic form thereof.

The process of any one of embodiments 19 to 21, wherein $R^3$ is H.

The compounds of Formula (III) are useful for synthesizing compounds of Formula (I) as described in Embodiment 3 and other embodiments above.

Specific compounds of Formula (A) and Formula (I) include:

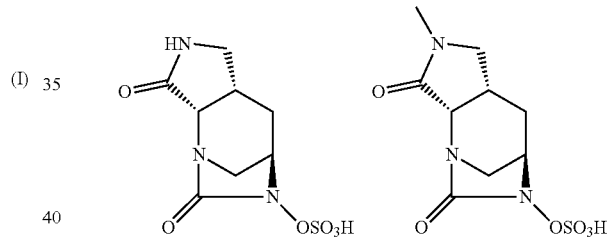

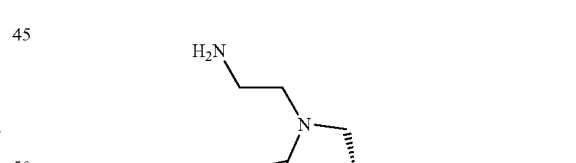

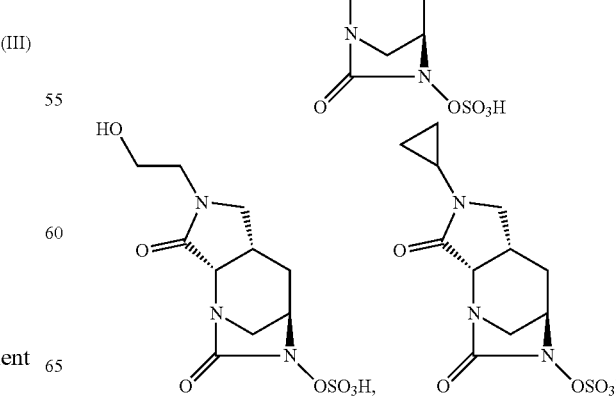

-continued

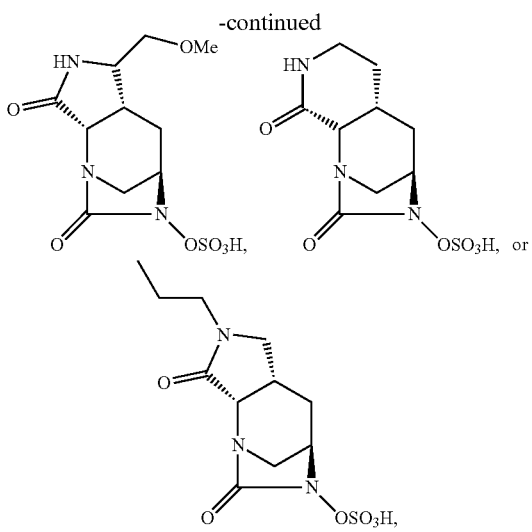

or a salt or zwitterion thereof.

In a further aspect, the invention provides:

A pharmaceutical combination comprising (a) a first therapeutic agent which is a compound of the invention, e.g. a compound of formula (A) or any subformula thereof described herein, and (b) a second therapeutic agent as described above. The second therapeutic agent is typically a beta-lactam antibiotic.

A method as defined above comprising co-administration, e.g. concomitantly or in sequence, of a therapeutically effective amount of a compound of the invention, e.g. a compound of formula (A) or any subformulae thereof that is described herein, and a second therapeutic agent as described above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. Fixed combinations are also within the scope of the present invention. The administration of a pharmaceutical combination of the invention results in a beneficial effect, e.g. a synergistic therapeutic effect, compared to a monotherapy applying only one of its pharmaceutically active ingredients.

Each component of a combination according to this invention may be administered separately, together, or in any combination thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

The compounds of the invention may be synthesized by the general synthetic routes below, specific examples of which are described in more detail in the Examples.

Compounds of the present invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds, or a salt of the compounds like the tetrabutylammonium salt, with metal compounds, such as alkali metal salts of suitable organic carboxylic acids, e.g. the sodium salt of 2-ethylhexanoic acid in appropriate suitable solvent, such as an isobutanol/water mixture, which may facilitate the undesired ion pair (e.g. the tetrabutyl ammonium 2-ethylhexanoate if the tetrabutyl ammonium salt is used) to precipitate. Preferably, a salt of a compound of the invention, such as the ammonium salt, may be subjected to an ion exchange resin in its alkali metal or alkaline earth metal form to promote a counterion exchange. Acid addition or exchange salts of compounds of the present invention are obtained in customary manner, e.g. by treating the compounds with an acid or a suitable anion exchange reagent. Zwitterions or internal salts of compounds of the present invention containing acid and basic salt-forming groups, e.g. a free sulfate group and a free amino group, may be formed, e.g. by the neutralization of salts, such as acid addition salts, to the isoelectric point, e.g. with weak bases, or by treatment with ion exchangers.

Salts can be converted into the free compounds in accordance with methods known to those skilled in the art. Hydrochloride salts can be converted, for example, by treatment with a suitable basic agent. Mixtures of isomers obtainable according to the invention can generally be separated in a manner known to those skilled in the art into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All process steps for making compounds of the invention can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methylcyclohexane, or mixtures of those solvents, for example aqueous solutions, unless otherwise indicated in the description of the processes. Such solvent mixtures may also be used in working up, for example by chromatography or partitioning.

The compounds of the present invention, including their salts, may also be obtained in the form of hydrates, or their crystals may, for example, include the solvent used for crystallization. Different crystalline forms may be present.

All starting materials, building blocks, reagents, acids, bases, dehydrating agents, solvents and catalysts utilized to synthesize the compounds of the present invention are either commercially available or can be produced by organic synthesis methods known to one of ordinary skill in the art.

The term "optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including salt or zwitterionic forms thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or sulfate groups or groups similar thereto.

Pharmaceutically acceptable acid addition or exchange salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids or "Anionic Groups" that can be introduced or from which salts can be derived include, for example, hydrochloric acid, hydrobromic acid, sulfuric acid, nitric acid, phosphoric acid, and the like.

Organic acids or "Anionic Groups" that can be introduced or from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition or exchange salts can be formed with inorganic and organic bases.

Inorganic bases or "Cationic Groups" that can be introduced or from which salts can be derived include, for example, ammonium salts and metals from columns I to XII of the periodic table. In certain embodiments, the salts are derived from the cationic groups sodium, potassium, ammonium, calcium, magnesium, iron, silver, zinc, and copper; particularly suitable salts include ammonium, potassium, sodium, calcium and magnesium salts.

Organic bases or "Cationic Groups" that can be introduced or from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Preferably, a salt of a compound of the invention, such as an ammonium salt, may be subjected to an ion exchange resin in its alkali metal or alkaline earth metal form to promote a counterion exchange. Acid addition or exchange salts of compounds of the present invention are obtained in customary manner, e.g. by treating the compounds with an acid or a suitable anion exchange reagent. Zwitterions or internal salts of compounds of the present invention containing acid and basic salt-forming groups, e.g. a free sulfate group and a free amino group, may be formed, e.g. by the neutralization of salts, such as acid addition salts, to the isoelectric point, e.g. with weak bases, or by treatment with ion exchangers. Such reactions are typically carried out in water or in an organic solvent, or in a mixture of the two. Generally, use of non-aqueous media like ether, ethyl acetate, ethanol, isopropanol, or acetonitrile is desirable, where practicable. Additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds of the present invention. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds of the present invention, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The present invention provides novel compounds, pharmaceutical formulations including the compounds, and methods of treating Gram-negative bacterial infections. Particularly, the compounds are suitable for use to treat infections caused by *Burkholderia, Citrobacter, Enterobacter, Escherichia, Klebsiella, Morganella, Pseudomonas, Proteus, Salmonella, Serratia, Acinetobacter, Bacteroides, Campylobacter, Neisseria*, or *Stenotrophomonas* bacteria, including species named herein.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. For example, deuterium substitution at non-exchangeable hydrocarbon bonds (e.g., C—H) may retard epimerization and/or metabolic oxidation in vivo.

Isotopically-labeled compounds of the invention, i.e. compounds of formula (A), can generally be prepared by conventional techniques known to those skilled in the art or by processes analogous to those described in the accompanying Examples and Preparations Sections using an appropriate isotopically-labeled reagent in place of the non-labeled reagent previously.

In still another aspect, the invention provides a method for treating a subject with a bacterial infection, the method comprising the step of administering to the subject in need thereof an antibacterially effective amount of a compound of the invention, e.g., a compound of Formula (A) or salt thereof with a pharmaceutically acceptable carrier, in combination with a beta-lactam antibiotic. Suitable beta-lactam antibiotics for use in these methods include, but are not limited to, penicillins such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cephalosporins such as cepalothin, cephapirin, cephradine, cephaloridine, cefazolin, cefamandole, cefuroxime, cephalexin, cefprozil, cefaclor, loracarbef, cefoxitin, cefinetazole, cefotaxime, ceftizoxime, ceftriaxone, cefoperazone, ceftazidime, cefixime, cefpodoxime, ceftibuten, cefdinir, cefpirome, cefepime, ceftolozane; carbapenems such as doripenem, imipenem, meropenem, panipenem, biapenem; and monobactams such as aztreonam, and beta-lactam 5, which is disclosed herein.

An "effective amount" of a compound of the invention is an amount that substantially potentiates the activity of a beta-lactam antibiotic used in combination with the compound of the invention, such as an amount that causes the antibiotic to be at least four times more active against a target bacterium, i.e. an amount that lowers the minimum inhibitory concentration (or "minimal inhibitory concentration", "MIC") for the target bacterium by at least 4× and preferably by at least 8×.

An "effective amount" of a combination of a BLI plus beta-lactam antibiotic as used herein refers to an amount effective to treat a bacterial infection in a subject, typically a human subject. The effective amount depends upon the sensitivity of the infecting bacterium to the chosen antibiotic and on the degree of potentiation provided by the BLI used in the combination. The skilled person can determine an effective amount of such combinations based on parameters of the subject to be treated, the infecting bacterium, and the combination to be used, which may include determining the MIC for the particular combination on the targeted bacterium. Typically, the bacterium to be treated is one that is resistant to at least some beta-lactam antibiotics because the bacterium expresses a beta-lactamase activity.

The compounds of the invention also are useful in the treatment of patients suffering from or susceptible to skin infections, pneumonia, sepsis, cystic fibrosis, wound, complicated diabetic foot, complication intra abdominal infections or complicated urinary tract infections and sexually transmitted diseases caused by Gram-negative or Gram-positive pathogens. The compounds of the invention also are useful in the conditions that are caused by a species of *Citrobacter, Enterobacter, Escherichia, Klebsiella, Morganella, Proteus, Salmonella, Serratia, Pseudomonas, Acinetobacter, Bacteroides, Burkholderia, Campylobacter, Neisseria*, or *Stenotrophomonas*. In particular, a bacterial infection caused by a species of *Citrobacter, Enterobacter, Escherichia, Klebsiella, Morganella, Proteus, Salmonella, Serratia, Pseudomonas*, or *Acinetobacter* is treatable by methods herein. Particular bacterial species for such treatment include *Citrobacter freundii, Citrobacter koseri, Enterobacter cloacae, Enterobacter faecalis, Enterobacter faecium, Escherichia coli, Klebsiella pneumonia, Klebsiella oxytoca, Morganella morganii, Proteus mirabilis, Salmonella species, Serratia marcescens, Pseudomonas aeruginosa*, and *Acinetobacter baumannii*, as well as *Bacteroides fragilis, Burkholderia cepacia, Campylobacter jejuni, Neisseria gonorrhoeae*, and *Stenotrophomonas maltophilia*.

By the term "combination", is meant either a fixed combination in one dosage unit form, or a kit or instructions for the combined administration where a compound of the present invention and a combination beta-lactam antibiotic partner may be administered independently or together, at the same time or separately within time intervals that especially allow that the combination partners show a cooperative, e.g., synergistic, effect, or any combination thereof.

An embodiment of the present invention provides compounds of the present invention in a pharmaceutical combination with a beta-lactam antibiotic and a third therapeutic agent. In some embodiments, the third therapeutic agent is an additional antibacterial agent or an additional beta-lactamase inhibitor. In some embodiments, the combination includes at least one other antibacterial agent, which may be another beta-lactam antibiotic or another antibacterial agent selected from the classes described below. Non-limiting examples of additional antibacterial agents for use in pharmaceutical combinations of the invention may be selected from the following groups:

(1) Macrolides or ketolides such as erythromycin, azithromycin, clarithromycin, and telithromycin;

(2) Beta-lactam antibiotics including penicillin such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cephalosporin such as cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, ceftolozane and carbapenems such as doripenem, imipenem, meropenem, panipenem, and monobactams such as aztreonam, and beta-lactam 5 herein;

(3) Glycopeptides such as vancomycin and teicoplanin;

(4) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin, delafloxacin and pazufloxacin;

(5) Antibacterial sulfonamides and antibacterial sulphanilamides, including para-aminobenzoic acid, sulfadiazine, sulfisoxazole, sulfamethoxazole and sulfathalidide;

(6) Aminoglycosides such as streptomycin, neomycin, kanamycin, paromycin, gentamicin, tobramycin, amikacin, netilmicin, spectinomycin, sisomicin, dibekalin, plazomicin and isepamicin;

(7) Tetracyclines such as tetracycline, chlortetracycline, demeclocycline, minocycline, oxytetracycline, methacycline, doxycycline, tigecycline and eravacyclin;

(8) Rifamycins such as rifampicin (also called rifampin), rifapentine, rifabutin, bezoxazinorifamycin and rifaximin;

(9) Lincosamides such as lincomycin and clindamycin;

(10) Streptogramins such as quinupristin and daflopristin;

(11) Oxazolidinones such as linezolid or tedizolid;

(12) Polymyxin, colistin and colymycin;

(13) Trimethoprim and bacitracin; and

(14) Efflux pump inhibitors

(15) Beta-lactamase inhibitors, such as metallo beta-lactamase inhibitors.

The beta-lactam or second antibacterial agent may be administered in combination with the compounds of the present inventions wherein the beta-lactam or second antibacterial agent is administered prior to, simultaneously, or after the compound or compounds of the present invention. When simultaneous administration of a compound of the invention with a second or third agent is desired and the route of administration is the same, then a compound of the invention may be formulated with a second or third agent into the same dosage form. An example of a dosage form containing a compound of the invention and a second or third agent is an intravenous administration. An alternative example is an intramuscular administration of a solution comprising a compound of the invention and a second or third agent.

The compounds and compositions described herein can be used or administered in combination with a beta-lactam and one or more therapeutic agents that act as immunomodulators, e.g., an activator of a costimulatory molecule, or an inhibitor of an immune-inhibitory molecule, or a vaccine. The Programmed Death 1 (PD-1) protein is an inhibitory member of the extended CD28/CTLA4 family of T cell regulators (Okazaki et al. (2002) Curr Opin Immunol 14: 391779-82; Bennett et al. (2003) J. Immunol. 170:711-8). PD-1 is expressed on activated B cells, T cells, and monocytes. PD-1 is an immune-inhibitory protein that negatively regulates TCR signals (Ishida, Y. et al. (1992) EMBO J. 11:3887-3895; Blank, C. et al. (Epub 2006 Dec. 29) Immunol. Immunother. 56(5):739-745), and is up-regulated in chronic infections. The interaction between PD-1 and PD-L1 can act as an immune checkpoint, which can lead to, e.g., a decrease in infiltrating lymphocytes, a decrease in T-cell receptor mediated proliferation, and/or immune evasion by cancerous or infected cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66). Immunomodulation can be achieved by binding to either the immune-inhibitory protein (e.g., PD-1) or to binding proteins that modulate the inhibitory protein (e.g., PD-L1, PD-L2).

In one embodiment, the combination therapies of the invention include an immunomodulator that is an inhibitor or antagonist of an inhibitory molecule of an immune checkpoint molecule. In another embodiment the immunomodulator binds to a protein that naturally inhibits the immuno-inhibitory checkpoint molecule. When used in combination with antibacterial compounds, these immunomodulators can enhance the antimicrobial response, and thus enhance efficacy relative to treatment with the antibacterial compound alone.

The term "immune checkpoints" refers to a group of molecules on the cell surface of CD4 and CD8 T cells. These molecules can effectively serve as "brakes" to down-modulate or inhibit an adaptive immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells. Immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 2B4 and/or TGFR beta. Inhibition of an inhibitory molecule can be performed by inhibition at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide, e.g., a soluble ligand, or an antibody or antigen-binding fragment thereof, that binds to the inhibitory molecule.

By "in combination with," it is not intended to imply that the therapy or the therapeutic agents must be administered at the same time and/or formulated for delivery together, although these methods of delivery are within the scope described herein. The immunomodulator can be administered concurrently with, prior to, or subsequent to, one or more compounds of the invention and the beta-lactam partner, and optionally one or more additional therapies or therapeutic agents. The therapeutic agents in the combination can be administered in any order. In general, each agent will be administered at a dose and/or on a time schedule determined for that agent. It will further be appreciated that the therapeutic agents utilized in this combination may be administered together in a single composition or administered separately in different compositions. In general, it is expected that each of the therapeutic agents utilized in combination be utilized at levels that do not exceed the levels at which they are utilized individually. In some embodiments, the levels utilized in combination will be lower than those utilized individually.

In certain embodiments, the beta-inhibitor described herein are administered in combination with a beta-lactam and one or more immunomodulators that are inhibitors of PD-1, PD-L1 and/or PD-L2. Each such inhibitor may be an antibody, an antigen binding fragment thereof, an immunoadhesin, a fusion protein, or an oligopeptide. Examples of such immunomodulators are known in the art.

In some embodiments, the immunomodulator is an anti-PD-1 antibody chosen from MDX-1106, Merck 3475 or CT-011.

In some embodiments, the immunomodulator is an immunoadhesin (e.g., an immunoadhesin comprising an extracellular or PD-1 binding portion of PD-LI or PD-L2 fused to a constant region (e.g., an Fc region of an immunoglobulin sequence).

In some embodiments, the immunomodulator is a PD-1 inhibitor such as AMP-224.

In some embodiments, the immunomodulator is a PD-LI inhibitor such as anti-PD-LI antibody.

In some embodiments, the immunomodulator is an anti-PD-LI binding antagonist chosen from YW243.55.S70, MPDL3280A, MEDI-4736, MSB-0010718C, or MDX-1105. MDX-1105, also known as BMS-936559, is an anti-PD-LI antibody described in WO2007/005874. Antibody YW243.55.S70 is an anti-PD-LI described in WO 2010/077634.

In some embodiments, the immunomodulator is nivolumab (CAS Registry Number: 946414-94-4). Alternative names for nivolumab include MDX-1106, MDX-1106-04, ONO-4538, or BMS-936558. Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

In some embodiments, the immunomodulator is an anti-PD-1 antibody Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) New England Journal of Medicine 369 (2): 134-44, U.S. Pat. No. 8,354,509, WO2009/114335, and WO2013/079174.

In some embodiments, the immunomodulator is Pidilizumab (CT-011; Cure Tech), a humanized IgG1k monoclonal antibody that binds to PD1. Pidilizumab and other humanized anti-PD-1 monoclonal antibodies are disclosed in WO2009/101611.

Other anti-PD1 antibodies useful as immunomodulators for use in the methods disclosed herein include AMP 514 (Amplimmune), and anti-PD1 antibodies disclosed in U.S. Pat. No. 8,609,089, US 2010028330, and/or US 20120114649. In some embodiments, the anti-PD-L1 antibody is MSB0010718C. MSB0010718C (also referred to as A09-246-2; Merck Serono) is a monoclonal antibody that binds to PD-L1.

In some embodiments, the immunomodulator is MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S. Publication No.: 20120039906. Other anti-PD-L1 binding agents useful as immunomodulators for methods of the invention include YW243.55.S70 (see WO2010/077634), MDX-1105 (also referred to as BMS-936559), and anti-PD-L1 binding agents disclosed in WO2007/005874.

In some embodiments, the immunomodulator is AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the immunomodulator is an anti-LAG-3 antibody such as BMS-986016. BMS-986016 (also referred to as BMS986016) is a monoclonal antibody that binds to LAG-3. BMS-986016 and other humanized anti-LAG-3 antibodies are disclosed in US 2011/0150892, WO2010/019570, and WO2014/008218

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include an immunomodulator that is a costimulatory molecule, e.g., an agonist associated with a positive signal that includes a costimulatory domain of CD28, CD27, ICOS and/or GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. No. 7,812,135, U.S. Pat. No. 8,388,967, U.S. Pat. No. 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the immunomodulator used is a soluble ligand (e.g., a CTLA-4-1g), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example. Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, an anti-PD-1 antibody molecule is administered after treatment with a compound of the invention as described herein.

In another embodiment, an anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) Cancer Res. 72(4):917-27).

Exemplary immunomodulators that can be used in the combination therapies include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

Exemplary doses of such immunomodulators that can be used in combination with the antibacterial compounds of the invention include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Examples of embodiments of the methods of using the compounds of the invention in combination with a beta-lactam antibiotic and an immunomodulator include these:

i. A method to treat a bacterial infection in a subject, comprising administering to the subject a compound of Formula (A) as described herein, and an immunomodulator.

ii. The method of embodiment i, wherein the immunomodulator is an activator of a costimulatory molecule or an inhibitor of an immune checkpoint molecule.

iii. The method of either of embodiments i and ii, wherein the activator of the costimulatory molecule is an agonist of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 and CD83 ligand.

iv. The method of any of embodiments i-iii above, wherein the inhibitor of the immune checkpoint molecule is chosen from PD-1, PD-L1, PD-L2, CTLA4, TIM3, LAG3, VISTA, BTLA, TIGIT, LAIR1, CD160, 2B4 and TGFR beta.

v. The method of any of any of embodiments i-iii, wherein the inhibitor of the immune checkpoint molecule is chosen from an inhibitor of PD-1, PD-L1, LAG-3, TIM-3 or CTLA4, or any combination thereof.

vi. The method of any of embodiments i-v, wherein the inhibitor of the immune checkpoint molecule is a soluble ligand or an antibody or antigen-binding fragment thereof, that binds to the immune checkpoint molecule.

vii. The method of any of embodiments i-vi, wherein the antibody or antigen-binding fragment thereof is from an IgG1 or IgG4 (e.g., human IgG1 or IgG4).

viii. The method of any of embodiments i-vii, wherein the antibody or antigen-binding fragment thereof is altered, e.g., mutated, to increase or decrease one or more of: Fc receptor binding, antibody glycosylation, the number of cysteine residues, effector cell function, or complement function.

ix. The method of any of embodiments i-viii, wherein the antibody molecule is a bispecific or multispecific antibody molecule that has a first binding specificity to PD-1 or PD-L1 and a second binding specificity to TIM-3, LAG-3, or PD-L2.

x. The method of any of embodiments i-ix, wherein the immunomodulator is an anti-PD-1 antibody chosen from Nivolumab, Pembrolizumab or Pidilizumab.

xi. The method of any of embodiments i-x, wherein the immunomodulator is an anti-PD-L1 antibody chosen from YW243.55.S70, MPDL3280A, MEDI-4736, MSB-0010718C, or MDX-1105.

xii. The method of any of embodiments i-x, wherein the immunomodulator is an anti-LAG-3 antibody molecule.

xiii. The method of embodiment xii, wherein the anti-LAG-3 antibody molecule is BMS-986016, xiv. The method of any of embodiments i-x, wherein the immunomodulator is an anti-PD-1 antibody molecule administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg., e.g., once a week to once every 2, 3, or 4 weeks.

xv. The method of embodiment xiv, wherein the anti-PD-1 antibody molecule is administered at a dose from about 10 to 20 mg/kg every other week.

xvi. The method of embodiment xv, wherein the anti-PD-1 antibody molecule, e.g., nivolumab, is administered intravenously at a dose from about 1 mg/kg to 3 mg/kg, e.g., about 1 mg/kg, 2 mg/kg or 3 mg/kg, every two weeks.

xvii. The method of embodiment xv, wherein the anti-PD-1 antibody molecule, e.g., nivolumab, is administered intravenously at a dose of about 2 mg/kg at 3-week intervals.

The language "effective amount" of the compound is that amount necessary or sufficient to enhance the efficacy of a beta-lactam antibiotic used to treat or prevent a bacterial infection and/or a disease or condition described herein. In an example, an effective amount of the compound is an amount sufficient to treat bacterial infection in a subject, when dosed together with a beta-lactam. In another example, an effective amount of the compound is an amount sufficient to treat a bacterial infection, when dosed in combination with a beta-lactam antibiotic, caused by, but not limited to species of Enterobacteriaceae and the like in a subject. The effective amount can vary depending on such factors as the size and weight of the subject, the type of illness, the characteristics of the bacterial pathogen causing the illness (for example the type and level of beta-lactamase production) or the particular compound of the invention, as well as the beta-lactam antibiotic to be used along with the compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a bacterial infection. Typically, the compound is administered to a subject diagnosed as having a bacterial infection and in need of treatment therefore. Further, several divided dosages, as well as staggered dosages, can be administered every 6 hours, every 8 hours, every 12 hours or daily or sequentially, or the dose can be continuously infused, or can be a bolus injection. Further, the dosages of the compound(s) of the invention can be proportionally increased or decreased as indicated by the exigencies of the therapeutic or prophylactic situation. Typically, the compound of the invention would be administered over a course of at least 5 days, more commonly at least 7 days or at least 10 days or at least 14 days, through 3 or 4 infusions per day (every 6 or 8 hours).

Compounds of the invention may be used in the treatment of states, disorders or diseases as described herein, or for the manufacture of pharmaceutical compositions for use in the treatment of these diseases. The invention provides methods of use of compounds of the present invention in the treatment of these diseases or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. In some embodiments, a pharmaceutically acceptable carrier is sterilized before combination with the compound of the invention.

In some embodiments, the pharmaceutical composition of the invention comprises a compound of any of the numbered embodiments and at least one pharmaceutically acceptable carrier or excipient. In certain embodiments, the pharmaceutical composition of the invention comprises a compound of any of the numbered embodiments and at least two pharmaceutically acceptable carriers or excipients.

Wetting agents, emulsifiers and lubricants, such as sodium lauryl sulfate and magnesium stearate, as well as preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. Typically, compounds of the invention would be administered intravenously, in the form of a solution that is often isotonic, such as a saline or glucose solution. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Intravenous administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including intramuscular injection, orally, nasally, inhaled as by, for example, a spray, rectally, intravaginally, parenterally, intracisternally and topically, as by powders, ointments or drops, including buccally and sublingually. In some embodiments, the compound of the invention is administered by injection or infusion, often by infusion, and it may be co-administered with a beta-lactam antibiotic. The beta-lactam antibiotic may be administered by any appropriate route; in some embodiments, the beta-lactam antibiotic is administered orally, and in other embodiments the beta-lactam antibiotic is administered by injection or by infusion. When the compound of the invention is co-administered with a beta-lactam antibiotic and both are administered by the same route, they may optionally be admixed for administration by injection or by infusion, or they may be separately administered provided the beta-lactamase inhibitor is present systemically in the treated subject along with the beta-lactam antibiotic so potentiation can occur.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, the genus, species and strain of bacterial pathogen causing the infection and like factors well known in the medical arts.

In general, a suitable daily dose of a compound of the invention will be that amount of the compound that is the dose effective to produce a therapeutic effect. Such an effective dose will generally depend upon the factors described above. Generally, intravenous and subcutaneous doses of the compounds of this invention for a patient, when used in combination with a beta-lactam for the indicated antibacterial effects, will range from about 2 to about 100 mg per kilogram of body weight per day, more preferably from about 5 to about 100 mg per kg per day, and still more preferably from about 10 to about 50 mg per kg per day. An effective amount is that amount treats a bacterial infection, when dosed in combination with a beta-lactam antibiotic.

If desired, the effective daily dose of the active compound may be administered as two, three, four, five, six or more sub-doses administered separately at appropriate intervals throughout the day, optionally, in unit dosage forms, or as continuous infusion.

While it is possible for a compound of the present invention to be administered alone, it is preferable to administer the compound as a pharmaceutical composition.

The compounds as defined in embodiments may be synthesized by the general synthetic routes below, specific examples of which are described in more detail in the Examples.

General Synthetic Schemes

One method for synthesizing compounds of Formula (I) is depicted in the following reaction schemes. Scheme A illustrates functionalization of the known diazabicyclooctane skeleton in protected form to introduce an aminoalkyl group, as described in the working examples. Scheme B illustrates formation of the fused lactam ring, which is also illustrated by the Examples. Scheme C illustrates how the lactam could readily be N-alkylated to introduce an optionally-substituted alkyl group.

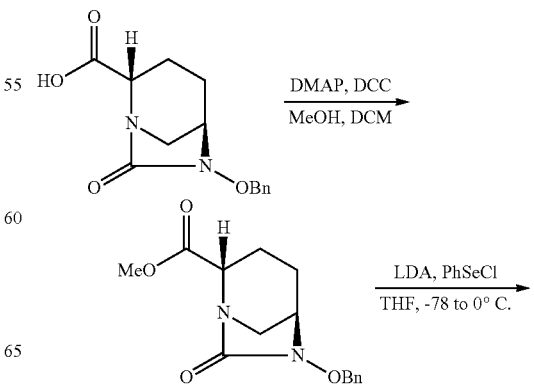

Scheme A

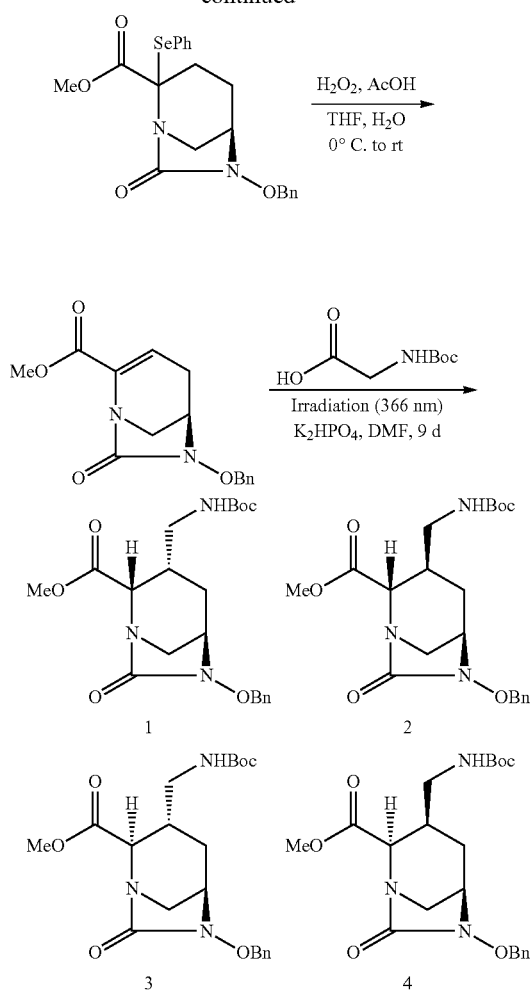

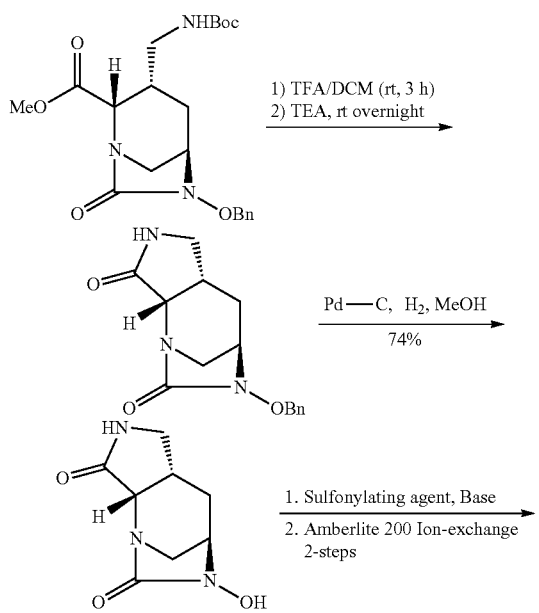

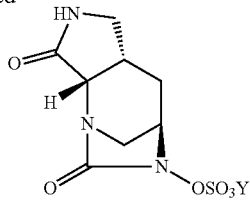

Examples of sulfonylating agents include, but are not limited to sulfurtrioxide pyridine complex, and the like.

Examples of bases include, but are not limited to pyridine and the like.

EXAMPLES

The invention is further illustrated by the following examples, which should not be construed as limiting. The assays used throughout the Examples are accepted Demonstration of efficacy in these assays is predictive of efficacy in subjects.

General Conditions

Mass spectra were acquired on LC-MS, SFC-MS, or GC-MS systems using electrospray, chemical and electron impact ionization methods from a range of instruments of the following configurations: Waters ACQUITY UPLC system and equipped with a ZQ 2000 or SQD MS system where (M+1) refers to the protonated molecular ion of the chemical species, (M+) refers to the unprotonated quaternary ammonium cation and (M−1) refers to the deprotonated molecular ion of the chemical species.

NMR spectra were run on a Bruker BioSpin 600 MHz, Bruker AVANCE 500 MHz or Varian 400 MHz NMR spectrometers using ICON-NMR, under TopSpin program control. Spectra were measured at 298K, unless indicated otherwise, and were referenced relative to the solvent resonance.

Instrumentation

MS Methods:

Method 2m_acidic:

| Column | Kinetex C18 50 × 2.1 mm, 2.6 μm |
|---|---|
| Column Temperature | 50° C. |
| Eluents | A: H$_2$O, B: acetonitrile, both containing 0.1% TFA |
| Flow Rate | 1.2 mL/min |
| Gradient | 2% to 88% B in 1.30 min, 0.15 min 95% B |

Method 2m_acidic_polar:

| Column | Kinetex C18 50 × 2.1 mm, 2.6 μm |
|---|---|
| Column Temperature | 50° C. |
| Eluents | A: H$_2$O, B: acetonitrile, both containing 0.1% TFA |
| Flow Rate | 1.2 mL/min |
| Gradient | 1% to 30% B in 1.30 min, 0.15 min 98% B |

Method T3_3m_polar:

| Column | T3 C18 50 × 2.1 mm, 2.6 μm |
|---|---|
| Column Temperature | 50° C. |
| Eluents | A: H$_2$O, B: acetonitrile, both containing 0.1% TFA |

-continued

| | |
|---|---|
| Flow Rate | 1.2 mL/min |
| Gradient | 100% A for 1.1 min, 30% B in 1.20 min, 95% B in 0.7 min |

Method LCMS_2 MIN_REACTION_MONITORING:

| | |
|---|---|
| Column | Acquity UPLC HSS T3 50 × 2.1 mm, 1.8 µm |
| Column Temperature | 60° C. |
| Eluents | A: $H_2O$, B: acetonitrile, both containing 0.05% TFA |
| Flow Rate | 1.0 mL/min |
| Gradient | 5% to 98% B in 1.4 min |
| UV detection | TAC (210-450 nm) |

Method LCMS_2_MIN_FINAL_ANALYSIS:

| | |
|---|---|
| Column | Acquity UPLC HSS T3 50 × 2.1 mm, 1.8 µm |
| Column Temperature | 60° C. |
| Eluents | A: $H_2O$ (0.05% FA + 3.75 mM AA, B: acetonitrile (0.04% FA) |
| Flow Rate | 1.0 mL/min |
| Gradient | 5% to 98% B in 1.4 min |
| UV detection | TAC (210-450 nm) |

Method LCMS_2_MIN_Polar:

| | |
|---|---|
| Column | Acquity UPLC HSS T3 50 × 2.1 mm, 1.8 µm |
| Column Temperature | 60° C. |
| Eluents | A: $H_2O$ (0.05% FA + 3.75 mM AA, B: acetonitrile (0.04% FA) |
| Flow Rate | 1.0 mL/min |
| Gradient | concave from 1% to 98% B in 1.4 min |
| UV detection | TAC (210-450 nm) |

Method HPLC_CHIRAL:

| | |
|---|---|
| Column | Chiralpak IC KK025 250 × 4.6 mm, 5 µm |
| Column Temperature | rt |
| Eluents | heptane/EtOH/diethylamine 92:8:0.05 |
| Flow Rate | 1.0 mL/min |
| UV detection | 220 nm |

Abbreviations

AA ammonium acetate
ACN acetonitrile
app apparent
ATP adenosine 5'-triphosphate
BINAP racemic 2,2'-bis(diphenylphosphino)-1,1'-binaphthyl
Boc tertiary butyl carboxy
br broad
br s broad singlet
BSA bovine serum albumin
d doublet
dd doublet of doublets
DCC dicyclohexylcarbodiimide
DCE 1,2-dichloroethane
DCM dichloromethane
DIAD diisopropylazodicarboxylate
DIPEA diisopropylethylamine
DMAP 4-(N,N-dimethylamino)pyridine
DME 1,4-dimethoxyethane
DMF N,N-dimethylformamide
DMSO dimethylsulfoxide
EDTA ethylenediamine tetraacetic acid
ESI electrospray ionization
EtOAc ethyl acetate
FA formic acid
g gram
h hour(s)
HATU 1-[Bis(dimethylamino)methylene]-1H-1,2,3-triazolo[4,5-b]pyridinium 3-oxid hexafluorophosphate
HBTU 1-[bis(dimethylamino)methylene]-1H-benzotriazoliumhexafluorophosphate(1-) 3-oxide
HCl hydrochloric acid
HOBt 1-hydroxybenzotriazole
HPLC high performance liquid chromatography
LCMS liquid chromatography and mass spectrometry
LDA lithium diisopropylamide
MeOH methanol
MS mass spectrometry
m multiplet
mg milligram
MIC minimum or minimal inhibitory concentration
min minutes
mL milliliter
mmol millimole
m/z mass to charge ratio
NMR nuclear magnetic resonance
o/n overnight
p pentet
$PdCl_2$(dppf)-$CH_2Cl_2$ 1,1'-Bis(diphenylphosphino)ferrocene-palladium(II)dichloride dichloromethane complex
ppm parts per million
PyBOP benzotriazol-1-yloxytripyrrolidinophosphonium hexafluorophosphate
q quartet
rac racemic
rbf round bottom flask
rt room temperature
$R_t$ retention time
s singlet
t triplet
TBME methyl tert-butyl ether
TFA trifluoroacetic acid
TFAA trifluoroacetic acid anhydride
THF tetrahydrofuran
Tris-HCl aminotris(hydroxymethyl)methane hydrochloride Preparation of Intermediates

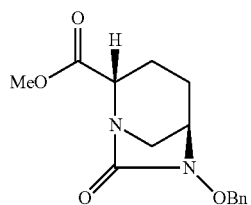 [SMILES: COC(=O)[C@@H]1CC[C@@H]2CN1C(=O)N2OCc1ccccc1]

Intermediate A: Methyl (2S,5R)-6-(benzyloxy)-7-oxo-1,6-diazabicyclo[3.2.1]octane-2-carboxylate To a solution of (2S,5R)-6-(benzyloxy)-7-oxo-1,6-diazabicyclo[3.2.1]octane-2-carboxylic acid (5.0 g, 18.1 mmol), MeOH (880 μL, 21.7 mmol) and DMAP (44 mg, 0.36 mmol) in DCM (50 mL) at 0° C. was added DCC (3.92 g, 19.0 mmol). After 2 h at rt it was diluted with DCM and washed with water then brine. The aqueous layers were extracted with DCM (2×) and the combined organic layers were dried over $Na_2SO_4$, filtered then concentrated in vacuo. The crude residue was triturated with diethyl ether, filtered and concentrated in vacuo. The crude filtrate was purified silica gel chromatography to afford the title compound (4.3 g, 82%). LCMS $R_t$=0.87 min, m/z=291.3 (M+1), Method 2 MIN_REACTION_MONITORING.

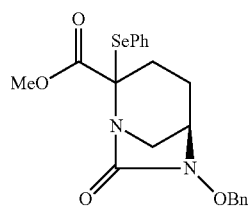

Intermediate B: Methyl (5R)-6-(benzyloxy)-7-oxo-2-(phenylselanyl)-1,6-diazabicyclo[3.2.1]octane-2-carboxylate To a solution of diisopropylamine (29.6 ml, 210 mmol) in THF (800 mL) at −70° C. was added n-butyllithium (1.6 M in hexanes, 108 ml, 172 mmol) drop-wise over 10 minutes. After stirring for 50 minutes at −73° C. a solution of methyl (2S,5R)-6-(benzyloxy)-7-oxo-1,6-diazabicyclo[3.2.1]octane-2-carboxylate (43.5 g, 150 mmol) in THF (350 mL) was added drop-wise over 45 minutes. After stirring at −78° C. for 1.5 hours phenylselenyl chloride (57.4 g, 300 mmol) in THF (260 mL) was added dropwise over 45 minutes. After stirring at −78° C. for 45 min it was allowed to warm to −10° C. over 60 minutes and stirred for an additional hour, whereupon it was cooled to −30° C. and quenched with HCl (2 M, 50 mL) followed by addition of methanol (250 mL). The mixture was allowed to reach rt over 15 min then diluted with TBME (1 L) and washed with brine:water (2:1, 2 L). The phases were separated and the organic phase was washed brine (2 L). The aqueous layers were extracted with TBME (2×500 mL). The combined organic phases were dried over $Na_2SO_4$, filtered and concentrated in vacuo. The crude residue was purified via silica gel chromatography, affording the title compound (23.70 g, 36%, 3:1 mix of diastereomers) as a brown oil. LCMS $R_t$=1.12/1.16 min, m/z=447.3 (M+1), Method 2 MIN_REACTION_MONITORING; $^1$H NMR (600 MHz, $CDCl_3$, major diastereomer) δ 7.59 (d, J=7.9 Hz, 2H), 7.42-7.30 (m, 8H), 5.00 (d, J=11.5 Hz, 1H), 4.88 (d, J=11.5 Hz, 1H), 4.15 (d, J=11.7 Hz, 1H), 3.68 (s, 3H), 3.35 (s, 1H), 3.18 (d, J=11.8 Hz, 1H), 2.44 (ddd, J=17.4, 11.8, 6.6 Hz, 1H), 2.07-2.01 (m, 1H), 1.91 (dd, J=16.6, 5.8 Hz, 1H), 1.72 (td, J=12.9, 6.0 Hz, 1H).

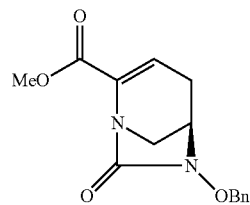 [SMILES: COC(=O)C1=CC[C@@H]2CN1C(=O)N2OCc1ccccc1]

Intermediate C: Methyl (5R)-6-(benzyloxy)-7-oxo-1,6-diazabicyclo[3.2.1]oct-2-ene-2-carboxylate To a solution of Intermediate B in THF:water (20:1, 22 mL) at 0° C. was added $H_2O_2$ (30% aq, 0.8 mL, 7.83 mmol) and AcOH (0.55 mL, 9.61 mmol). After stirring for 1 hour at 0° C. it was diluted with EtOAc and potassium sulfite (5% aq) was added. Upon destruction of all peroxides (KJ-starke-test), the phases were separated and the organic layer was washed with brine. The aqueous layers were extracted with EtOAc and the combined organic layers were washed with $NaHCO_3$ (5% aq), brine, dried over $Na_2SO_4$, filtered and concentrated in vacuo. The crude residue was purified via silica gel chromatography to afford the title compound (419 mg, 81%). LCMS: $R_t$=0.88 min, m/z=288.1 (M+1), Method 2_MIN_FINAL_ANALYSIS. $^1$H NMR (600 MHz, DMSO-$d_6$) δ 7.45-7.41 (m, 2H), 7.40-7.33 (m, 3H), 6.88-6.86 (m, 1H), 4.89 (s, 2H), 3.96 (br s, 1H), 3.67 (s, 3H), 3.35-3.28 (m, 1H), 2.82 (d, J=11.0 Hz, 1H), 2.58-2.52 (m, 1H), 2.38 (s, 1H), 2.34 (s, 1H).

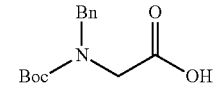

Intermediate D: N-benzyl-N-(tert-butoxycarbonyl)glycine

To a suspension of N-benzylglycine (24.3 g, 147 mmol) in THF:water (1:1, 500 mL) was added Boc-anhydride (33.7 g, 154 mmol). After 6.5 h the mixture was diluted with TBME (250 mL) and citric acid (33 g) was added until pH=4. After 10 min of stirring, the phases were separated and the organic phase was washed with brine (250 ml). The aqueous layer was washed with TBME (2×100 ml) and the combined organic phases were dried over $Na_2SO_4$, filtered then concentrated in vacuo (45° C.), affording the title compound (40.70 g) as a colorless oil, which began to crystallize upon standing. HPLC: 99.7% by UV, LCMS: $R_t$=0.94 min, m/z=264.3 (M−H), Method LCMS_2_MIN_FINAL_ANALYSIS. $^1$H NMR (600 MHz, DMSO-$d_6$)* δ 12.62 (br s, 1H), 7.44-7.09 (m, 5H), 4.41 (d, J=8.1 Hz, 2H) 1.44-1.24 (m, 9H) 3.89-3.67 (m, 2H). *As a mixture with $O(Boc)_2$ (ca. 9%).

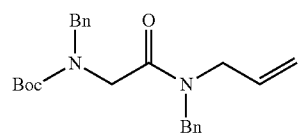 [SMILES: C=CCN(Cc1ccccc1)C(=O)CN(Cc1ccccc1)C(=O)OC(C)(C)C]

Intermediate E: tert-Butyl (2-(allyl(benzyl)amino)-2-oxoethyl)(benzyl)carbamate A 1500 mL-4-neck reaction flask with mechanical stirrer, internal thermometer, condenser and nitrogen inlet was charged with intermediate D (31.6 g, 107 mmol) followed by EtOAc (500 ml). The reaction mixture was cooled in a ice bath (4° C.) followed by addition of N-allylbenzylamine (16.44 g, 107 mmol) and propylphosphonic anhydride (T3P, 136 g, 214 mmol, 50% in ethyl acetate). To the mixture was added triethylamine (90 ml, 643 mmol), drop-wise over 5 min. The brown solution was stirred for 20 min at rt then poured into a stirred mixture of ice water (500 ml). The phases were separated and the organic phase was washed successively with HCl (0.5 N, 500 mL), saturated NaHCO$_3$ (500 mL) and brine (500 mL). The initial aqueous layer was extracted with EtOAc (2×250 mL) and the combined organic layers were dried over Na$_2$SO$_4$, filtered and concentrated in vacuo at (45° C.), affording the title compound (43.94 g) as a brown oil. LCMS: R$_t$=1.31, min m/z=395.5 (M+1), method LCMS_2_MIN_FINAL_ANALYSIS. $^1$H NMR (400 MHz, DMSO-d$_6$) δ 7.53-6.99 (m, 10H), 5.94-5.55 (m, 1H), 5.24-4.97 (m, 2H) 4.55-4.25 (m, 4H), 4.16-3.68 (m, 4H), 1.42-1.28 (m, 9H).

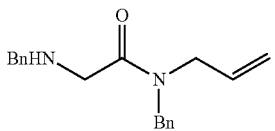

Intermediate F: N-allyl-N-benzyl-2-(benzylamino)acetamide

A 750 ml 4-neck reaction flask equipped with mechanical stirrer, internal thermometer, condenser and nitrogen inlet was charged with intermediate E (43.9 g, 108 mmol) in DCM (400 mL). To the solution was added TFA (83 ml, 1.079 mol). After stirring o/n the yellow solution was slowly poured (rapid gas evolution) into a stirred mixture of saturated NaHCO$_3$ solution (aq, 1.5 L) and ice (1 kg). After 10 min of stirring the phases were separated and the organic phase was washed with % saturated NaHCO$_3$ (aq, 0.5 L) then brine (0.5 L). The aqueous layer was extracted with DCM (0.5 L) and the combined organic layers were dried over Na$_2$SO$_4$, filtered and concentrated in vacuo (45° C.) to afford the title compound (31.30 g) as a brown oil. LCMS: R$_t$=0.71 min m/z=295.3 (M+1), method LCMS_2_MIN_FINAL_ANALYSIS. $^1$H NMR (400 MHz, DMSO-d$_6$) δ ppm 7.49-7.04 (m, 10H), 5.90-5.55 (m, 1H), 5.19-4.92 (m, 2H), 4.64-4.37 (m, 2H), 3.98-3.76 (m, 2H), 3.73-3.61 (m, 2H), 3.44-3.32 (m, 2H), 2.44-2.28 (m, 1H).

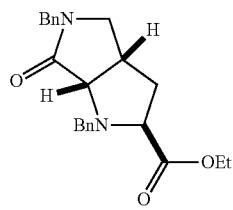 [SMILES: CCOC(=O)[C@@H]1C[C@H]2CN(Cc3ccccc3)C(=O)[C@H]2N1Cc1ccccc1]

Intermediate G: rac ethyl (2S*3aS*,6aS*)-1,5-dibenzyl-6-oxooctahydropyrrolo[3,4-b]pyrrole-2-carboxylate To a nitrogen inertized 60 L Buechi reactor CR60 equipped with a Huber thermostat 390W, Flexy ALR with automated temperature, dosage control and nitrogen inlet were added a solution of intermediate F (1.460 kg, 4.81 mol) in toluene (20 L), magnesium sulfate (2.32 kg, 19.24 mol) and triethylamine (0.872 L, 6.25 mol). The pale yellow suspension was heated to reflux within 1 hour. To the refluxing mixture was added ethyl glyoxylate (50% in toluene, 1.179 kg, 5.77 mol) over 15 h via a dosage pump. After stirring for an additional 6 h at reflux, the yellow suspension was cooled to 15° C. (internal temp), whereupon water (20 L) was added (exothermic). After stirring for 15 min, the mixture was transferred to a 80 L-separation vessel and the phases were separated. The organic layer was extracted successively with water (15 L) then brine (15 L). The aqueous layer was washed with TBME (2×10 L). The second TBME wash was filtered through celite (contained insoluble material), eluting with TBME. The combined organic phases were partially concentrated in vacuo (45° C.) to a volume of 6 L, dried over Na$_2$SO$_4$, filtered and concentrated in vacuo (50° C.). This material was further dried overnight (50° C., 10 mbar) to afford the title compound (1.970 kg) as a brown oil that was a 5.2:1 mixture of diastereomers. LCMS: R$_t$=1.21 min (67.1% a) m/z=379.3 (M+1); (12.9% a) at R$_t$=1.16 min m/z=379.3 (M+1), method LCMS_2_MIN_FINAL_ANALYSIS.

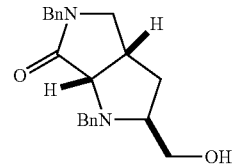 [SMILES: O=C1[C@@H]2[C@@H](C[C@@H](CO)N2Cc2ccccc2)CN1Cc1ccccc1]

Intermediate H: rac (2S*,3aS*,6aS*)-1,5-dibenzyl-2-(hydroxymethyl)-hexahydropyrrolo-[3,4-b]pyrrol-6(1H)-one To a solution of intermediate G (1.967 kg, 5.847 mol) in THF (20 L) at 0° C. within a nitrogen inertized 30 L Büchi reactor CR30 equipped with a Huber thermostat 1015W, Flexy ALR, automated temperature control and nitrogen inlet was added lithium borohydride (0.238 kg, 10.39 mol) in portions over 10 min (slight exotherm). After 5 days at rt additional lithium borohydride (0.025 kg, 1.143 mol) was introduced. After an additional 5 days at rt lithium borohydride (0.017 kg, 0.780 mol) was added. After 6 more days the mixture was cooled to −10° C., whereupon HCl (2 N, 8 L) was added dropwise via dosage pump over 2 h resulting in a pH=3 (caution: very strong gas and foam formation!). After vigorous stirring, a yellow suspension was formed that was stirred for 30 min at 0° C. Saturated NaHCO$_3$ (aq, 10 L) was added and the mixture was transferred to a 80 L-separation vessel and extracted with TBME (20 L) after addition of water (8 L), which aided the phase separation. The organic phase was washed with brine (2×10 L) and the aqueous layer was extracted with TBME (2×7 L). The combined organic layers were concentrated in vacuo (45° C.) to a volume of 8 L, then dried over Na$_2$SO$_4$, filtered and concentrated in vacuo (50° C.). The residue was dissolved in toluene (3 L), concentrated in vacuo and dried for 3 h (50° C., 10 mbar) to afford the title compound (1.630 kg) as a yellow-brown oil, which was a 10.5:1 mixture of diastereomers. LCMS: $R_t$=0.77 min* m/z=337.3 (M+1), method LCMS_2_MIN_FINAL_ANALYSIS. *Major diastereomer.

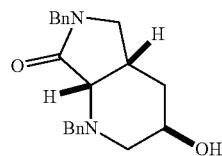 [SMILES: O=C1[C@@H]2[C@@H](C[C@@H](O)CN2Cc2ccccc2)CN1Cc1ccccc1]

Intermediate I: rac (3R*,4aS*,7aS*)-1,6-dibenzyl-3-hydroxyoctahydro-7H-pyrrolo[3,4-b]pyridin-7-one To a suspension of intermediate H (1.627 kg, 4.836 mol), molecular sieves (4 Å, 2.5 kg) and THF (23 L) in a nitrogen inertized 30 L triple jacketed Amsi Glas reactor equipped with automated temperature control, Unistat 390W, reflux condenser and nitrogen inlet at −5° C. was added TFAA (0.820 L, 5.81 mol), dropwise over 35 min. After stirring for 15 min at 0° C., triethylamine (3.37 L, 24.18 mol) was added over 10 min, whereupon it was heated to reflux (internal temperature 68° C.) for 6 days, reaching an equilibrium ratio of product to starting material of 9:1. The mixture was transferred into a 80 L separation vessel containing ice-cold NaOH (1 M, 24 L) and stirred for 15 min. To the brown suspension was added celite (3 kg), where it was stirred for 15 min then filtered over a pad of celite, washing with TBME. The filtrate was extracted with TBME (20 L). The organic phase was washed with saturated NaHCO₃ (aq, 10 L) then brine (1×15 L). The aqueous layers were extracted with TBME (2×7 L) and the combined organic layers were concentrated in vacuo (45° C.) to a volume of 8 L and dried over Na₂SO₄ (2 kg). The suspension was filtered over silica gel (1 kg, 40-63 μm), washing with EtOAc (4×2 L). The eluent was concentrated in vacuo (45° C.) and dried for 3 h (50° C., 15 mbar) to afford the title compound (1.366 kg) as a dark brown oil. LCMS: $R_t$=0.84 min, m/z=337.3 (M+1), method LCMS_2_MIN_FINAL_ANALYSIS. ¹H NMR (600 MHz, DMSO-d₆) δ 7.40-7.15 (m, 10H), 4.69-4.57 (m, 1H), 4.65-4.56 (m, 1H), 4.43 (d, J=13.8 Hz, 1H), 4.29-4.21 (m, 1H), 3.62-3.49 (m, 1H), 3.46-3.39 (m, 1H), 3.18 (d, J=8.3 Hz, 2H), 2.86 (d, J=5.7 Hz, 1H), 2.70 (dd, J=10.7, 2.7 Hz, 1H), 2.66-2.56 (m, 1H), 1.83-1.67 (m, 2H), 1.39-1.29 (m, 1H).

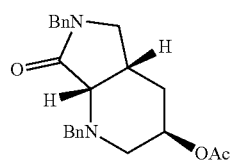 [SMILES: CC(=O)O[C@@H]1C[C@H]2CN(Cc3ccccc3)C(=O)[C@H]2N(Cc2ccccc2)C1]

Intermediate J: (3R,4aS,7aS)-1,6-dibenzyl-7-oxooctahydro-1H-pyrrolo[3,4-b]-pyridin-3-yl acetate A suspension of intermediate I (1.364 kg, 3.04 mol), vinyl acetate (4.20 L, 45.6 mol), Lipase QLM (*Alcaligenes* sp form Meito Sangyo, activity: 101400 U/g, 25 g, 3.04 mol) and TBME (21 L) in a nitrogen inertized 30 L triple jacketed reactor with automated temperature control, Unistat 390W, condenser and nitrogen inlet was stirred at 30° C. (internal temp) for 6 days. The mixture was cooled to 20° C. and filtered over hyflo (500 g). The filtrate was concentrated in vacuo (35° C.) to a volume of 3 L, whereupon toluene (1 L) was added then further concentrated in vacuo (35° C. then at 50° C.). The crude product was dissolved in TBME: heptane (2:1, 3 L) and purified in several portions via silica gel chromatography (heptane-EtOAc-methanol), affording the title compound (626 g) as a brown oil. LCMS: $R_t$=1.16 min, m/z=379.3 (M+1), Method LCMS_2_MIN_FINAL_ANALYSIS. HPLC: $R_t$=33.45 min, 98.2% ee (minor enantiomer: $R_t$=23.92 min) method HPLC_CHIRAL. ¹H NMR (600 MHz, DMSO-d₆) δ ppm 7.41-7.22 (m, 10H), 4.74-4.65 (m, 1H) 4.56-4.51 (m, 1H), 4.36-4.26 (m, 2H), 3.75 (d, J=14.3 Hz, 1H) 3.30-3.21 (m, 2H) 3.00 (dd, J=9.5, 5.9 Hz, 1H), 2.75-2.68 (m, 1H), 2.62 (sxt, J=6.2 Hz, 1H), 2.23 (dd, J=11.6, 7.2 Hz, 1H), 1.97 (s, 3H), 1.66 (t, J=6.05 Hz, 2H).

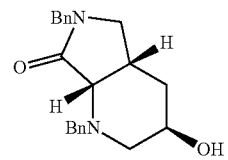 [SMILES: O=C1[C@@H]2[C@@H](C[C@@H](O)CN2Cc2ccccc2)CN1Cc1ccccc1]

Intermediate K: (3R,4aS,7aS)-1,6-dibenzyl-3-hydroxyoctahydro-7H-pyrrolo[3,4-b]-pyridin-7-one A mixture of intermediate J (616 g, 1221 mmol), THF (4 L) and NaOH (2 N, 3.97 L, 7.94 mol) in a 20 L round bottom flask of a Büchi Rotavapor was vigorously stirred for 18 h at 25° C. and 6 h at 40° C., whereupon it was cooled to 25° C. followed by addition of MeOH (2 L) and it was stirred o/n. The mixture was extracted with TBME (6 L) and the organic phase was washed with brine (4 L). The aqueous layer was extracted with TBME (3×3 L) and the combined organic phases were concentrated in vacuo (45° C.) to a volume of 5 L, then dried over anhydrous sodium sulfate (1 kg), filtered and concentrated in vacuo (45° C.). The residue was dissolved in toluene (3 L) and reconcentrated then dried for 2 h (60° C., 20 mbar), affording the title compound (555 g) as a brown oil. LCMS: $R_t$=0.84 min, m/z=337.3 (M+1), Method LCMS_2_MIN_FINAL_ANALYSIS. ¹H NMR (600 MHz, DMSO-d₆) δ 7.58-7.04 (m, 10H), 4.66-4.5 (m, 2H), 4.43 (d, J=13.9 Hz, 1H), 4.25 (d, J=15.2 Hz, 1H), 3.54 (tq, J=9.3, 4.5 Hz, 1H), 3.47-3.39 (m, 1H), 3.18 (d, J=8.3 Hz, 2H), 2.85 (d, J=5.9 Hz, 1H), 2.70 (dd, J=11.0, 2.8 Hz, 1H), 2.64-2.57 (m, 1H), 1.78-1.67 (m, 2H), 1.27-1.39 (m, 1H).

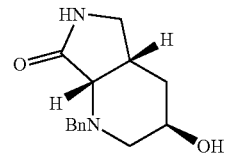 [SMILES: O=C1NC[C@@H]2C[C@@H](O)CN(Cc3ccccc3)[C@H]12]

Intermediate L: (3R,4aS,7aS)-1-benzyl-3-hydroxyoctahydro-7H-pyrrolo[3,4-b]-pyridin-7-one To a 30 L Büchi reactor CR30 equipped with Huber thermostat 1015, Flexy ALR with automated temperature control, argon and ammonia inlet was inertized with argon, precooled to −80° C., filled with liquid ammonia (ahydrous, 10.0 kg, 587 mol), with the outlet attached to a gas scrubber filled with sulfuric acid (30%, 100 L), was added a solution of intermediate K (543 g, 1.614 mol) in THF (1.5 L) followed by ethanol (anhydrous, 236 mL, 4.04 mol). To the resulting solution was added lithium (granular, 44.8 g, 6.46 mol), portionwise over 15 min (temp raised from −72° C. to −63° C.). To the gray mixture, after 1 h, was added lithium (22.4 g, 3.23 mol) and ethanol (anhydrous, 94 mL, 1.616 mol) while maintaining stirring at −60° C. After 1 h, additional lithium (11.2 g, 1.615 mol) and ethanol (anhydrous, 47 mL, 0.808 mol) were added. After 45 min more lithium (11.2 g, 1.615 mol) was added. After 15 h ethanol (anhydrous, 94 mL, 1.616 mol) was added to the deep blue mixture. Stirring was continued until <5% starting material remained and it was quenched by addition of ammonium chloride (2.0 kg, 37.4 mol), portionwise over 10 min. The reaction mixture was stirred for 17 h at −28° C. and ~2 h at 2° C., resulting in complete evaporation of the ammonia. To the mixture was added water (15 L) and TBME (8 L) followed by HCl (32%) until pH=9-10 was obtained. The phases were separated and the organic layer was washed with brine (5 L). The aqueous layer was extracted with DCM (3×2 L) and the combined organic layers were concentrated in vacuo at 45° C. to a volume of 3 L then dried over Na$_2$SO$_4$ (1 kg), filtered and concentrated in vacuo (45° C. then 2 h at 65° C., 20 mbar), affording the title compound (373 g) as a brown oil. LCMS: R$_t$=0.75, m/z=247.2 (M+H), Method LCMS_2_MIN_POLAR. $^1$H NMR (600 MHz, DMSO-d$_6$) δ 7.78 (s, 1H), 7.34-7.24 (m, 4H), 7.27-7.16 (m, 1H), 4.65-4.60 (m, 1H), 4.32 (d, J=13.9 Hz, 1H), 3.64-3.54 (m, 1H), 3.44 (d, J=13.9 Hz, 1H), 3.13 (d, J=8.1 Hz, 2H), 2.69 (dd, J=10.82, 2.75 Hz, 1H), 2.66-2.62 (m, 1H), 2.60-2.54 (m, 1H), 1.80-1.69 (m, 2H), 1.41-1.30 (m, 1H).

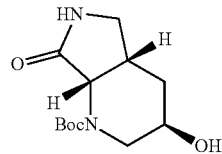 [SMILES: CC(C)(C)OC(=O)N1C[C@H](O)C[C@H]2CNC(=O)[C@H]21]

Intermediate M: tert-butyl (3R,4aS,7aS)-3-hydroxy-7-oxooctahydro-1H-pyrrolo-[3,4-b]pyridine-1-carboxylate To a solution of intermediate L (372.0 g, 1.51 mol) and Boc-anhydride (346 g, 1.59 mol) in THF (4.0 L) was added Pd—C 10% (15 g). The mixture was agitated in a shaking duck apparatus at 22-25° C. and 0.1 bar H$_2$ pressure for 89 h. After 57% hydrogen absorption another portion of Pd—C 10% (15 g) was added. The mixture was filtered over celite, washed with THF and concentrated in vacuo to obtain crude product (545 g) as a pale brown solid. The residue was suspended in EtOAc (1 L) and stirred for 1 hour at 75° C. To the suspension was added heptane (1.5 L), slowly at 75° C. After stirring for 2 h at rt, the product was collected by filtration, the solid was washed with heptane then dried in vacuo (45° C.), affording to title compound (278.5 g) as white crystals. LCMS: R$_t$=0.86 min, m/z=257.3 (M+1), Method LCMS_2_MIN_POLAR. $^1$H NMR (600 MHz, DMSO-d$_6$) δ 7.83-7.65 (m, 1H), 4.80-4.49 (m, 2H), 3.93-3.67 (m, 2H), 3.43-3.37 (m, 1H), 2.72 (br d, J=9.5 Hz, 1H), 2.60 (brd, J=12.5 Hz, 1H), 2.48-2.39 (m, 1H), 1.82-1.70 (m, 1H), 1.40 (brd, J=6.8 Hz, 9H) 1.36-1.27 (m, 1H).

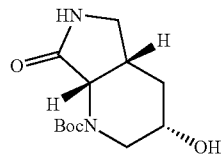 [SMILES: CC(C)(C)OC(=O)N1C[C@@H](O)C[C@H]2CNC(=O)[C@H]21]

Intermediate N: tert-butyl (3S,4aS,7aS)-3-hydroxy-7-oxooctahydro-1H-pyrrolo-[3,4-b]pyridine-1-carboxylate To a solution of intermediate M (270 g, 948 mmol) in THF (13 L) contained in a nitrogen inertized 20 L triple jacketed reactor (Amsi Glas) with automated temperature control, Unistat 390W, condenser and nitrogen inlet at −5° C. (internal temp) was added 4-nitrobenzoic acid (323 g, 1.90 mol) and triphenylphosphine (524 g, 1.90 mol). To the resulting solution was added a solution of DIAD (359 ml, 1.85 mol) in THF (1.3 L), drop-wise over 30 min while maintaining the internal temp at ~4 to −10° C. The mixture was allowed to warm to rt and stirred o/n then concentrated in vacuo (45° C.) to provide crude material (1.64 kg, wet) as a brown oil. To a solution of oil residue in MeOH (15 L) was added K$_2$CO$_3$ (393 g, 2.844 mol). After 1 h of stirring the suspension was concentrated in vacuo (40° C.), providing an orange solid to which DCM (6 L) was added. After 30 min, the suspension was filtered, washing with DCM and the filtrate was concentrated in vacuo (45° C.). The residue was suspended in DCM:MeOH (97:3, 4 L) and stirred for 30 min rt. The suspension was filtered, washing with DCM and the filtrate was concentrated in vacuo (45° C.) to a volume of 3 L and purified in two portions by silica gel chromatography, affording product (189 g) as solid. To this material dissolved in DCM:MeOH (95:5, 5 L) at 45° C. was added heptane (5 L), slowly. The solution was partially concentrated (45° C.), removing some DCM, causing the product to crystallized after 15 min. After 1 h at rt, the solid was collected via filtration, washed with heptane and dried in vacuo (45° C.) until constant weight was obtained, affording the title compound (167.7 g) as crystals. LCMS: R$_t$=0.95 min, m/z=257.3 (M+1), Method LCMS_2_MIN_POLAR. $^1$H NMR (600 MHz, DMSO-d$_6$)* δ 7.80 (d, J=20.2 Hz, 1H), 4.97 (t, J=4.8 Hz, 1H), 4.57 (dd, J=92.2, 7.0 Hz, 1H), 3.89 (ddd, J=18.8, 9.3, 6.5 Hz, 1H), 3.33-3.23 (m, 1H), 2.75 (ddd, J=9.7, 4.6, 2.0 Hz, 1H), 2.43 (ddt, J=16.9, 11.8, 6.1 Hz, 1H), 2.08 (ddd, J=86.6, 12.5, 10.7 Hz, 1H), 1.94 (dd, J=12.2, 5.5 Hz, 1H), 1.39 (d, J=22.6 Hz, 9H), 1.04 (dq, J=15.2, 12.0 Hz, 1H).
*Reported as observed rotamers.

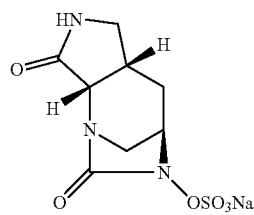

Example 1. Sodium (4R,5aS,8aS)-2,8-dioxohexahydro-2H-1,4-methanopyrrolo[3,4-d][1,3]diazepin-3(4H)-yl sulfate

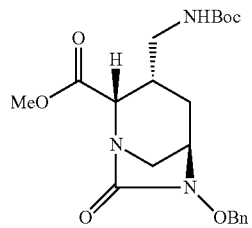 [SMILES: COC(=O)[C@@H]1[C@H](CNC(=O)OC(C)(C)C)C[C@@H]2CN1C(=O)N2OCc1ccccc1]

Step 1: Methyl (2S,3S,5R)-6-(benzyloxy)-3-(((tert-butoxycarbonyl)amino)-methyl)-7-oxo-1,6-diazabicyclo[3.2.1]octane-2-carboxylate Intermediate C (0.82 g, 2.84 mmol), Boc-Gly-OH (1.00 g, 5.69 mmol) and Ir[df(CF$_3$)ppy$_2$(dtbpy)]PF$_6$ (32 mg, 0.028 mmol) were dissolved in DMF (20 mL). To the solution was added finely ground potassium phosphate dibasic (0.59 g, 3.41 mmol) and the resulting suspension was irradiated under argon (balloon) in a 500 mL dropping funnel (closed with a round bottom flask at the bottom and a septum at the top) for 7 days with a 8W UVA fluorescence tube. The flask was placed horizontally on the top of the lamp (air cooled) to ensure maximum irradiation. After 4 days Ir[df(CF$_3$)ppy$_2$(dtbpy)]PF$_6$ (32 mg, 0.028 mmol) was added.

To the mixture were added water (100 mL) then saturated NaHCO$_3$ (aq, 100 mL) and it was extracted with TBME (4×80 mL). The combined organic phases were washed sequentially with saturated NaHCO$_3$ (aq, 50 mL), water (50 mL) then brine (50 mL). The organic layer was dried over Na$_2$SO$_4$, filtered and concentrated in vacuo. The crude residue was purified via silica gel chromatography (EtOAc-heptane, 15-100%) to afford the title compound (108 mg, 9%) as an oil. LCMS: R$_t$=1.04 min, Method 2m_acidic.

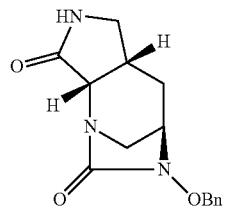 [SMILES: O=C1NC[C@@H]2C[C@@H]3CN(C(=O)N3OCc3ccccc3)[C@H]12]

Step 2: (4R,5aS,8aS)-3-(benzyloxy)hexahydro-2H-1,4-methanopyrrolo[3,4-d][1,3]diazepine-2,8(3H)-dione To a solution of methyl (2S,3S,5R)-6-(benzyloxy)-3-(((tert-butoxycarbonyl)amino)-methyl)-7-oxo-1,6-diazabicyclo[3.2.1]octane-2-carboxylate (108 mg, 0.26 mmol) in DCM (3 mL) at rt was added TFA (1.0 mL, 13 mmol), drop-wise. It was allowed to stir at rt for 3 h, whereupon it was concentrated in vacuo. The crude residue was dissolved in DCM (3 mL), cooled to 0° C., and triethylamine (0.31 mL, 2.3 mmol) was added. After 1 h more triethylamine (0.11 mL, 0.75 mmol) and DCM (5 mL) were added. The ice bath was removed and the reaction mixture was stirred at rt overnight (o/n), whereupon it was washed with citric acid (10 mL, ca 20% aq). The aqueous phase was extracted with DCM (3×8 mL) and the combined organic phases were washed with water (5 mL), brine (2×10 mL), dried over Na$_2$SO$_4$, filtered and concentrated in vacuo. The crude residue was purified via silica gel chromatography (DCM-MeOH, 2-7%) to afford the title compound (47 mg, 61%) as a beige solid. LCMS: R$_t$=0.61 min, m/z=288 (M+1), Method 2m_acidic.

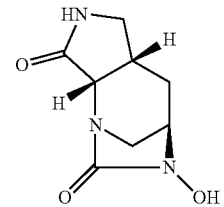 [SMILES: O=C1NC[C@@H]2C[C@@H]3CN(C(=O)N3O)[C@H]12]

Step 3: (4R,5aS,8aS)-3-hydroxyhexahydro-2H-1,4-methanopyrrolo[3,4-d][1,3]diazepine-2,8(3H)-dione A slurry of (4R,5aS,8aS)-3-(benzyloxy)hexahydro-2H-1,4-methanopyrrolo[3,4-d][1,3]diazepine-2,8(3H)-dione (80 mg, 0.278 mmol) and Pd—C (10% Degussa type 101, 50% water, 34 mg) in MeOH (1.8 mL) was evacuated and backfilled with H$_2$ (3×). After 2.5 h it was filtered through a plug of celite, washed with MeOH and concentrated in vacuo, affording the title compound (40 mg, 74%). LCMS: R$_t$=0.13 min, m/z=198.1 (M+1) Method 2m_acidic.

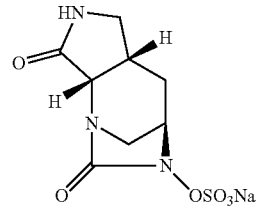

Step 4: Sodium (4R,5aS,8aS)-2,8-dioxohexahydro-2H-1,4-methanopyrrolo[3,4-d][1,3]diazepin-3(4H)-yl sulfate To a slurry of crude (4R,5aS,8aS)-3-hydroxyhexahydro-2H-1,4-methanopyrrolo[3,4-d][1,3]diazepine-2,8(3H)-dione (40.7 mg, 0.206 mmol) in pyridine (2 mL) at 0° C. was added SO$_3$.Py complex (335 mg, 2.064 mmol). After 19 h of vigorous stirring the slurry was filtered and concentrated in vacuo. The crude residue was dissolved in THF:water (1:1, 6 mL) and Amberlite 200 Na-exchange resin (1.5 g) was added. The suspension was stirred for 2 h, whereupon it was filtered, partially concentrated in vacuo, frozen and lyophilized. The resulting solid was subjected to silica gel chromatography (water-acetonitrile, 2-5%), affording the title compound (12.3 mg, 16%, over 2-steps) as an amorphous solid. LCMS: R$_t$=0.25 min, m/z=278.0 (M+1) Method T3_3m_polar; $^1$H NMR (500 MHz, D$_2$O) δ 4.24-4.18 (m, 2H), 3.52 (dd, J=10.7, 6.2 Hz, 1H), 3.33 (d, J=12.3 Hz, 1H), 3.10 (d, J=10.7 Hz, 1H), 2.95 (d, J=12.3 Hz, 1H), 2.81 (p, J=8.5 Hz, 1H), 2.54-2.46 (m, 1H), 1.65 (dd, J=14.7, 9.2 Hz, 1H).

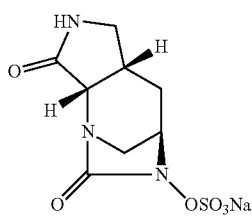

Example 1. Alternate Procedure. Sodium (4R,5aS, 8aS)-2,8-dioxohexahydro-2H-1,4-methanopyrrolo[3,4-d][1,3]diazepin-3(4H)-yl sulfate

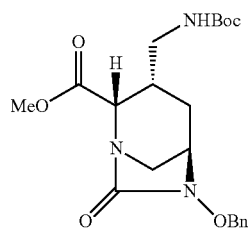 [SMILES: COC(=O)[C@@H]1[C@H](CNC(=O)OC(C)(C)C)C[C@@H]2CN1C(=O)N2OCc1ccccc1]

Step 1: (2S,3S,5R)-methyl 6-(benzyloxy)-3-(((tert-butoxycarbonyl)amino)methyl)-7-oxo-1,6-diazabicyclo[3.2.1]octane-2-carboxylate A stirred mixture of Intermediate C (3 g, 10.41 mmol), 2-((tert-butoxycarbonyl)amino)acetic acid (2.55 g, 14.57 mmol), Ir[df(CF$_3$)ppy]$_2$(dtbpy)PF$_6$ (0.117 g, 0.104 mmol), and potassium phosphate dibasic (2.72 g, 15.61 mmol) in DMF (30.6 mL) was degassed via N$_2$ sparge for 15 min and irradiated with a Kessil H150-Blue LED (fan cooling), under N$_2$ for 92 h. 2-((tert-butoxycarbonyl)amino)acetic acid (2.55 g, 14.57 mmol), potassium phosphate dibasic (2.72 g, 15.61 mmol), and Ir[df(CF$_3$)ppy$_2$(dtbpy)PF$_6$ (0.117 g, 0.104 mmol) were added and the mixture was irradiated with a Kessil H150-Blue LED (fan cooling), under N$_2$ for an additional 20 h. The mixture was diluted with saturated NaHCO$_3$ (aq) and extracted with EtOAc (3×). The combined organic layers were washed with water, brine, dried over Na$_2$SO$_4$, filtered and concentrated under reduced pressure. The crude material was purified by silica gel chromatography (EtOAc-Heptanes, 0-100%) to afford the title compound (352 mg, 8%) as a yellow foam. LC/MS: R$_t$=0.87 min; m/z=420.2 (M+1) Method 2m_acidic; $^1$H NMR (500 MHz, DMSO-d$_6$) δ 7.46-7.42 (m, 2H), 7.42-7.34 (m, 3H), 6.84 (br s, 1H), 4.93 (d, J=4.3 Hz, 2H), 3.88 (d, J=6.7 Hz, 1H), 3.76 (br s, 1H), 3.66-3.65 (m, 3H), 3.21 (d, J=12.0 Hz, 1H), 3.12-3.03 (m, 1H), 2.86-2.78 (m, 2H), 2.14 (br s, 1H), 2.00-1.93 (m, 1H), 1.51 (t, J=12.3 Hz, 1H), 1.34 (s, 9H)

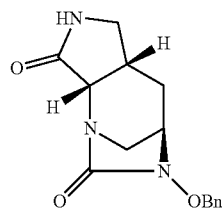 [SMILES: O=C1NC[C@@H]2C[C@@H]3CN(C(=O)N3OCc3ccccc3)[C@H]12]

Step 2: (4R,5aS,8aS)-3-(benzyloxy)hexahydro-2H-1,4-methanopyrrolo[3,4-d][1,3]diazepine-2,8(8aH)-dione To a solution of (2S,3S,5R)-methyl 6-(benzyloxy)-3-(((tert-butoxycarbonyl)amino)methyl)-7-oxo-1,6-diazabicyclo[3.2.1]octane-2-carboxylate (352 mg, 0.839 mmol) in DCM (4.19 mL) was added TFA (1.61 mL, 20.98 mmol), drop-wise. After 90 min it was concentrated in vacuo, dissolved in DCM and reconcentrated (3×). To the residue, dissolved in DCM (5 mL) at 0° C. was added TEA (1.17 mL, 8.39 mmol), after which the cooling bath was removed. After 20 h at rt, the mixture was diluted with saturated NaHCO$_3$ (aq) and extracted with EtOAc (3×). The combined organic layers were washed with water, brine, dried over Na$_2$SO$_4$, filtered and concentrated in vacuo. The crude material was purified by silica gel chromatography (MeOH-DCM, 0-20%), affording the title compound (158 mg, 66%, 2-steps) as a clear film. LC/MS: R$_t$=0.65 min; m/z=288.0 (M+1) Method 2m_acidic; $^1$H NMR (400 MHz, DMSO-d$_6$) δ 7.99 (s, 1H), 7.48-7.33 (m, 5H), 4.99-4.88 (m, 2H), 3.81 (d, J=7.8 Hz, 1H), 3.59 (br s, 1H), 3.32-3.22 (m, 1H), 2.89 (br d, J=11.9 Hz, 1H), 2.75 (d, J=9.8 Hz, 1H), 2.63 (d, J=11.9 Hz, 1H), 2.26-2.17 (m, 1H), 1.38 (ddd, J=14.3, 9.2, 1.9 Hz, 1H)

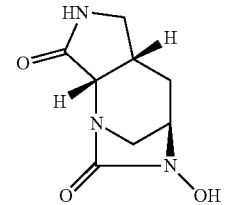

Step 3: (4R,5aS,8aS)-3-hydroxyhexahydro-2H-1,4-methanopyrrolo[3,4-d][1,3]diazepine-2,8(8aH)-dione A slurry of (4R,5aS,8aS)-3-(benzyloxy)hexahydro-2H-1,4-methanopyrrolo[3,4-d][1,3]diazepine-2,8(8aH)-dione (158 mg, 0.550 mmol) and Pd—C (10% Degussa type 101, 50% water, 117 mg, 0.055 mmol) in MeOH:DCM (3:1, 3.67 mL) was evacuated and backfilled with H$_2$. After 2 h, the mixture was filtered through celite and concentrated in vacuo (bath temp <30° C.) to afford the title compound (102 mg, 94%) as an off-white solid. LC/MS: R$_t$=0.12 min; m/z=198.0 (M+1) Method 2m_acidic.

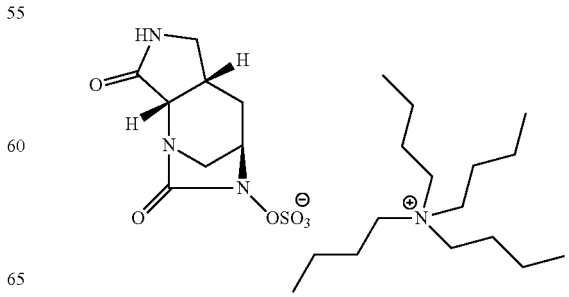

Step 4: Tetrabutylammonium (4R,5aS,8aS)-2,8-dioxohexahydro-2H-1,4-methanopyrrolo[3,4-d][1,3]diazepin-3(4H)-yl sulfate To a solution of crude (4R,5aS,8aS)-3-hydroxyhexahydro-2H-1,4-methanopyrrolo[3,4-d][1,3]diazepine-2,8(8aH)-dione (102 mg, 0.517 mmol) in Pyridine (5.17 mL) was added $SO_3.Py$ (412 mg, 2.59 mmol). After 19 h of vigorous stirring, the mixture was filtered and concentrated in vacuo (bath temp <30° C.). The resulting material was dissolved in $NaH_2PO_4$ (1 M, 10 mL), whereupon tetrabutylammonium hydrogen sulfate (263 mg, 0.776 mmol) was added. After 30 min of stirring it was extracted with IPA:$CHCl_3$ (1:4, 3×). The combined organic layers were dried over $Na_2SO_4$, filtered and concentrated in vacuo (bath temp <30° C.). The crude residue was purified by silica gel chromatography (MeOH-DCM, 0-30%) to afford the title compound (180 mg, 67%) as a white foam. LC/MS: $R_t$=0.13 min; m/z=278 (M+1) Method 2m_acidic; $^1$H NMR (500 MHz, DMSO-$d_6$) δ 7.97 (s, 1H), 3.98 (br s, 1H), 3.81 (d, J=7.8 Hz, 1H), 3.28 (dd, J=6.1, 9.9 Hz, 1H), 3.19-3.13 (m, 8H), 2.98 (br d, J=12.1 Hz, 1H), 2.78 (d, J=9.9 Hz, 1H), 2.65 (d, J=12.1 Hz, 1H), 2.49-2.44 (m, 1H), 2.28-2.19 (m, 1H), 1.63-1.51 (m, 8H), 1.40 (br dd, J=9.3, 12.7 Hz, 1H), 1.31 (sxt, J=7.4 Hz, 8H), 0.93 (t, J=7.3 Hz, 12H)

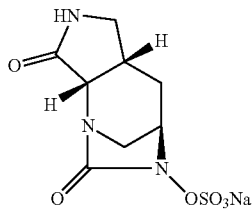

Step 5: Sodium (4R,5aS,8aS)-2,8-dioxohexahydro-2H-1,4-methanopyrrolo[3,4-d][1,3]diazepin-3(4H)-yl sulfate DOWEX 50W×8 hydrogen form 200-400 mesh was conditioned by stirring with NaOH (2 N) for 3 h. The resin was loaded onto a column and washed with water until the pH was ~6. It was then washed with 1:1 water/acetone. tetrabutylammonium (4R,5aS,8aS)-2,8-dioxohexahydro-2H-1,4-methanopyrrolo[3,4-d][1,3]diazepin-3(4H)-yl sulfate (180 mg, 0.347 mmol) was dissolved in 1:1 acetone/water and eluted through the resin with 1:1 acetone/water. The sample was partially concentrated in vacuo (bath temp <30° C.), and lyophilized to afford the title compound (75 mg, 68%) as a white solid. LC/MS: $R_t$=0.25 min; m/z=278.0 (M+1) Method T3_3m_polar; $^1$H NMR (500 MHz, $D_2O$) δ 4.24-4.18 (m, 2H), 3.51 (dd, J=10.7, 6.2 Hz, 1H), 3.33 (br d, J=12.3 Hz, 1H), 3.10 (d, J=10.7 Hz, 1H), 2.95 (d, J=12.3 Hz, 1H), 2.81 (p, J=8.1 Hz, 1H), 2.54-2.46 (m, 1H), 1.65 (dd, J=14.7, 9.2 Hz, 1H).

Alternate Step 5 Procedure: (4R,5aS,8aS)-2,8-dioxohexahydro-2H-1,4-methanopyrrolo[3,4-d][1,3]diazepin-3(4H)-yl hydrogen sulfate To a solution of tetrabutylammonium (4R,5aS,8aS)-2,8-dioxohexahydro-2H-1,4-methanopyrrolo[3,4-d][1,3]diazepin-3(4H)-yl sulfate (6.9 g, 13.30 mmol) in isobutanol (20.8 mL) and water (1.35 mL) at 40° C. was added a solution of sodium 2-ethylhexanoate (4.56 g, 26.6 mmol) in isobutanol (20.8 mL) and water (1.35 mL) via syringe pump at 8 mL/h. The mixture was stirred for 1 h at 40° C. then cooled to rt and stirred overnight, whereupon it was filtered with a Buchner funnel using Whatman qualitative filter paper. The filter cake was washed with isobutanol (3×) and then ice-cold acetone (3×). Vacuum was applied to the funnel with $N_2$ stream over the filter cake for 3 h followed by lyophilization for 3 days, which afforded the title compound (3.05 g, 73%) as a crystalline white solid. LC/MS: $R_t$=0.25 min; m/z=278.0 (M+1) Method T3_3m_polar.

$^1$H NMR (500 MHz, $D_2O$) δ=4.20-4.12 (m, 2H), 3.48 (dd, J=6.2, 10.7 Hz, 1H), 3.33-3.25 (m, 1H), 3.05 (d, J=10.7 Hz, 1H), 2.90 (d, J=12.2 Hz, 1H), 2.82-2.71 (m, 1H), 2.46 (tdd, J=2.8, 8.7, 14.7 Hz, 1H), 1.66-1.56 (m, 1H)

The X-ray powder diffraction spectrum for the sodium salt is shown in FIG. 1.

Instrument: X-Ray Diffractometer (Bruker, model D8)

Source—Cu k α

Step width 0.02°

Voltage 40 kV

Current 40 mA

Time per step 120 seconds

Scan Range 3 to 39°

| Peak | 2theta |
| --- | --- |
| 1 | 8.31 ± 0.2) |
| 2 | 11.66 ± 0.2) |
| 3 | 14.45 ± 0.2) |
| 4 | 16.63 ± 0.2) |
| 5 | 17.64 (± 0.2) |
| 6 | 18.12 ± 0.2) |
| 7 | 18.64 ± 0.2) |
| 8 | 19.51 ± 0.2) |
| 9 | 21.68 ± 0.2) |
| 10 | 23.54 ± 0.2) |
| 11 | 24.32 ± 0.2) |
| 12 | 25.06 (± 0.2) |
| 13 | 27.37 ± 0.2) |
| 14 | 27.86 ± 0.2) |
| 15 | 28.72 ± 0.2) |
| 16 | 31.33 ± 0.2) |
| 17 | 32.60 ± 0.2) |
| 18 | 33.58 ± 0.2) |
| 19 | 34.43 ± 0.2) |
| 20 | 35.40 ± 0.2) |
| 21 | 38.17 (± 0.2) |

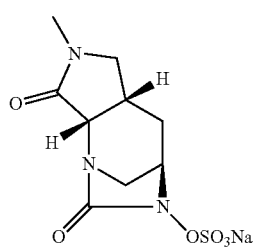

Example 2. Sodium (4R,5aS,8aS)-7-methyl-2,8-dioxohexahydro-2H-1,4-methanopyrrolo[3,4-d][1,3]diazepin-3(4H)-yl sulfate

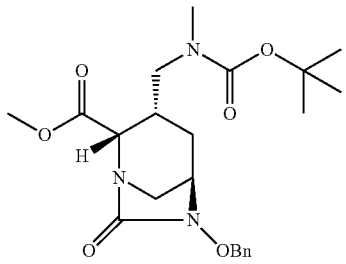 [SMILES: COC(=O)[C@@H]1[C@H](CN(C)C(=O)OC(C)(C)C)C[C@@H]2CN1C(=O)N2OCc1ccccc1]

Step 1: (2S,3S,5R)-methyl 6-(benzyloxy)-3-(((tert-butoxycarbonyl)(methyl)amino)methyl)-7-oxo-1,6-diazabicyclo[3.2.1]octane-2-carboxylate A stirred mixture of Intermediate C (3 g, 10.41 mmol), 2-((tert-butoxycarbonyl)(methyl)amino)acetic acid (2.56 g, 13.53 mmol), Ir[df(CF$_3$)ppy$_2$(dtbpy)PF$_6$ (0.117 g, 0.104 mmol), and potassium phosphate dibasic (2.175 g, 12.49 mmol) in DMF (30 mL) was degassed by bubbling N$_2$ through the suspension for 15 min and then left under an N$_2$ line and irradiated with a Kessil H150-Blue LED (fan cooling) for 48 h. The reaction was diluted with saturated NaHCO$_3$ and extracted with EtOAc (3×). The combined organic layers were washed with water, brine, dried over Na$_2$SO$_4$, filtered and concentrated in vacuo. The crude material was purified by silica gel chromatography (EtOAc-Heptanes, 0-100%) to afford an orange foam (233 mg). This material was repurified by silica gel chromatography (EtOAc-Heptanes, 0-70%) affording the title compound (140 mg, 3%) as a yellow solid. LC/MS: R$_f$=0.92 min; m/z=434.1 (M+1) Method 2m_acidic; $^1$H NMR (500 MHz, DMSO-d$_6$) δ 7.46-7.42 (m, 2H), 7.41-7.33 (m, 3H), 4.98-4.91 (m, 2H), 3.88-3.81 (m, 1H), 3.78 (br s, 1H), 3.68 (br s, 3H), 3.26-3.03 (m, 2H), 2.84 (br d, J=11.6 Hz, 1H), 2.67 (s, 3H), 1.97-1.88 (m, 1H), 1.62 (br t, J=12.6 Hz, 1H), 1.34 (br s, 9H)

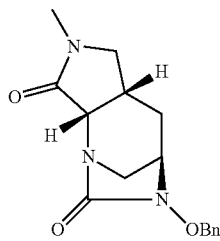 [SMILES: CN1C[C@@H]2C[C@@H]3CN(C(=O)N3OCc3ccccc3)[C@@H]2C1=O]

Step 2: (2S,3S,5R)-methyl 6-(benzyloxy)-3-((methylamino)methyl)-7-oxo-1,6-diazabicyclo[3.2.1]octane-2-carboxylate To a stirred solution of (2S,3S,5R)-methyl 6-(benzyloxy)-3-(((tert-butoxycarbonyl)(methyl)amino)methyl)-7-oxo-1,6-diazabicyclo[3.2.1]octane-2-carboxylate (140 mg, 0.323 mmol) in DCM (1.6 mL), TFA (0.622 mL, 8.07 mmol) was added drop wise at rt under N$_2$. The reaction was stirred at rt for 90 min and then concentrated and coevaporated with DCM (3×). The residue was dissolved in DCM (2 mL) and cooled to 0° C. TEA (0.450 mL, 3.23 mmol) was added, the cooling bath removed and the reaction stirred at rt for 90 min. The reaction was diluted with saturated NaHCO$_3$ and extracted with EtOAc (3×). The combined organic layers were washed with water, brine, dried over Na$_2$SO$_4$, filtered and concentrated in vacuo. The crude material was purified by silica gel chromatography (MeOH-DCM, 0-20%) to afford the title compound (86 mg, 88%) as a clear film. LC/MS: R$_f$=0.46 min; m/z=301.9 (M+1) Method 2m_acidic; $^1$H NMR (400 MHz, DMSO-d$_6$) δ 7.50-7.32 (m, 5H), 5.03-4.86 (m, 2H), 3.86 (d, J=7.9 Hz, 1H), 3.60 (br s, 1H), 3.39-3.34 (m, 1H), 2.93-2.83 (m, 2H), 2.76 (s, 3H), 2.57 (d, J=11.9 Hz, 1H), 2.49-2.42 (m, 1H), 2.32-2.18 (m, 1H), 1.38 (ddd, J=14.3, 9.0, 1.9 Hz, 1H)

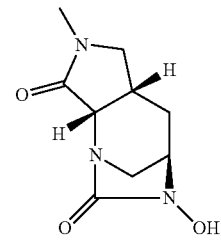

Step 3: (4R,5aS,8aS)-3-hydroxy-7-methylhexahydro-2H-1,4-methanopyrrolo[3,4-d][1,3]diazepine-2,8(8aH)-dione (2S,3S,5R)-methyl 6-(benzyloxy)-3-((methylamino)methyl)-7-oxo-1,6-diazabicyclo[3.2.1]octane-2-carboxylate (143 mg, 0.475 mmol) was dissolved in methanol (2.4 mL) and Pd—C (10%, Degussa type 101, 50% water, 101 mg, 0.047 mmol) was added. The mixture was evacuated under vacuum and backfilled with H$_2$. After 1 h of stirring, the mixture was filtered through celite and concentrated in vacuo (bath temp <30° C.) to afford the title compound (63 mg, 63%) as a white solid. LC/MS: R$_f$=0.11 min; m/z=211.9 (M+1) Method 2m_acidic.

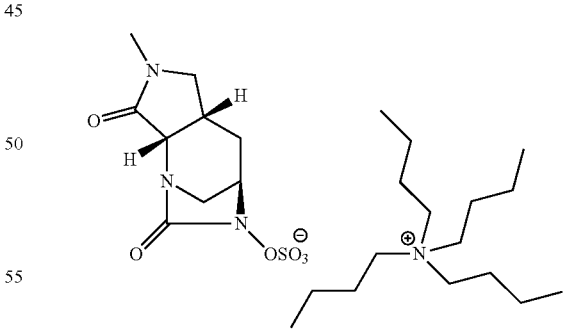

Step 4: tetrabutylammonium (4R,5aS,8aS)-7-methyl-2,8-dioxohexahydro-2H-1,4-methanopyrrolo[3,4-d][1,3]diazepin-3(4H)-yl sulfate (4R,5aS,8aS)-3-hydroxy-7-methylhexahydro-2H-1,4-methanopyrrolo[3,4-d][1,3]diazepine-2,8(8aH)-dione (63 mg, 0.298 mmol) was dissolved in Pyridine (2.9 mL) and SO$_3$.pyridine (237 mg, 1.49 mmol) was added. The reaction was stirred at rt for 20 h. The reaction was filtered through a disposable plastic filter and concentrated under reduced pressure (bath temp <30° C.). This material was dissolved in NaH₂PO₄ (1 M, 10 mL) and tetrabutylammonium hydrogen sulfate (152 mg, 0.447 mmol) was added. After stirring for 30 min at rt it was extracted with EtOAc (4×). The combined organic layers were washed with brine, dried over Na₂SO₄, filtered and concentrated in vacuo. The aqueous was further extracted with 20% IPA in CHCl₃ (2×), dried over sodium sulfate and concentrated in vacuo (bath temp <30° C.). The combined organic material was purified by silica gel chromatography (MeOH-DCM, 0-30%) to afford the title compound (62 mg, 39%) as a clear film. LC/MS: $R_t$=0.13 min; m/z=291.9 (M+1) Method 2m_acidic; $^1$H NMR (400 MHz, CDCl₃) δ=4.34 (br s, 1H), 4.04 (br d, J=7.3 Hz, 1H), 3.44 (dd, J=10.0, 5.6 Hz, 1H), 3.34 (br d, J=2.6 Hz, 1H), 3.28 (br dd, J=10.3 Hz, 5.1 Hz, 8H), 2.97-2.91 (m, 4H), 2.80 (d, J=12.0 Hz, 1H), 2.75-2.61 (m, 2H), 1.74-1.60 (m, 9H), 1.44 (sxt, J=7.4 Hz, 8H), 1.00 (t, J=7.3 Hz, 12H).

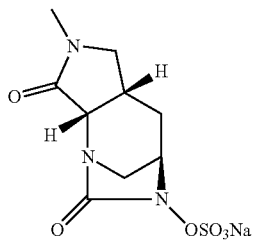

Step 5: sodium (4R,5aS,8aS)-7-methyl-2,8-dioxo-hexahydro-2H-1,4-methanopyrrolo[3,4-d][1,3]diazepin-3(4H)-yl sulfate DOWEX 50W×8 hydrogen form 200-400 mesh was conditioned by stirring with NaOH (2 N) for 3 h. The resin was loaded onto a glass column and washed with water until the pH was ~6. It was then washed with water:acetone (1:1). Tetrabutylammonium (4R,5aS,8aS)-7-methyl-2,8-dioxo-hexahydro-2H-1,4-methanopyrrolo[3,4-d][1,3]diazepin-3 (4H)-yl sulfate (62 mg, 0.12 mmol) was dissolved in 1:1 acetone:water and passed down the column with acetone: water (1:1). The sample was partially concentrated in vacuo (bath temp <30° C.) then lyophilized to afford the title compound (32 mg, 83%) as a white powder. LC/MS: $R_t$=0.48 min; m/z=291.8 (M+1) Method T3_3m_polar; $^1$H NMR (500 MHz, D₂O) δ=4.20-4.15 (m, 2H), 3.60 (dd, J=10.6, 6.4 Hz, 1H), 3.30 (dddd, J=12.3, 4.0, 2.7, 1.3 Hz, 1H), 3.13 (d, J=10.4 Hz, 1H), 2.90 (s, 3H), 2.86 (d, J=12.1 Hz, 1H), 2.77-2.69 (m, 1H), 2.49 (tdd, J=14.8, 8.8, 3.0 Hz, 1H), 1.59 (ddd, J=14.8, 8.9, 2.0 Hz, 1H).

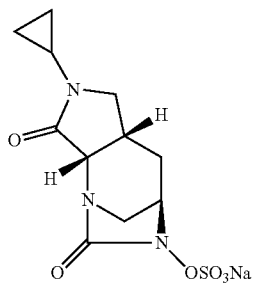

Example 3. Sodium (4R,5aS,8aS)-7-cyclopropyl-2,8-dioxohexahydro-2H-1,4-methanopyrrolo[3,4-d][1,3]diazepin-3(4H)-yl sulfate

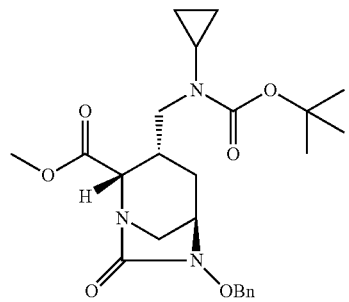 [SMILES: COC(=O)[C@@H]1[C@H](CN(C(=O)OC(C)(C)C)C2CC2)C[C@@H]2CN1C(=O)N2OCc1ccccc1]

Step 1: (2S,3S,5R)-methyl 6-(benzyloxy)-3-(((tert-butoxycarbonyl) (cyclopropyl)amino)methyl)-7-oxo-1,6-diazabicyclo[3.2.1]octane-2-carboxylate A stirred mixture of Intermediate C (4 g, 13.87 mmol), 2-((tert-butoxycarbonyl)(cyclopropyl)amino)acetic acid (3.88 g, 18.04 mmol), Ir[df(CF₃)ppy₂(dtbpy)]PF₆ (0.156 g, 0.139 mmol), and potassium phosphate dibasic (2.90 g, 16.65 mmol) in DMF (40 mL) was degassed via N₂ sparge for 15 min. The mixture was irradiated under N₂ with a Kessil H150-Blue LED (fan cooling) for 42 h, whereupon it was was diluted with saturated NaHCO₃, filtered and extracted with EtOAc (3×). The combined organic layers were washed with water, brine, dried over Na₂SO₄, filtered and concentrated in vacuo. The crude residue was purified by silica gel chromatography (EtOAc-Heptanes, 0-100%). This material was repurified 2 more times by silica gel chromatography (EtOAc-Heptanes, 0-100% then EtOAc-Heptanes, 0-70%) affording the title compound (190 mg, 3% Yield) as a clear film. LC/MS: $R_t$=0.99 min; m/z=460.2 (M+1) Method 2m_acidic; $^1$H NMR (400 MHz, CDCl₃) δ=7.45-7.34 (m, 5H), 5.05 (d, J=11.5 Hz, 1H), 4.89 (d, J=11.5 Hz, 1H), 4.09 (d, J=6.5 Hz, 1H), 3.74 (s, 3H), 3.37-3.25 (m, 2H), 3.17-3.07 (m, 1H), 2.92-2.83 (m, 1H), 2.64-2.52 (m, 1H), 2.44-2.35 (m, 1H), 2.09-1.98 (m, 1H), 1.68 (t, J=12.7 Hz, 1H), 1.58-1.52 (m, 1H), 1.44-1.39 (m, 9H), 0.80-0.66 (m, 2H), 0.59-0.46 (m, 2H)

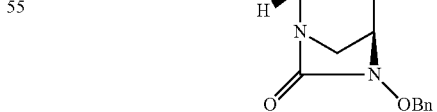

Step 2: (4R,5aS,8aS)-3-(benzyloxy)-7-cyclopropyl-hexahydro-2H-1,4-methanopyrrolo[3,4-d][1,3]diazepine-2,8(8aH)-dione To a stirred solution of (2S,3S,5R)-methyl 6-(benzyloxy)-3-(((tert-butoxycarbonyl)(cyclopropyl)amino)methyl)-7- oxo-1,6-diazabicyclo[3.2.1]octane-2-carboxylate (190 mg, 0.413 mmol) dissolved in DCM (4.1 mL), TFA (0.796 mL, 10.34 mmol) was added drop-wise at rt under $N_2$. The solution was stirred at rt for 90 min and then concentrated in vacuo, diluted with DCM and reconcentrated (3×). The residue was dissolved in DCM (2 mL) and cooled to 0° C. TEA (0.576 mL, 4.13 mmol) was added and it was stirred for 18 h at rt. The solution was concentrated under reduced pressure and the crude material was purified by silica gel chromatography (MeOH-DCM, 0-20%), affording the title compound (103 mg, 76%) as a clear film. LC/MS: $R_t$=0.69 min; m/z=328.0 (M+1) Method 2m_acidic; $^1$H NMR (500 MHz, DMSO-$d_6$) δ=7.46-7.42 (m, 2H), 7.41-7.33 (m, 3H), 4.97-4.89 (m, 2H), 3.87 (d, J=7.8 Hz, 1H), 3.59 (br s, 1H), 3.31-3.27 (m, 1H), 2.91-2.85 (m, 1H), 2.76 (d, J=9.8 Hz, 1H), 2.66 (tt, J=7.5, 4.1 Hz, 1H), 2.56 (d, J=11.9 Hz, 1H), 2.42 (dd, J=8.5, 6.1 Hz, 1H), 2.19 (ddt, J=14.3, 8.5, 3.0 Hz, 1H), 1.31 (ddd, J=14.3, 9.2, 1.9 Hz, 1H), 0.78-0.68 (m, 2H), 0.66-0.55 (m, 2H).

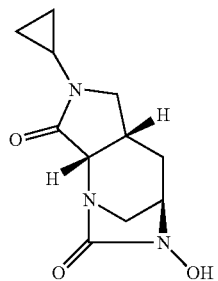 [SMILES: O=C1[C@@H]2[C@@H](C[C@@H]3CN2C(=O)N3O)CN1C1CC1]

Step 3: (4R,5aS,8aS)-7-cyclopropyl-3-hydroxyhexahydro-2H-1,4-methanopyrrolo[3,4-d][1,3]diazepine-2,8(8aH)-dione (4R,5aS,8aS)-3-(benzyloxy)-7-cyclopropylhexahydro-2H-1,4-methanopyrrolo[3,4-d][1,3]diazepine-2,8(8aH)-dione (103 mg, 0.315 mmol) was dissolved in MeOH (3.2 mL) and Pd—C (10% Degussa type 101, 50% water, 67.0 mg, 0.031 mmol) was added. The mixture was degassed in vacuo and backfilled with $H_2$. After stirring for 40 min, it was filtered through celite and concentrated in vacuo (bath temp <30° C.) to afford the title compound (75 mg, 100%) as a white solid. LC/MS: $R_t$=0.54 min; m/z=238.0 (M+1) Method 2m_acidic.

Step 4: Tetrabutylammonium (4R,5aS,8aS)-7-cyclopropyl-2,8-dioxohexahydro-2H-1,4-methanopyrrolo[3,4-d][1,3]diazepin-3(4H)-yl sulfate To a solution of (4R,5aS,8aS)-7-cyclopropyl-3-hydroxyhexahydro-2H-1,4-methanopyrrolo[3,4-d][1,3]diazepine-2,8(8aH)-dione (75 mg, 0.316 mmol) in pyridine (3.16 mL) was added $SO_3$.pyridine (151 mg, 0.948 mmol). After stirring for 20 h, the slurry was filtered and concentrated in vacuo (bath temp <30° C.). The crude residue was dissolved in saturated $NaH_2PO_4$ (10 mL) and washed with EtOAc. To the aqueous layer was added tetrabutylammonium hydrogen sulfate (161 mg, 0.474 mmol). After stirring for 45 min it was extracted with DCM (4×), dried over $Na_2SO_4$, filtered and concentrated in vacuo (bath temp <30° C.). The crude residue was purified via silica gel chromatography (Acetone-DCM, 0-100%) to afford 121 mg of a clear film. LC/MS: $R_t$=0.14 min; m/z=318.0 (M+1) Method 2m_acidic; $^1$H NMR (400 MHz, DMSO-$d_6$) δ=3.93 (br s, 1H), 3.87 (d, J=7.8 Hz, 1H), 3.34-3.29 (m, 1H), 3.19-3.13 (m, 8H), 2.99-2.94 (m, 1H), 2.78 (d, J=9.7 Hz, 1H), 2.68 (tt, J=7.4, 4.2 Hz, 1H), 2.57 (d, J=11.9 Hz, 1H), 2.46-2.36 (m, 1H), 2.26-2.17 (m, 1H), 1.61-1.52 (m, 8H), 1.35-1.26 (m, 9H), 0.93 (t, J=7.3 Hz, 12H), 0.78-0.69 (m, 2H), 0.66-0.57 (m, 2H).

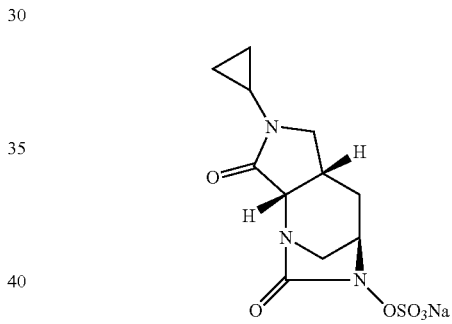

Step 5: Sodium (4R,5aS,8aS)-7-cyclopropyl-2,8-dioxohexahydro-2H-1,4-methanopyrrolo[3,4-d][1,3]diazepin-3(4H)-yl sulfate DOWEX 50W×8 hydrogen form 200-400 mesh was conditioned by stirring with NaOH (2 N) for 3 h. The resin was loaded onto a glass column and washed with water (until pH=6) followed by water:acetone (1:1). A solution of tetrabutylammonium (4R,5aS,8aS)-7-cyclopropyl-2,8-dioxohexahydro-2H-1,4-methanopyrrolo[3,4-d][1,3]diazepin-3(4H)-yl sulfate (121 mg, 0.217 mmol) in water:acetone (1:1) was loaded onto and passed through the column, eluting with water:acetone (1:1). The sample was concentrated in vacuo (bath temp <30° C.) and lyophilized, affording the title compound (51 mg, 66% Yield) as a white powder. LC/MS: $R_t$=0.36 min; m/z=318.0 (M+1) Method 2m_acidic; $^1$H NMR (500 MHz, $D_2O$) δ 4.20-4.14 (m, 2H), 3.55 (dd, J=10.6, 6.1, Hz, 1H), 3.32-3.26 (m, 1H), 3.09 (d, J=10.6 Hz, 1H), 2.83 (d, J=12.3 Hz, 1H), 2.73-2.65 (m, 2H), 2.50-2.42 (m, 1H), 1.51 (dd, J=14.6, 9.1 Hz, 1H), 0.90-0.74 (m, 3H), 0.71-0.63 (m, 1H).

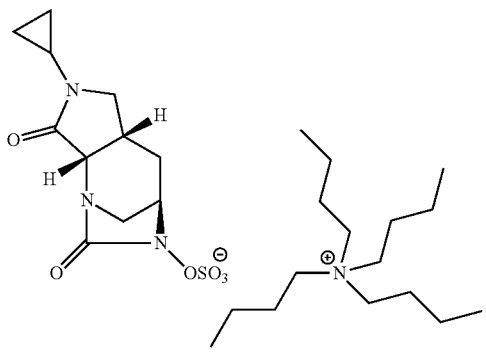

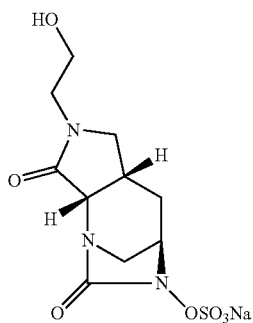

Example 4. Sodium (4R,5aS,8aS)-7-(2-hydroxyethyl)-2,8-dioxohexahydro-2H-1,4-methanopyrrolo[3,4-d][1,3]diazepin-3(4H)-yl sulfate

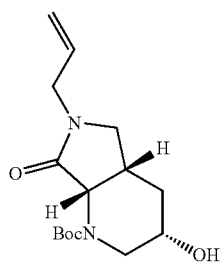 [SMILES: C=CCN1C[C@@H]2C[C@H](O)CN(C(=O)OC(C)(C)C)[C@@H]2C1=O]

Step 1: tert-butyl (3S,4aS,7aS)-6-allyl-3-hydroxy-7-oxooctahydro-1H-pyrrolo[3,4-b]pyridine-1-carboxylate To a soln of tert-butyl (3S,4aS,7aS)-3-hydroxy-7-oxooctahydro-1H-pyrrolo[3,4-b]pyridine-1-carboxylate (1.50 g, 5.62 mmol) in DMF (56 mL) at 0° C. was added Potassium tert-butoxide (1 M in THF, 5.6 ml, 5.6 mmol). After 5 min the cold bath was removed and it was allowed to stir at rt for 30 min then cooled to 0° C., whereupon allylbromide (490 μL, 5.66 mmol) was added drop-wise. The cold bath was removed after 5 min and after an additional 2 h at rt, it was concentrated in vacuo and purified directly via silica gel chromatography (ethylacetate-heptane, 0-100%) to afford the title compound (1.688 g, 81%) as a white solid. LC/MS: $R_t$=0.70 min; m/z=297.1 (M+1) Method 2m_acidic; $^1$H NMR (500 MHz, DMSO-$d_6$)* δ=5.72 (ddt, J=16.4, 11.1, 5.9 Hz, 1H), 5.23-5.15 (m, 2H), 4.96 (s, 1H), 4.77 (d, J=7.1 Hz, 0.5H), 4.62 (d, J=7.1 Hz, 0.5H), 3.97-3.85 (m, 1.5H), 3.85-3.75 (m, 1H), 3.71 (dd, J=15.3, 6.3 Hz, 0.5H), 3.49-3.42 (m, 1H), 2.83-2.77 (m, 1H), 2.50-2.40 (m, 1H), 2.14 (t, J=11.6 Hz, 0.5H), 2.03-1.91 (m, 1.5H), 1.42 (s, 4.5H), 1.38 (s, 4.5H) 0.96 (p, J=12.1 Hz, 1H). *Reported as a mixture of rotamers.

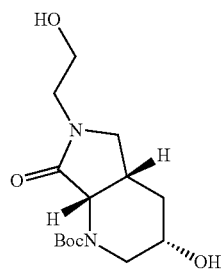 [SMILES: CC(C)(C)OC(=O)N1C[C@@H](O)C[C@H]2CN(CCO)C(=O)[C@H]21]

Step 2: tert-butyl (3S,4aS,7aS)-3-hydroxy-6-(2-hydroxyethyl)-7-oxooctahydro-1H-pyrrolo[3,4-b]pyridine-1-carboxylate A solution of tert-butyl (3S,4aS,7aS)-6-allyl-3-hydroxy-7-oxooctahydro-1H-pyrrolo[3,4-b]pyridine-1-carboxylate (2.72 g, 9.18 mmol) in DCM (92 ml) at −78° C. was sparged with $O_3$ for 30 min. It was then purged by bubbling $O_2$ for an additional 20 min at −78° C. To the clear soln was added dimethylsulfide (6.74 ml, 92 mmol) and it was warmed to rt and stirred for 30 min. It was cooled to 0° C. and MeOH (18 mL) was added followed by sodium borohydride (694 mg, 18.4 mmol) then allowed to slowly warm to rt. After 14 h at rt it was cooled to 0° C. and saturated $NH_4Cl$ (aq, 10 mL) was added. After 20 min at rt it was concentrated in vacuo followed by addition of MeOH and reconcentrated. The residue was taken up in MeOH, filtered then reconcentrated. Tolene was added and the slurry was sonicated then reconcentrated. LCMS: $R_t$=0.40 min; m/z=301.4 (M+1) Method 2m_acidic.

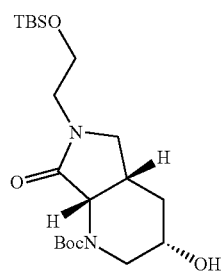 [SMILES: CC(C)(C)OC(=O)N1C[C@@H](O)C[C@H]2CN(CCO[Si](C)(C)C(C)(C)C)C(=O)[C@H]21]

Step 3: tert-butyl (3S,4aS,7aS)-6-(2-((tert-butyldimethylsilyl)oxy)ethyl)-3-hydroxy-7-oxooctahydro-1H-pyrrolo[3,4-b]pyridine-1-carboxylate A soln of tert-butyl (3S,4aS,7aS)-3-hydroxy-6-(2-hydroxyethyl)-7-oxooctahydro-1H-pyrrolo[3,4-b]pyridine-1-carboxylate (9.18 mmol) in pyridine (18 ml) was added TBS-Cl (1.384 g, 9.18 mmol). After stirring for 24 h at rt it was concentrated in vacuo and taken up in EtOAc and washed with water. The aqueous layer was extracted with EtOAc (2×) and the combined organic layers were washed with brine, dried over $Na_2SO_4$, filtered and concentrated in vacuo. The crude residue was purified via silica gel chromatography, affording the title compound (2.433 g, 64% 3-steps) as a white solid. LCMS: $R_t$=0.89 min; m/z=415.4 (M+1) Method 2m_acidic.

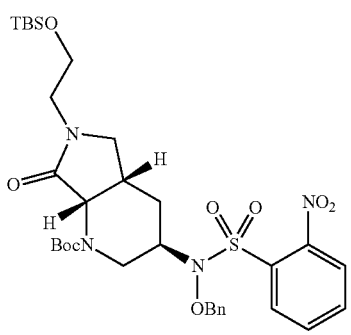 [SMILES: CC(C)(C)OC(=O)N1C[C@H](N(OCc2ccccc2)S(=O)(=O)c2ccccc2[N+](=O)[O-])C[C@H]2CN(CCO[Si](C)(C)C(C)(C)C)C(=O)[C@H]21]

Step 4: tert-butyl (3R,4aS,7aS)-3-((N-(benzyloxy)-2-nitrophenyl)sulfonamido)-6-(2-((tert-butyldimethylsilyl)oxy)ethyl)-7-oxooctahydro-1H-pyrrolo[3,4-b]pyridine-1-carboxylate To a solution of tert-butyl (3S,4aS,7aS)-6-(2-((tert-butyldimethylsilyl)oxy)ethyl)-3-hydroxy-7-oxooctahydro-1H-pyrrolo[3,4-b]pyridine-1-carboxylate (2.411 g, 5.82 mmol), N-(benzyloxy)-2-nitrobenzenesulfonamide (2.160 g, 7.01 mmol) and triphenylphosphine (1.830 g, 6.98 mmol) in THF (65 ml) at −17° C. was added DIAD (1.40 ml, 6.98 mmol) as a soln in THF (10 mL), drop-wise. It was allowed to slowly warm to rt and stir for 18 h then concentrated in vacuo and purified directly via silica gel chromatography, affording the title compound (1.785 g, 44% yield) as a white solid. LCMS: $R_t$=1.15 min; m/z=705.4 (M+1) Method 2m_acidic.

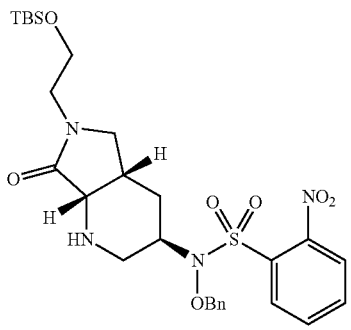 [SMILES: CC(C)(C)[Si](C)(C)OCCN1C[C@@H]2C[C@@H](N(OCc3ccccc3)S(=O)(=O)c3ccccc3[N+](=O)[O-])CN[C@@H]2C1=O]

Step 4: N-(benzyloxy)-N-((3R,4aS,7aS)-6-(2-((tert-butyldimethylsilyl)oxy)ethyl)-7-oxooctahydro-1H-pyrrolo[3,4-b]pyridin-3-yl)-2-nitrobenzenesulfonamide To a flask charged with zinc(II) bromide (1.21 g, 5.37 mmol, dried at 200° C. for 3 h, was added a solution of tert-butyl (3R,4aS,7aS)-3-((N-(benzyloxy)-2-nitrophenyl)sulfonamido)-6-(2-((tert-butyldimethylsilyl)oxy)ethyl)-7-oxooctahydro-1H-pyrrolo[3,4-b]pyridine-1-carboxylate (1.79 g, 2.53 mmol) in DCM (8.5 mL). After stirring at rt for 18 h, it was diluted with DCM and quenched with saturated NaHCO$_3$. Upon cessation of bubbling, the layers were separated and the aqueous was extracted with DCM (3×).

The combined organic layers were dried over Na$_2$SO$_4$, filtered and concentrated in vacuo, resulting in a white foam. LCMS: $R_t$=0.94 min; m/z=605.3 (M+1) Method 2m_acidic.

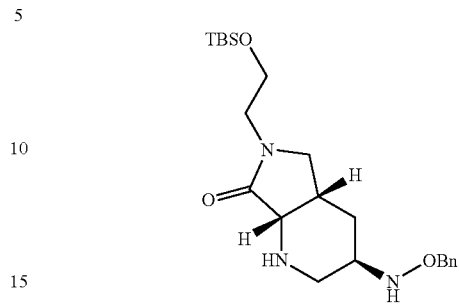

Step 5: (3R,4aS,7aS)-3-((benzyloxy)amino)-6-(2-((tert-butyldimethylsilyl)oxy)ethyl)octahydro-7H-pyrrolo[3,4-b]pyridin-7-one To a slurry of N-(benzyloxy)-N-((3R,4aS,7aS)-6-(2-((tert-butyldimethylsilyl)oxy)ethyl)-7-oxooctahydro-1H-pyrrolo[3,4-b]pyridin-3-yl)-2-nitrobenzenesulfonamide (1.53 g, 2.53 mmol) and K$_2$CO$_3$ (1.753 g, 12.68 mmol) in ACN (25 mL) was added thiophenol (1.343 ml, 12.65 mmol). After 22 h it was filtered and concentrated in vacuo. The crude residue was purified via silica gel chromatography, affording the title compound (919 mg, 87%, 2-steps) as an off-white foam. LCMS: $R_t$=0.82 min; m/z=420.4 (M+1) Method 2m_acidic.

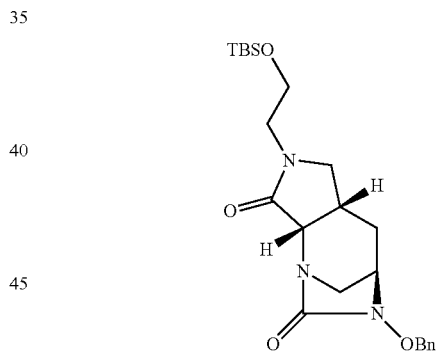

Step 6: (4R,5aS,8aS)-3-(benzyloxy)-7-(2-((tert-butyldimethylsilyl)oxy)ethyl)-hexahydro-2H-1,4-methanopyrrolo[3,4-d][1,3]diazepine-2,8(3H)-dione To a solution of (3R,4aS,7aS)-3-((benzyloxy)amino)-6-(2-((tert-butyldimethylsilyl)oxy)ethyl)octahydro-7H-pyrrolo[3,4-b]pyridin-7-one (919 mg, 2.19 mmol) and DIPEA (1.2 mL, 6.87 mmol) in acetonitrile (68.4 mL) at 0° C. was added phosgene (15-20% in toluene, 1.60 mL, 2.24 mmol) as a solution in acetonitrile (10 mL) at a rate of 8 mL/h. It was allowed to slowly raise to rt. After 20 h it was concentrated in vacuo, partitioned between EtOAc/HCl (aq, 0.2 M) and the phases were separated. The aqueous layer was extracted with EtOAc (2×) and the combined organic layers were washed with brine, saturated NaHCO$_3$, dried over Na$_2$SO$_4$/MgSO$_4$, filtered and concentrated in vacuo. The crude residue was purified via silica gel chromatography, affording the title compound (549 mg, 56%) as a white foam. LCMS: $R_t$=0.95 min; m/z=446.4 (M+1) Method 2m_acidic.

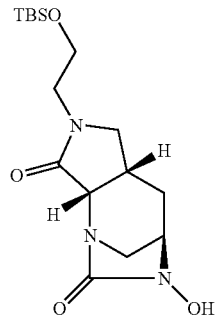 [SMILES: CC(C)(C)[Si](C)(C)OCCN1C[C@@H]2C[C@@H]3CN(C(=O)N3O)[C@@H]2C1=O]

Step 7: (4R,5aS,8aS)-7-(2-((tert-butyldimethylsilyl)oxy)ethyl)-3-hydroxyhexahydro-2H-1,4-methanopyrrolo[3,4-d][1,3]diazepine-2,8(3H)-dione A slurry of (4R,5aS,8aS)-3-(benzyloxy)-7-(2-((tert-butyldimethylsilyl)oxy)ethyl)hexahydro-2H-1,4-methanopyrrolo[3,4-d][1,3]diazepine-2,8(3H)-dione (110 mg, 0.247 mmol) and Pd—C (10% Degussa type 101, 50% water, 25 mg, 0.012 mmol) in MeOH (2.5 mL) was degassed and backfilled with $H_2$ (3×). After 3 h of vigorous stirring the slurry was purged with $N_2$, filtered through celite and concentrated in vacuo. Toluene was added and it was sonicated then reconcentrated. Assumed quantitative yield. LCMS: $R_t$=0.71 min; m/z=356.4 (M+1) Method 2m_acidic.

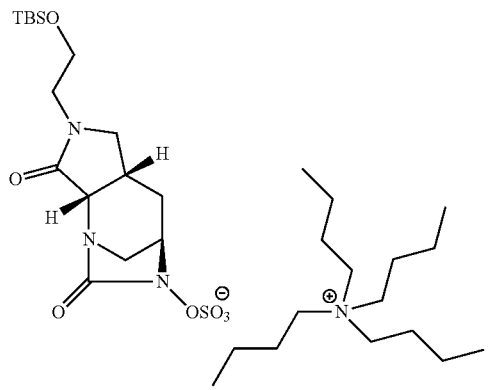

Step 8: Tetrabutylammonium (4R,5aS,8aS)-7-(2-((tert-butyldimethylsilyl)oxy)ethyl)-2,8-dioxohexahydro-2H-1,4-methanopyrrolo[3,4-d][1,3]diazepin-3(4H)-yl sulfate To a solution of (4R,5aS,8aS)-7-(2-((tert-butyldimethylsilyl)oxy)ethyl)-3-hydroxyhexahydro-2H-1,4-methanopyrrolo[3,4-d][1,3]diazepine-2,8(3H)-dione (0.247 mmol) in pyridine (1.6 mL) was added $SO_3$.Py (197 mg, 1.24 mmol). After stirring for 17 h at rt the mixture was concentrated in vacuo and slurried in DCM then filtered and reconcentrated in vacuo. The resulting solid was dissolved in $NaH_2PO_4$ (1 M aq, 20 mL), whereupon tetrabutylammonium hydrogen sulfate (131 mg, 0.386 mmol) was added. After stirring for 45 min it was extracted with DCM (4×) and the combined organic layers were dried over $Na_2SO_4$, filtered and concentrated in vacuo. The crude residue was purified via silica gel chromatography (MeOH-DCM, 0-20%) to afford the title compound (56 mg, 34%, 3-steps) as an off-white foam. LCMS: $R_t$=0.81 min; m/z=436.3 (M+1) Method 2m_acidic.

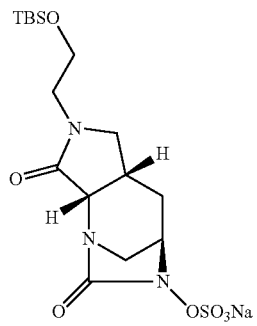

Step 9: Sodium (4R,5aS,8aS)-7-(2-((tert-butyldimethylsilyl)oxy)ethyl)-2,8-dioxohexahydro-2H-1,4-methanopyrrolo[3,4-d][1,3]diazepin-3(4H)-yl sulfate DOWEX 50W×8 hydrogen form 200-400 mesh was conditioned by stirring with NaOH (2 N) for 3 h. The resin was loaded onto a glass column and washed with water (until pH=6) followed by water:acetone (1:1). A solution of tetrabutylammonium (4R,5aS,8aS)-7-(2-((tert-butyldimethylsilyl)oxy)ethyl)-2,8-dioxohexahydro-2H-1,4-methanopyrrolo[3,4-d][1,3]diazepin-3(4H)-yl sulfate (56 mg, 0.083 mmol) in water:acetone (1:1) was loaded onto and passed through the column, eluting with water:acetone (1:1). The sample was concentrated in vacuo (bath temp <30° C.) and lyophilized, affording the title compound (36 mg, 95% Yield) as a white powder. LCMS: $R_t$=0.84 min; m/z=436.3 (M+1) Method 2m_acidic.

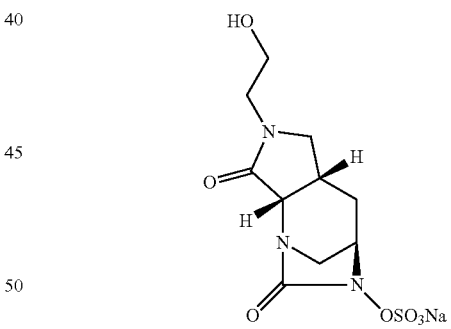

Step 10: Sodium (4R,5aS,8aS)-7-(2-hydroxyethyl)-2,8-dioxohexahydro-2H-1,4-methanopyrrolo[3,4-d][1,3]diazepin-3(4H)-yl sulfate To a slurry of sodium (4R,5aS,8aS)-7-(2-((tert-butyldimethylsilyl)oxy)ethyl)-2,8-dioxohexahydro-2H-1,4-methanopyrrolo[3,4-d][1,3]diazepin-3(4H)-yl sulfate (36 mg, 0.079 mmol) in acetonitrile (790 μL) was added triethylamine trihydrofluoride (13.07 μl, 0.079 mmol), drop-wise and the resulting solution was heated to 45° C. for 3 h. Additional triethylamine trihydrofluoride (13.07 μl, 0.079 mmol) was added and it was heated to 45° C. for 2 h then concentrated in vacuo. The crude residue was taken up in phosphate buffer (pH=6) and purified by reverse phase prep HPLC (T3, Atlantis column, 30×100 mm, 5 µm, C18 column; ACN-water with 3.75 mmol NH₄OAC buffer, 20-60 mL/min), affording the title compound (13.9 mg) as a white powder. LCMS: R$_t$=0.34 min; m/z=322.2 (M+1) Method T3_3m_polar. ¹H NMR (500 MHz, D₂O) δ 4.8 (d, J=8.0 Hz, 1H), 4.14 (s, 1H), 3.69 (t, J=5.4 Hz, 2H), 3.61 (dd, J=10.7, 6.3 Hz, 1H), 3.49-3.37 (m, 2H), 3.29-3.22 (m, 1H), 3.17-3.14 (m, 1H), 2.84 (d, J=12.2 Hz, 1H), 2.75-2.67 (m, 1H), 2.45 (ddt, J=14.7, 8.7, 3.0 Hz, 1H), 1.54 (ddd, J=14.8, 9.0, 2.0 Hz, 1H).

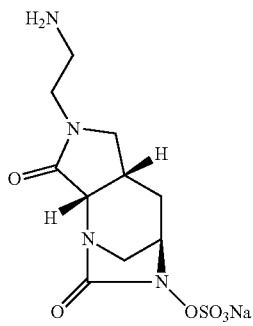

Example 5. (4R,5aS,8aS)-7-(2-aminoethyl)-2,8-dioxohexahydro-2H-1,4-methanopyrrolo[3,4-d][1,3]diazepin-3(4H)-yl hydrogen sulfate

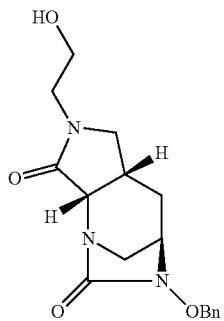 [SMILES: O=C1[C@@H]2[C@@H](C[C@@H]3CN2C(=O)N3OCc2ccccc2)CN1CCO]

Step 1: (4R,5aS,8aS)-3-(benzyloxy)-7-(2-hydroxyethyl)hexahydro-2H-1,4-methanopyrrolo[3,4-d][1,3]diazepine-2,8(3H)-dione To a soln of (4R,5aS,8aS)-3-(benzyloxy)-7-(2-((tert-butyldimethylsilyl)oxy)ethyl)hexahydro-2H-1,4-methanopyrrolo[3,4-d][1,3]diazepine-2,8(3H)-dione (530 mg, 1.19 mmol) in THF (12 mL) at 0° C. was added TBAF (1.2 mL, 1.20 mmol). After 1 h at 0° C. it was concentrated in vacuo, partitioned between EtOAc/water and the phases were separated. The aqueous layer was extracted with EtOAc (2×) and the combined organic layers were washed with brine, dried over Na₂SO₄/MgSO₄, filtered and concentrated in vacuo. The crude residue was purified by silica gel chromatography (MeOH-DCM, 0-7%) to afford the title compound (268 mg, 68%) as a white solid. LCMS: R$_t$=0.55 min; m/z=332.3 (M+1) Method 2m_acidic. ¹H NMR (500 MHz, CDCl₃-d) δ 7.48-7.36 (m, 5H), 5.09 (d, J=11.3 Hz, 1H), 4.93 (d, J=11.2 Hz, 1H), 4.18 (d, J=7.8 Hz, 1H), 3.87-3.75 (m, 2H), 3.66-3.54 (m, 2H), 3.42-3.35 (m, 1H), 3.30 (s, 1H), 3.10 (d, J=12.2 Hz, 1H), 3.03 (d, J=10.1 Hz, 1H), 2.81-2.72 (m, 2H), 2.48-2.39 (m, 2H), 1.38 (dd, J=14.2, 9.2 Hz, 1H).

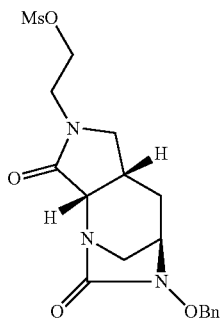 [SMILES: CS(=O)(=O)OCCN1C[C@@H]2C[C@@H]3CN(C(=O)N3OCc3ccccc3)[C@@H]2C1=O]

Step 2: 2-((4R,5aS,8aS)-3-(benzyloxy)-2,8-dioxooctahydro-7H-1,4-methanopyrrolo[3,4-d][1,3]diazepin-7-yl)ethyl methanesulfonate To a soln of (4R,5aS,8aS)-3-(benzyloxy)-7-(2-hydroxyethyl)hexahydro-2H-1,4-methanopyrrolo[3,4-d][1,3]diazepine-2,8(3H)-dione (265.4 mg, 0.801 mmol) and TEA (140 µl, 1.00 mmol) in DCM (4.0 mL) was added MsCl (65.5 µl, 0.841 mmol). After 45 min it was washed with water. The aqeuous layer was extracted with DCM (2×) and the combined organic layers were dried over Na₂SO₄/MgSO₄, filtered and concd in vacuo, affording the title compound (332 mg) as a white solid. LCMS: R$_t$=0.55 min; m/z=410.3 (M+1) Method 2m_acidic.

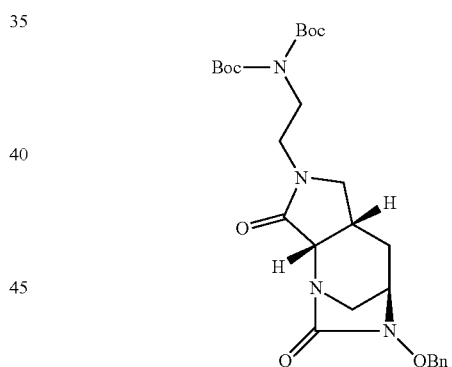

Step 3: Di-tert-butyl (2-((4R,5aS,8aS)-3-(benzyloxy)-2,8-dioxooctahydro-7H-1,4-methanopyrrolo[3,4-d][1,3]diazepin-7-yl)ethyl)iminodicarboxylate To a soln of di-tert-butyl-iminodicarboxylate (153 mg, 0.704 mmol) in DMF (3.2 mL) was added potassium tert-butoxide (1 M in THF, 700 µL, 0.700 mmol). After 30 min at rt, a solution of 2-((4R,5aS,8aS)-3-(benzyloxy)-2,8-dioxooctahydro-7H-1,4-methanopyrrolo[3,4-d][1,3]diazepin-7-yl)ethyl methanesulfonate (262 mg, 0.640 mmol) in DMF (2 mL, 2×500 µL washes) was added. It was stirred at rt for 10 min, heated to 50° C. for 100 min then stirred at rt for 12 h, whereupon it was diluted with EtOAc and washed with brine (% saturated). The aqueous layer was extracted with EtOAc (2×) and the combined organic layers were dried over Na₂SO₄/MgSO₄, filtered and concentrated in vacuo. The crude residue was purified via silica gel chromatography (EtOAc-heptane, 0-90%), affording the title compound (293 mg, 86%) as a white solid. LCMS: $R_t$=0.87 min; m/z=431.4 (M−Boc+1) Method 2m_acidic.

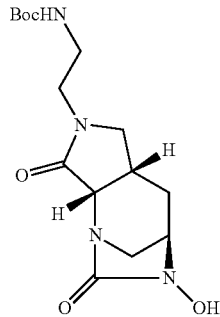 [SMILES: CC(C)(C)OC(=O)NCCN1C[C@@H]2C[C@@H]3CN(C(=O)N3O)[C@@H]2C1=O]

Step 4: tert-butyl (2-((4R,5aS,8aS)-3-hydroxy-2,8-dioxooctahydro-7H-1,4-methanopyrrolo[3,4-d][1,3]diazepin-7-yl)ethyl)carbamate A slurry of di-tert-butyl (2-((4R,5aS,8aS)-3-(benzyloxy)-2,8-dioxooctahydro-7H-1,4-methanopyrrolo[3,4-d][1,3]diazepin-7-yl)ethyl)iminodicarboxylate (226.8 mg, 0.427 mmol) and Pd—C (10% Degussa type 101, 50% water, 45.3 mg, 0.021 mmol) in MeOH (4.2 mL) was degassed and backfilled with $H_2$ (3×). After 3 h of vigorous stirring the slurry was purged with $N_2$, filtered through celite and concentrated in vacuo. Toluene was added and it was sonicated then reconcentrated. Assumed quantitative yield. LCMS: $R_t$=0.65 min; m/z=341.4 (M+1) Method 2m_acidic.

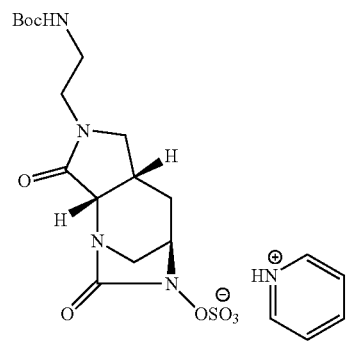

Step 5: Pyridin-1-ium (4R,5aS,8aS)-7-(2-((tert-butoxycarbonyl)amino)ethyl)-2,8-dioxohexahydro-2H-1,4-methanopyrrolo[3,4-d][1,3]diazepin-3(4H)-yl sulfate To a solution of tert-butyl (2-((4R,5aS,8aS)-3-hydroxy-2,8-dioxooctahydro-7H-1,4-methanopyrrolo[3,4-d][1,3]diazepin-7-yl)ethyl)carbamate in pyridine (3 mL) was added $SO_3$·Pyridine (335 mg, 2.10 mmol). After 15 h at rt it was concentrated in vacuo, slurried in DCM and filtered, affording the title compound as an off-white solid. Assumed quantitative yield. LCMS: $R_t$=0.59 min; m/z=321.4 (M−Boc+1) Method 2m_acidic.

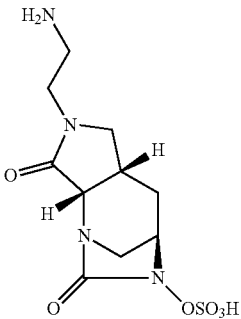

Step 6: (4R,5aS,8aS)-7-(2-aminoethyl)-2,8-dioxohexahydro-2H-1,4-methanopyrrolo[3,4-d][1,3]diazepin-3(4H)-yl hydrogen sulfate To a slurry of pyridin-1-ium (4R,5aS,8aS)-7-(2-((tert-butoxycarbonyl)amino)ethyl)-2,8-dioxohexahydro-2H-1,4-methanopyrrolo[3,4-d][1,3]diazepin-3(4H)-yl sulfate (210 mg, 0.421 mmol) in DCM (4.2 mL) at 0° C. was added TFA (973 µl, 12.63 mmol). After 2.5 h at 0° C. it was concentrated in vacuo, slurried in DCM and reconcentrated. The crude residue was taken up in phosphate buffer (pH=6), filtered and purified by reverse phase prep HPLC (T3, Atlantis column, 30×100 mm, 5 µm, C18 column; water with 3.75 mmol $NH_4OAC$ buffer, 20-60 mL/min), affording the title compound (155 mg) as a white powder. LCMS: $R_t$=0.22 min; m/z=321.4 (M+1) Method T3_3m_polar. $^1H$ NMR (500 MHz, $D_2O$) δ 4.00 (d, J=8.1 Hz, 1H), 3.94 (s, 1H), 3.61 (dt, J=14.3, 6.9 Hz, 1H), 3.45 (dd, J=10.5, 6.4 Hz, 1H), 3.28 (dt, J=14.8, 5.6 Hz, 1H), 3.06 (br d, J=12.4 Hz, 1H), 2.96 (t, J=6.2 Hz, 2H), 2.92 (d, J=10.5 Hz, 1H), 2.68 (d, J=12.3 Hz, 1H), 2.55 (p, J=8.3 Hz, 1H), 2.31-2.21 (m, 1H), 1.38 (dd, J=14.9, 9.1 Hz, 1H).

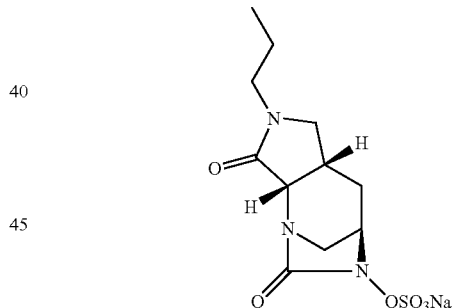

Example 6. Sodium (4R,5aS,8aS)-2,8-dioxo-7-propylhexahydro-2H-1,4-methanopyrrolo[3,4-d][1,3]diazepin-3(4H)-yl sulfate

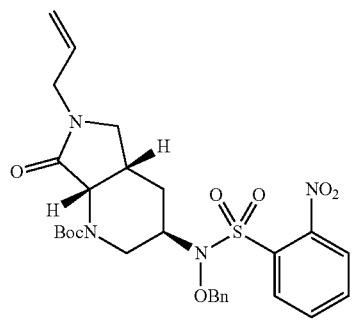 [SMILES: C=CCN1C[C@@H]2C[C@@H](N(OCc3ccccc3)S(=O)(=O)c3ccccc3[N+](=O)[O-])CN(C(=O)OC(C)(C)C)[C@@H]2C1=O]

Step 1: tert-Butyl (3R,4aS,7aS)-6-allyl-3-((N-(benzyloxy)-2-nitrophenyl)sulfonamido)-7-oxooctahydro-1H-pyrrolo[3,4-b]pyridine-1-carboxylate To a solution of tert-butyl (3S,4aS,7aS)-6-allyl-3-hydroxy-7-oxooctahydro-1H-pyrrolo[3,4-b]pyridine-1-carboxylate (786.4 mg, 2.65 mmol), N-(benzyloxy)-2-nitrobenzenesulfonamide (900 mg, 2.92 mmol) and triphenylphosphine (835 mg, 3.18 mmol) in THF (29 mL) at −17° C. was added DIAD (0.640 mL, 3.18 mmol) as a soln in THF (4.1 mL) drop-wise at 6:30 μm. It was allowed to slowly warm to rt and stir for 22 h then concentrated in vacuo and purified directly via silica gel chromatography (EtOAc-heptane, 0-40%), affording the title compound (846 mg, 54%) as an off-white solid. LCMS: $R_t$=0.95 min; m/z=587.3 (M+1) Method 2m_acidic.

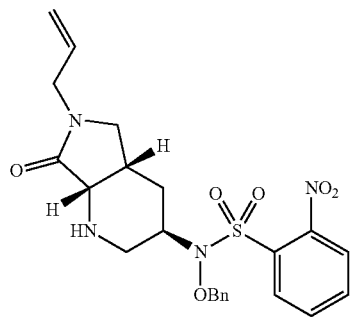 [SMILES: C=CCN1C[C@@H]2C[C@@H](N(OCc3ccccc3)S(=O)(=O)c3ccccc3[N+](=O)[O-])CN[C@@H]2C1=O]

Step 2: N-((3R,4aS,7aS)-6-allyl-7-oxooctahydro-1H-pyrrolo[3,4-b]pyridin-3-yl)-N-(benzyloxy)-2-nitrobenzenesulfonamide To a flask charged with zinc(II) bromide (681 mg, 3.02 mmol, dried at 200° C. for 4 h) and tert-butyl (3R,4aS,7aS)-6-allyl-3-((N-(benzyloxy)-2-nitrophenyl)sulfonamido)-7-oxooctahydro-1H-pyrrolo[3,4-b]pyridine-1-carboxylate (845 mg, 1.44 mmol), under $N_2$, was added DCM (4.8 mL). After stirring at rt for 15 h, it was diluted with DCM and quenched with saturated $NaHCO_3$. Upon cessation of bubbling, the layers were separated and the aqueous was extracted with DCM (3×). The combined organic layers were dried over $Na_2SO_4$ and concentrated in vacuo, resulting in a white foam. Assumed quantitative yield. LCMS: $R_t$=0.70 min; m/z=487.2 (M+1) Method 2m_acidic.

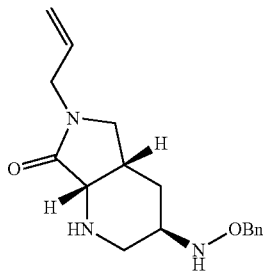 [SMILES: C=CCN1C[C@@H]2C[C@@H](NOCc3ccccc3)CN[C@@H]2C1=O]

Step 3: (3R,4aS,7aS)-6-allyl-3-((benzyloxy)amino)octahydro-7H-pyrrolo[3,4-b]pyridin-7-one To a slurry of N-((3R,4aS,7aS)-6-allyl-7-oxooctahydro-1H-pyrrolo[3,4-b]pyridin-3-yl)-N-(benzyloxy)-2-nitrobenzenesulfonamide (1.44 mmol) and $K_2CO_3$ (995 mg, 7.20 mmol) in ACN (14.4 mL) was added thiophenol (764 μL, 7.20 mmol). After 21 h it was filtered and concentrated in vacuo. The crude residue was purified via silica gel chromatography (MeOH-DCM, 0-8%), affording the title compound (385 mg, 89%, 2-steps) as an off-white foam. LCMS: Rt=0.49 min; m/z=302.4 (M+1) Method 2m_acidic.

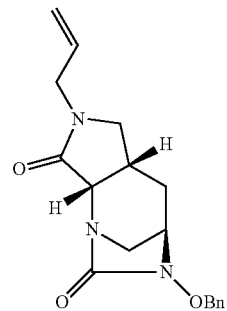 [SMILES: C=CCN1C[C@@H]2C[C@@H]3CN(C(=O)N3OCc3ccccc3)[C@@H]2C1=O]

Step 4: (4R,5aS,8aS)-7-allyl-3-(benzyloxy)hexahydro-2H-1,4-methanopyrrolo[3,4-d][1,3]diazepine-2,8(3H)-dione To a solution of (3R,4aS,7aS)-6-allyl-3-((benzyloxy)amino)octahydro-7H-pyrrolo[3,4-b]pyridin-7-one (385 mg, 1.28 mmol) and DIPEA (670 μL, 3.83 mmol) in ACN (40 mL) at 0° C. was added phosgene (1.20 mL, 1.66 mmol) as a solution in ACN (5.7 mL) at a rate of 6.5 mL/h. It was allowed to slowly raise to rt. After 20 h it was concentrated in vacuo, partitioned between EtOAc/HCl (0.2 N) and the phases were separated. The aqueous layer was extracted with EtOAc (3×) and the combined organic layers were washed with brine and saturated $NaHCO_3$. The brine wash was combined with the saturated $NaHCO_3$ wash and the solution was extracted with 10% MeOH/DCM (2×). The acidic aqueous layer was re-extracted with 10% MeOH/DCM (2×) and the combined organic layers were dried over $Na_2SO_4$, filtered and concentrated in vacuo. The crude residue was purified via silica gel chromatography (MeOH-DCM, 0-10%), affording the title compound (369.2 mg, 88%) as a white foam. LCMS: Rt=0.60 min; m/z=328.4 (M+1) Method 2m_acidic.

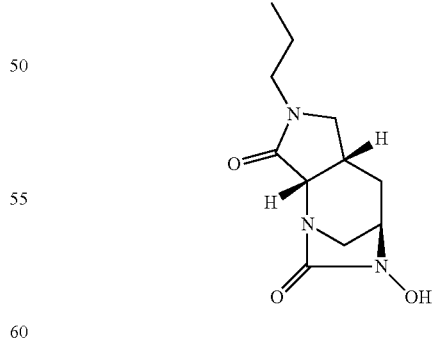

Step 5: (4R,5aS,8aS)-3-hydroxy-7-propylhexahydro-2H-1,4-methanopyrrolo[3,4-d][1,3]diazepine-2,8(3H)-dione A slurry of (4R,5aS,8aS)-7-allyl-3-(benzyloxy)hexahydro-2H-1,4-methanopyrrolo[3,4-d][1,3]diazepine-2,8

(3H)-dione (209 mg, 0.638 mmol) and Pd—C (10% Degussa type 101, 50% water, 41 mg, 0.019 mmol) in MeOH (6.4 mL) was degassed and backfilled with H₂ (3×). After 5 h of vigorous stirring the slurry was purged with N₂, more Pd—C (10% Degussa type 101, 50% water, 41 mg, 0.019 mmol) was added and it was degassed and backfilled with H₂ (3×). After 2 h of vigorous stirring it was purged with N₂ then filtered through celite and concentrated in vacuo. Toluene was added and it was sonicated then reconcentrated. Assumed quantitative yield. LCMS: $R_t$=0.27 min; m/z=240.3 (M+1) Method 2m_acidic.

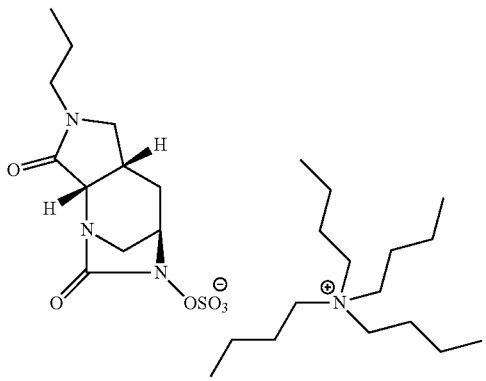

Step 6: Tetrabutylammonium (4R,5aS,8aS)-2,8-dioxo-7-propylhexahydro-2H-1,4-methanopyrrolo[3,4-d][1,3]diazepin-3(4H)-yl sulfate To a solution of (4R,5aS,8aS)-3-hydroxy-7-propylhexahydro-2H-1,4-methanopyrrolo[3,4-d][1,3]diazepine-2,8(3H)-dione (0.638 mmol) in pyridine (6.4 mL) was added SO₃.Py (508 mg, 3.19 mmol). After stirring for 13 h at rt the mixture was filtered and concentrated in vacuo. The resulting solid was dissolved in NaH₂PO₄ (1 M aq, 40 mL), whereupon tetrabutylammonium hydrogen sulfate (325 mg, 0.957 mmol) was added. After stirring for 1.5 h it was extracted with DCM (4×) and the combined organic layers were dried over Na₂SO₄, filtered and concentrated in vacuo. The crude residue was purified via silica gel chromatography (MeOH-DCM, 0-15%) to afford the title compound (229 mg, 64%, 3-steps) as a white solid. LCMS: $R_t$=0.81 min; m/z=436.3 (M+1) Method 2m_acidic.

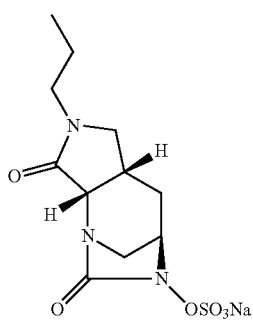

Step 7: Sodium (4R,5aS,8aS)-2,8-dioxo-7-propylhexahydro-2H-1,4-methanopyrrolo[3,4-d][1,3]diazepin-3(4H)-yl sulfate DOWEX 50W×8 hydrogen form 200-400 mesh was conditioned by stirring with NaOH (2 N) for 2 h. The resin was loaded onto a glass column and washed with water (until pH=6) followed by water:acetone (1:1). A solution of tetrabutylammonium (4R,5aS,8aS)-2,8-dioxo-7-propylhexahydro-2H-1,4-methanopyrrolo[3,4-d][1,3]diazepin-3(4H)-yl sulfate (228 mg, 0.408 mmol) in water:acetone (1:1) was loaded onto and passed through the column, eluting with water:acetone (1:1). The sample was concentrated in vacuo (bath temp <30° C.) and lyophilized, affording the title compound (120 mg, 85%) as a white powder. LCMS: $R_t$=0.30 min; m/z=320.3 (M+1) Method 2m_acidic. ¹H NMR (500 MHz, D₂O) δ 4.18 (d, J=8.0 Hz, 1H), 4.14 (s, 1H), 3.54 (dd, J=10.9, 6.3 Hz, 1H), 3.32-3.17 (m, 3H), 3.10 (d, J=10.8 Hz, 1H), 2.80 (d, J=12.2 Hz, 1H), 2.69 (p, J=8.2 Hz, 1H), 2.50-2.41 (m, 1H), 1.57-1.47 (m, 3H), 0.81 (t, J=7.4, 3H).

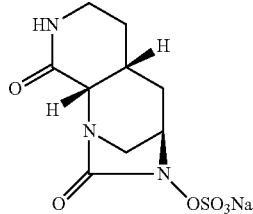

Example 7. Sodium (4R,5aR,9aS)-2,9-dioxooctahydro-1,4-methanopyrido[3,4-d][1,3]diazepin-3(2H)-yl hydrogen sulfate

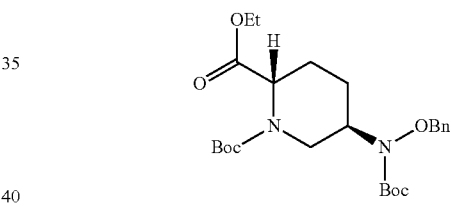

Step 1: 1-(tert-butyl) 2-ethyl (2S,5R)-5-((benzyloxy)(tert-butoxycarbonyl)amino)piperidine-1,2-dicarboxylate To a suspension of (2S,5R)-ethyl 5-((benzyloxy)amino)piperidine-2-carboxylate oxalate (13.25 g, 36.0 mmol) in EtOAc (200 mL) were added Na₂CO₃ (2.0 M, 80 mL, 160 mmol) and sodium hydroxide (1.0 M, 40 mL, 40 mmol). The mixture was stirred at room temperature for 30 min. The precipitate formed was filtered off and the two layers of the filtrate were separated. The organic layer was washed with brine (50 ml), dried over Na₂SO₄, filtered and concentrated in vacuo, affording a viscous oil (10.0 g). To a solution of this oil (10.0 g, 35.9 mmol) in THF (100 ml) were added Boc-anhydride (23.5 g, 108 mmol), triethylamine (15.0 ml, 108 mmol) and DMAP (4.38 g, 35.9 mmol). The reaction mixture was stirred for 60 h and then heated at 50° C. for 2 days. The solvent was removed in vacuo and taken back up in EtOAc/Heptane (300 mL, 1/1), washed with water (100 mL), HCl (0.1 N, 50 mL), brine (50 mL), dried over Na₂SO₄, filtered and concentrated in vacuo. The crude residue was purified via silica gel chromatography (EtOAc-Heptane, 0-40%) to afford the title compound (9.6 g, 55%) as an oil. LCMS: $R_t$=1.19 min, m/z=479.2 (M+1), Method 2m_acidic.

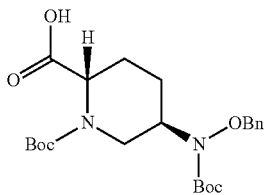 [SMILES: CC(C)(C)OC(=O)N1C[C@H](N(OCc2ccccc2)C(=O)OC(C)(C)C)CC[C@H]1C(=O)O]

Step 2: (2S,5R)-5-((benzyloxy)(tert-butoxycarbonyl)amino)-1-(tert-butoxycarbonyl)piperidine-2-carboxylic Acid To a solution of 1-(tert-butyl) 2-ethyl (2S,5R)-5-((benzyloxy)(tert-butoxycarbonyl)amino)piperidine-1,2-dicarboxylate (9.60 mg, 20.06 mmol) in THF:MeOH (3:1, 80 mL) at 0° C. was slowly added a solution of sodium hydroxide (1 N, 40 mL). After 5 h at rt, HCl (1 N, 41 mL) was slowly added the it was extracted with EtOAc (300 mL). The organic layer was dried over $Na_2SO_4$, filtered and concentrated in vacuo to afford the title compound (8.78 g, 97%) as a soft solid. LCMS: $R_t$=1.05 min, m/z=451.2 (M+1) Method 2m_acidic.

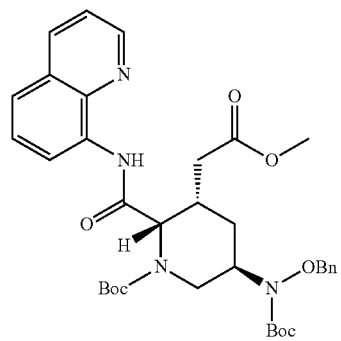

Step 4: tert-Butyl (2S,3S,5R)-5-((benzyloxy)(tert-butoxycarbonyl)amino)-3-(2-methoxy-2-oxoethyl)-2-(quinolin-8-ylcarbamoyl)piperidine-1-carboxylate To a solution of tert-butyl (2S,5R)-5-((benzyloxy)(tert-butoxycarbonyl)amino)-2-(quinolin-8-ylcarbamoyl)piperidine-1-carboxylate (5.580 g, 9.68 mmol) in 2-methyl-2-butanol (95 mL) were added dibenzyl hydrogen phosphate (538 mg, 1.94 mmol), silver carbonate (5.336 mg, 19.35 mmol), Pd(II) acetate (434 mg, 1.94 mmol) and methyl 2-bromoacetate (2.83 mL, 29.0 mmol). The mixture was purged with argon, sealed and heated to 110° C. for 20 h. Additional Pd(II) acetate (217 mg, 0.97 mmol) and methyl 2-bromoacetate (1.88 mL, 19.36 mmol) were added and the reaction mixture was stirred at 110° C. for another 20 h. The mixture was cooled to room temperature, diluted with DCM (100 ml), filtered and concentrated in vacuo. The crude residue was purified via silica gel chromatography (EtOAc-Heptane, 0-35%) to afford the title compound (2.170 g, 35%) as a viscous oil. LCMS: $R_t$=1.26 min, m/z=649.3 (M+1), Method 2m_acidic.

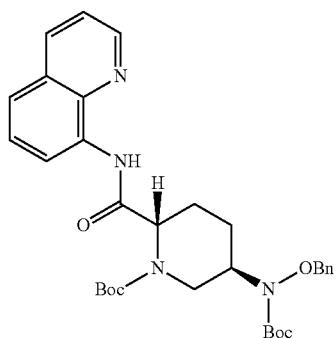 [SMILES: CC(C)(C)OC(=O)N1C[C@H](N(OCc2ccccc2)C(=O)OC(C)(C)C)CC[C@H]1C(=O)Nc1cccc2cccnc12]

Step 3: tert-Butyl (2S,5R)-5-((benzyloxy)(tert-butoxycarbonyl)amino)-2-(quinolin-8-ylcarbamoyl)piperidine-1-carboxylate To a solution of (2S,5R)-5-((benzyloxy)(tert-butoxycarbonyl)amino)-1-(tert-butoxycarbonyl)piperidine-2-carboxylic acid (6.010 g, 13.34 mmol) in DCM (100 mL) at 0° C. was added quinolin-8-amine (2116 mg, 14.67 mmol) followed by DIPEA (4.66 mL, 26.7 mmol) and HATU (6.087 g, 16.01 mmol). After stirring under argon at rt for 2.5 h, the mixture was poured into water (150 mL) and extracted with DCM (100 mL). The organic layer was dried over $MgSO_4$, filtered and concentrated in vacuo. The crude residue was purified via silica gel chromatography (EtOAc-Heptane, 10-40%), affording the title compound (6.60 g, 86%) as a soft solid. LCMS: $R_t$=1.22 min, m/z=577.3 (M+1), Method 2m_acidic.

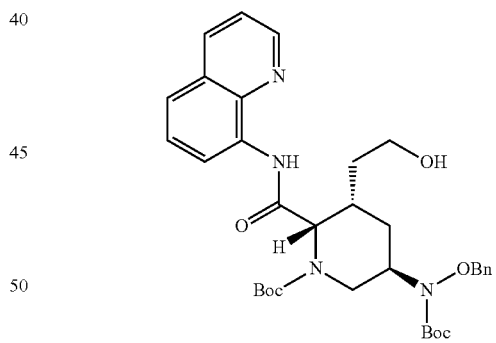

Step 5: tert-Butyl (2S,3S,5R)-5-((benzyloxy)(tert-butoxycarbonyl)amino)-3-(2-hydroxyethyl)-2-(quinolin-8-ylcarbamoyl)piperidine-1-carboxylate To a solution of tert-butyl (2S,3S,5R)-5-((benzyloxy)(tert-butoxycarbonyl)amino)-3-(2-methoxy-2-oxoethyl)-2-(quinolin-8-ylcarbamoyl)piperidine-1-carboxylate (2.40 g, 3.70 mmol) in THF (60 mL) at 0° C. was added superhydride (1.0 M in THF, 18.50 mL, 18.5 mmol). After stirring at 0° C. for 5 h, AcOH (50% aq, 10 ml) was added followed by saturated $NH_4Cl$ (30 mL) and EtOAc (150 mL). The layers were separated and the organic layer was washed with brine (50 mL), dried over $Na_2SO_4$, filtered and concentrated in vacuo. The crude residue was purified via silica gel chromatography (EtOAc-Heptane, 10-60%) to afford the title compound (680 mg, 30%). LCMS: $R_t$=1.16 min, m/z=621.1 (M+1), Method 2m_acidic.

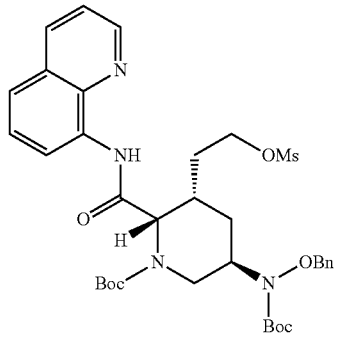 [SMILES: CC(C)(C)OC(=O)N1C[C@H](N(OCc2ccccc2)C(=O)OC(C)(C)C)C[C@@H](CCOS(C)(=O)=O)[C@H]1C(=O)Nc1cccc2cccnc12]

Step 6: tert-Butyl (2S,3S,5R)-5-((benzyloxy)(tert-butoxycarbonyl)amino)-3-(2-((methylsulfonyl)oxy)ethyl)-2-(quinolin-8-ylcarbamoyl)piperidine-1-carboxylate To a solution of tert-butyl (2S,3S,5R)-5-((benzyloxy)(tert-butoxycarbonyl)amino)-3-(2-hydroxyethyl)-2-(quinolin-8-ylcarbamoyl)piperidine-1-carboxylate (680 mg, 1.10 mmol) in dichloromethane (20 mL) at 0° C. were added triethylamine (0.30 mL, 2.19 mmol) and methylsulfonyl chloride (0.17 mL, 2.19 mmol). After stirring for 20 h at rt the mixture was diluted with water (20 mL) and EtOAc (100 mL) and stirred for an additional 15 min, whereupon the layers were separated. The organic layer was washed with NaH$_2$PO$_4$ (1.0 M, 2×40 mL), brine (30 mL), dried over Na$_2$SO$_4$, filtered and concentrated in vacuo, affording the title compound (quantitative yield) as a soft solid. LCMS: $R_t$=1.22 min, m/z=699.4 (M+1), Method 2m_acidic.

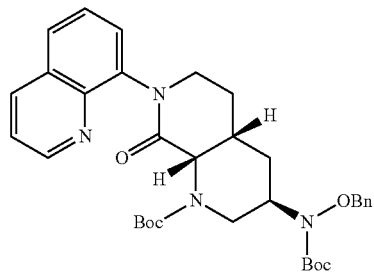 [SMILES: CC(C)(C)OC(=O)N1C[C@H](N(OCc2ccccc2)C(=O)OC(C)(C)C)C[C@H]2CCN(c3cccc4cccnc34)C(=O)[C@H]21]

Step 7: tert-Butyl (3R,4aR,8aS)-3-((benzyloxy)(tert-butoxycarbonyl)amino)-8-oxo-7-(quinolin-8-yl)octahydro-1,7-naphthyridine-1(2H)-carboxylate To a solution of tert-butyl (2S,3S,5R)-5-((benzyloxy)(tert-butoxycarbonyl)amino)-3-(2-((methylsulfonyl)oxy)ethyl)-2-(quinolin-8-ylcarbamoyl)piperidine-1-carboxylate (690 mg, 0.99 mmol) in THF (16 mL) at 0° C. was added LDA (1.0 M in THF/hexane, 1.97 mL). After stirring at 0° C. for 2.5 h, it was warmed to rt and stirred overnight. Saturated NH$_4$Cl (20 mL) solution was added and the mixture was extracted with EtOAc (80 mL). The organic layer was washed with brine (20 mL), dried over Na$_2$SO$_4$, filtered and concentrated in vacuo. The crude residue was purified via silica gel chromatography (EtOAc-Heptane, 30-80%) to afford the title compound (680 mg, 45%) as a soft solid. LCMS: $R_t$=1.03 min, m/z=603.4 (M+1), Method 2m_acidic.

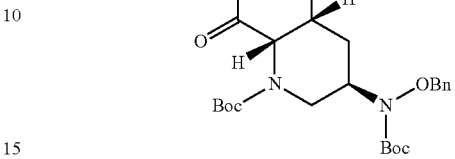

Step 8: tert-Butyl (3R,4aR,8aS)-3-((benzyloxy)(tert-butoxycarbonyl)amino)-8-oxooctahydro-1,7-naphthyridine-1(2H)-carboxylate A solution of tert-butyl (3R,4aR,8aS)-3-((benzyloxy)(tert-butoxycarbonyl)amino)-8-oxo-7-(quinolin-8-yl)octahydro-1,7-naphthyridine-1(2H)-carboxylate (270 mg, 0.448 mmol) in dry DCM (15 mL) at −78° C. was sparged with O$_3$ until a blue color persisted, whereupon the sparging line was removed. After stirring at −78° C. for 45 min, the blue color disappeared and it was again sparged with O$_3$ until the blue color persisted. After 15 min of stirring, the system was sparged with O$_2$ until it remained colorless. To the solution was added dimethyl sulfide (100 μL, 1.36 mmol). After stirring at room temperature for 1 h, the mixture was concentrated in vacuo. The residue was redissolved in THF (5 mL) and NH$_4$OH (25% aq, 5 mL) was added. After stirring for 16 h, the mixture was diluted with EtOAc (50 mL) and the organic layer was washed with water (20 ml), brine (20 ml), dried over Na$_2$SO$_4$, filtered and concentrated to in vacuo. The crude residue was purified via silica gel chromatography (EtOAc-Heptane, 70-100%) to afford the title compound (96 mg, 45%) as a solid. LCMS: $R_t$=1.00 min, m/z=476.2 (M+1), Method 2m_acidic.

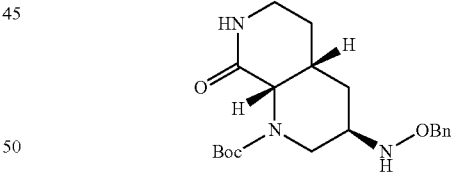

Step 9: (3R,4aR,8aS)-3-((benzyloxy)amino)octahydro-1,7-naphthyridin-8(2H)-one

To a solution of tert-butyl (3R,4aR,8aS)-3-((benzyloxy)(tert-butoxycarbonyl)amino)-8-oxooctahydro-1,7-naphthyridine-1(2H)-carboxylate (120 mg, 0.252 mmol) in DCM (3 mL) at 0° C. was slowly added TFA (1.5 mL). After 3 h at 0° C. then rt for 1 h, it was concentrated in vacuo (bath temp <30° C.). The residue was taken up in DCM:EtOH (5:1, 30 mL) and Na$_2$CO$_3$ (2 M, 10 mL) was added. The layers were separated and the aqueous layer was extracted with DCM: EtOH (5:1, 2×30 mL). The combined organic layers were dried over Na$_2$SO$_4$, filtered and concentrated in vacuo. The crude residue was purified via silica gel chromatography (MeOH-DCM, 10-25%) to afford the title compound (60 mg, 86%) as a solid. LCMS: $R_t$=0.58 min, m/z=276.1 (M+1), Method 2m_acidic.

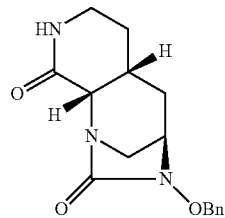 [SMILES: O=C1NCC[C@@H]2C[C@@H]3CN(C(=O)N3OCc3ccccc3)[C@H]12]

Step 10: (4R,5aR,9aS)-3-(benzyloxy)hexahydro-1,4-methanopyrido[3,4-d][1,3]diazepine-2,9(3H,6H)-dione To a solution of (3R,4aR,8aS)-3-((benzyloxy)amino)octahydro-1,7-naphthyridin-8(2H)-one (56 mg, 0.20 mmol) in ACN (21 mL) at 0° C. under $N_2$ was added DIPEA (140 μL, 0.81 mmol). A solution of triphosgene (24 mg, 0.08 mmol) in ACN (3 mL) was added via syringe pump (0.1 mL/min). After stirring at 0° C. for 6 h it was partially concentrated (~10 mL) in vacuo, diluted with DCM (40 mL), washed with water (20 mL), brine (20 mL), dried over $Na_2SO_4$, filtered and concentrated in vacuo. The crude residue was purified via silica gel chromatography (MeOH-DCM, 0-5%) to afford the title compound (50 mg, 82%) as an off-white solid. LCMS: $R_t$=0.65 min, m/z=302.0 (M+1), Method 2m_acidic.

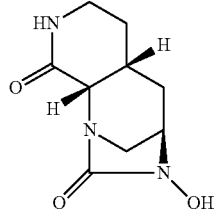 [SMILES: O=C1NCC[C@@H]2C[C@@H]3CN(C(=O)N3O)[C@H]12]

Step 11: (4R,5aR,9aS)-3-hydroxyhexahydro-1,4-methanopyrido[3,4-d][1,3]diazepine-2,9(3H,6H)-dione A slurry of (4R,5aR,9aS)-3-(benzyloxy)hexahydro-1,4-methanopyrido[3,4-d][1,3]diazepine-2,9(3H,6H)-dione (50 mg, 0.17 mmol) and Pd—C (10% Degussa type 101, 50% water, 27 mg) in MeOH:DCM (3:1, 4 mL) was evacuated and backfilled with $H_2$. After 2 h of vigorous stirring, it was filtered through a plug of celite, washing with MeOH, and concentrated in vacuo. LCMS: $R_t$=0.20 min, m/z=212.0 (M+1) Method 2m_acidic.

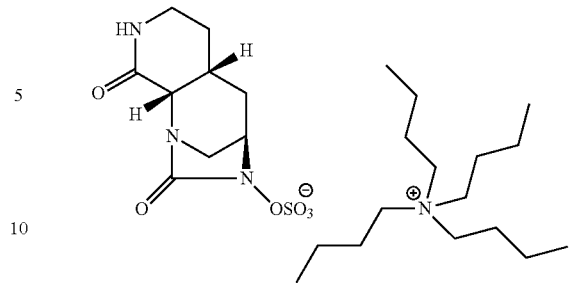

Step 12: Tetrabutylammonium (4R,5aR,9aS)-2,9-dioxooctahydro-1,4-methanopyrido[3,4-d][1,3]diazepin-3(2H)-yl sulfate To a slurry of crude (4R,5aR,9aS)-3-hydroxyhexahydro-1,4-methanopyrido[3,4-d][1,3]diazepine-2,9(3H,6H)-dione (35 mg, 0.17 mmol) in pyridine (3 ml) at 0° C. was added $SO_3 \cdot Py$ (132 mg, 0.83 mmol). After vigorous stirring at rt for 20 h, the slurry was filtered and the solid was washed with cold DCM (5 mL). The filtrate was concentrated in vacuo (bath temp <30° C.) and the crude residue was dissolved in $NaH_2PO_4$ (1 M, 10 mL), whereupon tetrabutylammonium hydrogen sulfate (84 mg, 0.25 mmol) was added. After 30 min it was extracted with $CHCl_3$:IPA (4:1, 3×30 mL). The combined organic layers were dried over $Na_2SO_4$, filtered and concentrated in vacuo. The crude residue was purified via silica gel chromatography (MeOH-DCM, 5-20%) to afford the title compound as a white foam. LCMS: $R_t$=0.15 min, m/z=292.0 (M+1), Method 2m_acidic.

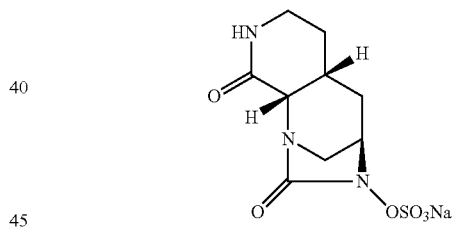

Step 13: Sodium (4R,5aR,9aS)-2,9-dioxooctahydro-1,4-methanopyrido[3,4-d][1,3]diazepin-3(2H)-yl hydrogen sulfate DOWEX 50W×8 hydrogen form 200-400 mesh was conditioned by stirring with NaOH (2 N) for 2 h. The resin was loaded onto a glass column and washed with water (until pH=6) followed by water:acetone (1:1). Tetrabutylammonium (4R,5aR,9aS)-2,9-dioxooctahydro-1,4-methanopyrido[3,4-d][1,3]diazepin-3(2H)-yl sulfate (228 mg, 0.408 mmol) in acetone:water (1:1) was loaded onto and passed through the column, eluting with water (20 ml) then acetone:water (1:4, 30 ml). The sample was lyophilized to afford the title compound (28 mg, 52%) as a white solid. LCMS: $R_t$=0.29 min, m/z=291.8 (M+1) Method T3_3m_polar; $^1$H NMR (500 MHz, $D_2O$) δ 4.31 (m, 1H), 4.09 (d, J=7.1 Hz, 1H), 3.55 (td, J=12.8, 4.3 Hz, 1H), 3.26-3.34 (m, 2H), 2.87 (d, J=12.3 Hz, 1H), 2.55-2.64 (m, 1H), 2.21-2.30 (m, 1H), 1.99-2.09 (m, 1H), 1.80-1.88 (m, 1H) 1.72-1.79 (m, 1H).

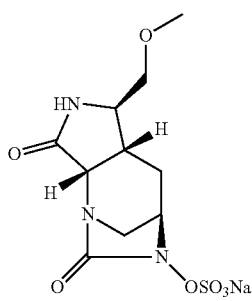

Example 8. Sodium (4R,5aS,6R,8aS)-6-(methoxymethyl)-2,8-dioxohexahydro-2H-1,4-methanopyrrolo[3,4-d][1,3]diazepin-3(4H)-yl hydrogen sulfate Step 1: Methyl (5R)-6-(benzyloxy)-3-(1-((tert-butoxycarbonyl)amino)-2-methoxyethyl)-7-oxo-1,6-diazabicyclo[3.2.1]octane-2-carboxylate (Mixture of Diastereoisomers)

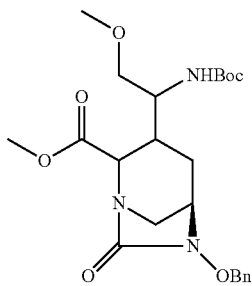 [SMILES: COCC(NC(=O)OC(C)(C)C)C1C[C@@H]2CN(C(=O)N2OCc2ccccc2)C1C(=O)OC]

Intermediate C (1.10 g, 3.82 mmol), Boc-L-Ser(OMe)-OH (1.04 g, 4.58 mmol) and Ir[df(CF₃)ppy₂(dtbpy)]PF₆ (43 mg, 0.04 mmol) were dissolved in DMF (16 mL). To the solution was added finely ground potassium phosphate dibasic (0.62 g, 4.58 mmol) and the resulting suspension was stirred and irradiated for 12 days with a Kessil H150-Blue lamp from a distance of <2 cm. After 3 and after 9 days Ir[df(CF₃)ppy₂(dtbpy)]PF₆ (43 mg, 0.04 mmol) was added (total of 3 mol % catalyst). To the reaction mixture was added water (15 mL) followed by saturated NaHCO₃ (aq, 15 mL), which was then extracted with TBME (3×60 mL). The combined organic phases were washed with brine (10 mL), dried over Na₂SO₄ and concentrated in vacuo, resulting in the title compound (1.85 g) as yellow oil consisting of 4 diastereoisomers (ratio 39:16:11:34). LCMS: R$_t$=1.02 min, 1.05 min, 1.08 min, 1.12 min all with m/z=464 (M+1), LCMS_2 MIN_REACTION_MONITORING.

Step 2: (4R,5aS,6R,8aS)-3-(benzyloxy)-6-(methoxymethyl)hexahydro-2H-1,4-methanopyrrolo[3,4-d][1,3]diazepine-2,8(3H)-dione

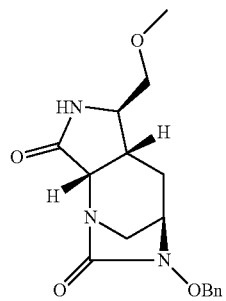 [SMILES: COC[C@@H]1NC(=O)[C@@H]2[C@H]1C[C@@H]1CN2C(=O)N1OCc1ccccc1]

To a solution of methyl (5R)-6-(benzyloxy)-3-(1-((tert-butoxycarbonyl)amino)-2-methoxyethyl)-7-oxo-1,6-diazabicyclo[3.2.1]octane-2-carboxylate (1.85 g, 4.0 mmol) in DCM (60 mL) at 0° C. was added TFA (15.4 mL, 200 mmol), drop-wise. The reaction mixture was stirred at rt for 1.5 h, then concentrated in vacuo. The crude residue was dissolved in DCM (60 mL) then triethylamine (11.1 mL, 80 mmol) was added, drop-wise. The reaction mixture stirred at rt overnight, whereupon it was concentrated to furnish a reddish oil (6.8 g). Water (20 mL) was added and the mixture extracted with TBME (3×80 mL). The combined organic phases were dried over Na₂SO₄ and concentrated in vacuo to yield a yellow oil (1.13 g). The aqueous phase was saturated with NaCl (s) and further extracted with DCM (3×80 mL). The combined organic phases were dried over Na₂SO₄ and concentrated in vacuo to yield additional crude product (0.95 g). The combined crude product was purified by HPLC chromatography (Sunfire-C18, 5 um, 50×250 mm, water/ACN+0.1% TFA, 100 ml/min, 18-38% over 21 min, total 35 min) where the pH of the fractions was adjusted to 6.9 via addition of saturated NaHCO₃ (aq) and lyophilized to afford a light brown residue (0.59 g). This residue was dissolved in ACN/water and purified over a C₁₈ cartridge (ACN-water), whereupon the lyophilized material afforded the title compound (62 mg, 4.1% 3-steps). LCMS: R$_t$=0.70 min, m/z=332 (M+1), LCMS_2 MIN_REACTION_MONITORING.

Step 3: (4R,5aS,6R,8aS)-3-hydroxy-6-(methoxymethyl) hexahydro-2H-1,4-methanopyrrolo[3,4-d][1,3]diazepine-2,8(8aH)-dione (4R,5aS,6R,8aS)-3-(benzyloxy)-6-(methoxymethyl) hexahydro-2H-1,4-methanopyrrolo[3,4-d][1,3]diazepine-2,8(8aH)-dione (59 mg, 0.178 mmol) was dissolved in MeOH:DCM (1:1, 1.78 mL). The mixture was purged with nitrogen, Pd—C (10% Degussa type, 101, 50% water, 37.9 mg, 0.018 mmol) was added, then left under an H₂ atmosphere at for 90 min. The mixture was filtered through celite, eluting with DCM:MeOH (1:1) and concentrated in vacuo to afford the title compound (49 mg, quantitative) as a colorless solid. LC/MS: R$_t$=0.12 min; m/z=242.0 (M+1) Method 2m_acidic.

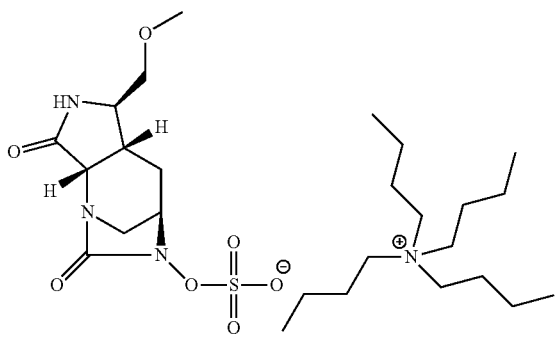 [SMILES: COC[C@@H]1NC(=O)[C@@H]2[C@H]1C[C@@H]1CN2C(=O)N1OS(=O)(=O)[O-] ; CCCC[N+](CCCC)(CCCC)CCCC]

Step 4: tetrabutylammonium (4R,5aS,6R,8aS)-6-(methoxymethyl)-2,8-dioxohexahydro-2H-1,4-methanopyrrolo[3,4-d][1,3]diazepin-3(4H)-yl sulfate To a solution of (4R,5aS,6R,8aS)-3-hydroxy-6-(methoxymethyl) hexahydro-2H-1,4-methanopyrrolo[3,4-d]

[1,3]diazepine-2,8(8aH)-dione (42 mg, 0.174 mmol) in pyridine (1.85 mL) was added SO₃.pyridine (139 mg, 0.870 mmol). The mixture was stirred for 18 h, then filtered through a membrane filter and concentrated in vacuo (bath temp <30° C.). The crude residue was dissolved in saturated NaH₂PO₄ and washed with EtOAc. The layers were separated and to the aqueous phase was added tetrabutylammonium hydrogen sulfate (89 mg, 0.261 mmol). The mixture was stirred for 30 minutes, then extracted with DCM, dried over sodium sulfate, and concentrated in vacuo. The crude residue was purified via silica gel chromatography (MeOH-DCM, 0-30%) affording the title compound (57 mg, 58%) as a colorless film. LC/MS: $R_f$=0.12 min; m/z=322.0 (M+1) Method 2m_acidic.

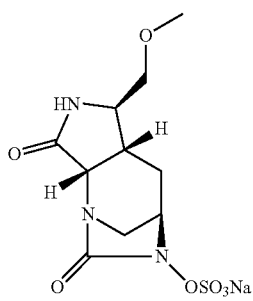

Step 5: Sodium (4R,5aS,6R,8aS)-6-(methoxymethyl)-2,8-dioxohexahydro-2H-1,4-methanopyrrolo[3,4-d][1,3]diazepin-3(4H)-yl hydrogen sulfate DOWEX 50W×8 hydrogen form 200-400 mesh was stirred with NaOH (2 N) for 3 h then loaded onto a column and washed with water until the pH of the eluant was ~6, followed by washing with water-acetone (1:1). Tetrabutylammonium (4R,5aS,6R,8aS)-6-(methoxymethyl)-2,8-dioxohexahydro-2H-1,4-methanopyrrolo[3,4-d][1,3]diazepin-3(4H)-yl sulfate (57 mg, 0.101 mmol) was dissolved in acetone-water (1:1) and passed through the column, eluting with 1:1 acetone/water. The fractions were concentrated in vacuo and lyophilized to afford the desired product (27 mg, 70%) as a colorless powder. LC/MS: $R_f$=0.41 min; m/z=321.9 (M+1) Method T3_3m_polar; ¹H NMR (500 MHz, D₂O) δ=4.30 (d, J=8.0 Hz, 1H), 4.24 (br s, 1H), 3.60-3.56 (m, 1H), 3.56-3.45 (m, 3H), 3.39 (s, 3H), 3.38-3.34 (m, 1H), 2.97 (d, J=12.3 Hz, 1H), 2.67 (q, J=8.4 Hz, 1H), 2.64-2.56 (m, 1H), 1.72 (dd, J=14.7, 8.4 Hz, 1H).

Susceptibility Testing

MICs were determined by the broth microdilution method in accordance with Clinical and Laboratories Institute (CLSI) guidelines. In brief, fresh overnight bacterial cultures were suspended in sterile saline, and adjusted to a 0.5 McFarland turbidity standard. Bacterial suspensions were then diluted in cation adjusted Mueller-Hinton Broth (MHB II; BBL) to yield a final inoculum of approximately 5×10⁵ colony-forming units (CFU)/mL. A master plate of antibiotics was prepared at a concentration equivalent to hundredfold the highest desired final concentration in 100% dimethyl sulfoxide (DMSO). The master antibiotic plate was then diluted by serial twofold dilution with a multichannel pipette. The resulting dilution series of compounds were diluted 1:10 with sterile water or a solution of beta-lactamase inhibitor prepared at a concentration equivalent to eleven-fold the desired final concentration in deionized water leading to a 10% DMSO final concentration. A volume of 10 μL of the drug dilution series was transferred to 96-well assay plates. Assay plates were inoculated with 90 μL of bacterial suspensions and incubated at 35° C. for 20 hrs. The assay plates were read using a microtiter plate reader (Molecular Devices) at 600 nm as well as by visual observation with a reading mirror. The lowest concentration of the compound that prevented visible growth was recorded as the MIC. Performance of the assay was monitored by testing aztreonam against laboratory quality control strains in accordance with guidelines of the CLSI.

The following beta-lactamase inhibitors and beta-lactam antibiotics are mentioned in the following tables:

Beta-Lactamase Inhibitor 1: Avibactam

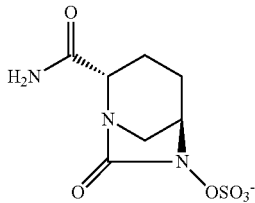

Beta-Lactamase Inhibitor 2: Relebactam

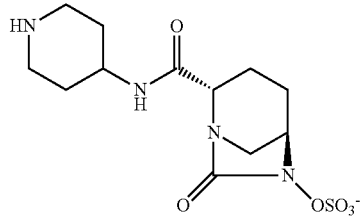

Beta-Lactamase Inhibitor 3: Tazobactam

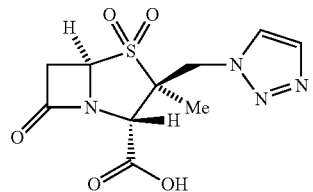 [SMILES: C[C@]1(Cn2ccnn2)[C@H](C(=O)O)N2C(=O)C[C@H]2S1(=O)=O]

Beta-Lactam 1: Aztreonam

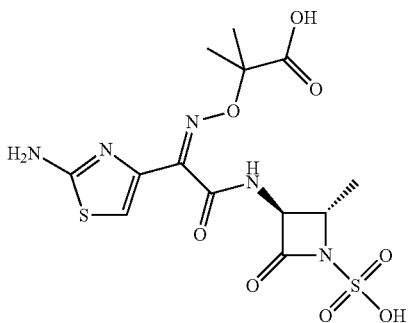 [SMILES: C[C@H]1[C@H](NC(=O)/C(=N\OC(C)(C)C(=O)O)c2csc(N)n2)C(=O)N1S(=O)(=O)O]

Beta-Lactam 2: Ceftazidime

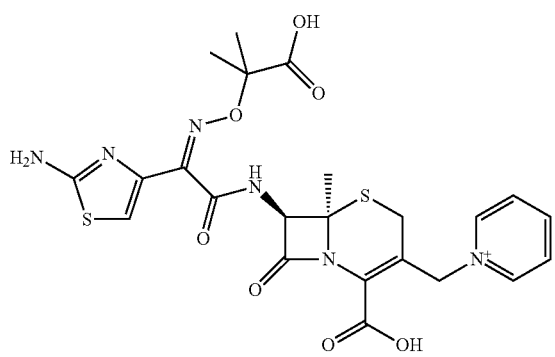 [SMILES: CC(C)(O/N=C(\C(=O)N[C@@H]1C(=O)N2C(C(=O)O)=C(C[n+]3ccccc3)CS[C@]12C)c1csc(N)n1)C(=O)O]

Beta-Lactam 3: Meropenem

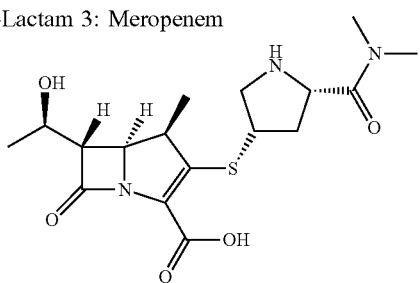

Beta-Lactam 4: Piperacillin

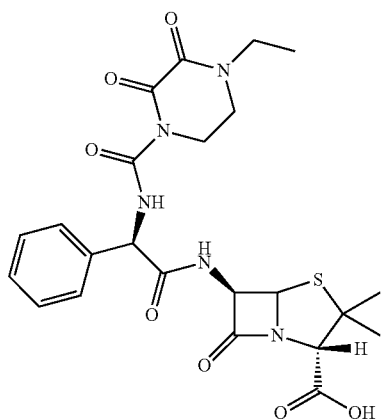 [SMILES: CCN1CCN(C(=O)N[C@@H](C(=O)N[C@@H]2C(=O)N3C2SC(C)(C)[C@@H]3C(=O)O)c2ccccc2)C(=O)C1=O]

Beta-Lactam 5 (LYS228):

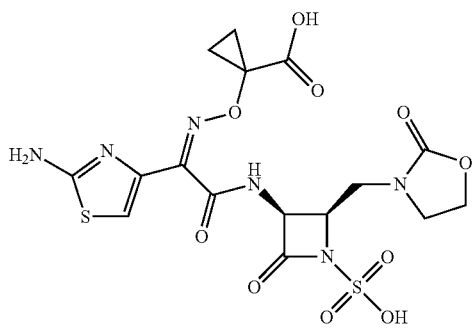 [SMILES: Nc1nc(/C(=N/OC2(C(=O)O)CC2)C(=O)N[C@@H]2C(=O)N(S(=O)(=O)O)[C@@H]2CN2CCOC2=O)cs1]

Synergy with Beta-Lactams Through Inhibition of Beta-Lactamases

Synergy or potentiation of beta-lactam antibiotics through inhibition of Q-lactamases was assessed against an isogenic panel of *E. coli* strains, each expressing a unique beta-lactamase, and against clinical strains.

Construction of *E. coli* isogenic strains NB27273-CDY0026 (parent), NB27273-CDY0033 (KPC-2), NB27273-CDY0030 (SHV-12), NB27273-CDY0034 (CTX-M-15) and NB27273-CDY0036 (AmpC).

Strain NB27273 (BW25113 pspB::Km$^r$) was obtained from the Keio transposon insertion collection. The strain has the pspB gene replaced by a kanamycin resistance marker (BW25113 pspB::Km$^r$). This strain was cured of the transposon in pspB via FLP recombinase using published methodology. The resulting strain, BW25113 pspB, was used as a host for multicopy vectors expressing key beta-lactamases. Multicopy plasmids directing constitutive expression of beta-lactamases were established as follows: Synthetic, codon optimized genes encoding *E. coli* KPC-2, SHV-12 and CTX-M-15 beta-lactamases were made by DNA2.0 (Palo Alto, Calif.). Each of the synthetic fragments were designed to contain NotI and NcoI restriction sites at their termini, allowing ligation into a NotI/NcoI digested pET28a (+) derivative for protein expression. The inserts in these vectors served as template DNA for PCR amplification of the genes encoding KPC-2, SHV-12 and CTX-M-15 using primer pairs E225 (tcgcCTCGAGgcgactgcgctgacgaatttgg) (SEQ ID NO:1) and E202 (aatcGAATTCttactgaccattaacgcccaagc) (SEQ ID NO:2) and E227 (tcgcCTCGAGgcgagcccgcaaccgctgga) (SEQ ID NO:3) and E204 (aatcGAATTCttaacgctgccagtgctcaatc) (SEQ ID NO:4) and E226 (cgctCTCGAGagcgtcccgctgtacgcacaaacg) (SEQ ID NO:5) and E203, (aatcGAATTCttacagaccgtcggtgacaatc) (SEQ ID NO:6), respectively. The codon optimized nucleotide sequences and relevant primer recognition information is shown below:

KPC-2

(SEQ ID NO: 7)
ATGGGCCATCATCATCATCATCACAGCAGCGGCCTGGAAGTTCTGTTCCA

GGGGCCCGCGACTGCGCTGACGAATTTGGTGGCCGAGCCGTTCGCGAAAT

TGGAGCAAGATTTTGGTGGTTCGATCGGTGTCTACGCGATGGACACCGGT

AGCGGTGCCACCGTGAGCTACCGTGCCGAAGAGCGTTTTCCGCTGTGTAG

CTCTTTCAAGGGTTTTCTGGCCGCAGCCGTGCTGGCACGCAGCCAACAGC

AAGCGGGCCTGCTGGACACCCCGATCCGTTACGGCAAAAATGCGCTGGTT

CCGTGGAGCCCGATTAGCGAAAAGTACCTGACCACCGGCATGACGGTGGC

GGAGTTGAGCGCTGCGGCGGTTCAGTATTCCGATAACGCTGCGGCAAATC

TGCTGCTGAAAGAACTGGGCGGTCCAGCGGGTCTGACGGCTTTCATGCGT

TCTATTGGCGACACCACCTTTCGCTTGGACCGCTGGGAGCTGGAGCTGAA

CAGCGCGATTCCGGGCGACGCACGTGATACGAGCAGCCCGCGTGCAGTGA

CCGAGAGCCTGCAGAAGCTGACCCTGGGCAGCGCACTGGCCGCACCGCAG

CGCCAACAGTTCGTCGATTGGCTGAAGGGTAACACCACCGGTAACCATCG

TATTCGCGCAGCGGTCCCGGCTGATTGGGCAGTTGGTGACAAGACTGGTA

CGTGCGGCGTTTATGGTACGGCGAATGACTACGCGGTTGTTTGGCCTACG

GGTCGTGCGCCGATCGTCCTGGCGGTGTATACCCGTGCTCCGAACAAAGA

-continued

CGATAAACACTCCGAAGCGGTCATCGCCGCAGCAGCGCGTCTGGCCCTGG

AAGGCTTGGGCGTTAATGGTCAGTAACGCCGGCG

E225
(SEQ ID NO: 8)
TCGCCTCGAGGCGACTGCGCTGACGAATTTGG

E202
(SEQ ID NO: 9)
AATCGAATTCTTACTGACCATTAACGCCCAAGC

REV. COMP. E202
(SEQ ID NO: 10)
GCTTGGGCGTTAATGGTCAGTAAGAATTCGATT
UNDERLINED = DNA ENCODING BL

SHV-12
(SEQ ID NO: 11)
ATGGGCCATCATCATCATCATCACAGCAGCGGCCTGGAAGTTCTGTTCCA

GGGGCCCGCGAGCCCGCAACCGCTGGAGCAGATCAAGCAGTCTGAGAGCC

AGCTGAGCGGCCGTGTGGGTATGATCGAGATGGATCTGGCTTCCGGCCGT

ACGCTGACGGCATGGCGTGCCGACGAACGTTTCCCGATGATGTCGACCTT

TAAAGTTGTTCTGTGTGGTGCGGTCTTGGCACGTGTAGACGCGGGTGACG

AACAACTGGAGCGCAAGATCCATTACCGCCAACAGGACTTGGTCGACTAC

AGCCCGGTTAGCGAAAAGCACCTGGCGGATGGCATGACCGTGGGTGAATT

GTGCGCCGCTGCGATTACCATGAGCGACAATAGCGCGGCTAATCTGCTGT

TGGCGACCGTTGGTGGCCCAGCGGGCTTGACCGCATTTCTGCGTCAAATC

GGCGATAATGTTACGCGTCTGGATCGCTGGGAAACGGAGCTGAACGAGGC

ACTGCCGGGTGATGCCCGTGATACCACGACTCCTGCTAGCATGGCAGCGA

CCCTGCGTAAACTGCTGACCAGCCAGCGTCTGAGCGCACGTAGCCAACGC

CAGCTGCTGCAATGGATGGTGGATGACCGCGTGGCGGGTCCGCTGATCCG

CTCCGTCCTGCCAGCAGGCTGGTTCATTGCGGACAAAACTGGTGCCTCTA

AGCGTGGTGCGCGTGGTATCGTCGCGCTGCTGGGTCCGAACAACAAAGCC

GAACGTATTGTGGTTATCTATCTGCGCGACACCCCGGCAAGCATGGCCGA

GCGCAACCAGCAAATTGCGGGCATTGGTGCGGCACTGATTGAGCACTGGC

AGCGTTAACGCCGGCG

E227
(SEQ ID NO: 12)
TCGCCTCGAGGCGAGCCCGCAACCGCTGGA

E204
(SEQ ID NO: 13)
AATCGAATTCTTAACGCTGCCAGTGCTCAATC

REV. COMP. E204
(SEQ ID NO: 14)
GATTGAGCACTGGCAGCGTTAAGAATTCGATT

CTX-M-15
(SEQ ID NO: 39)
ATGGGCCATCATCATCATCATCACAGCAGCGGCCTGGAAGTTCTGTTCCA

GGGGCCCAGCGTCCCGCTGTACGCACAAACGGCCGACGTGCAACAGAAAC

TGGCGGAGTTGGAACGTCAGAGCGGTGGCCGTTTGGGTGTAGCCCTGATC

AATACCGCGGACAATAGCCAAATTCTGTATCGTGCGGACGAACGCTTCGC

GATGTGCAGCACGAGCAAGGTGATGGCCGCTGCGGCCGTTCTGAAGAAAT

CCGAGAGCGAGCCGAACTTGCTGAATCAGCGCGTTGAGATCAAGAAGTCG

GATCTGGTGAACTATAACCCTATCGCGGAAAAACATGTCAACGGCACCAT

GTCCCTGGCAGAGCTGAGCGCGGCTGCGTTGCAGTACTCTGATAACGTCG

CAATGAATAAACTGATCGCACACGTCGGTGGCCCAGCAAGCGTGACCGCC

TTTGCGCGTCAACTGGGCGATGAAACTTTTCGTCTGGATCGTACCGAACC

GACCCTGAATACGGCAATTCCGGGTGATCCGCGCGACACGACGAGCCCGC

GTGCAATGGCACAGACCCTGCGCAACCTGACCCTGGGTAAAGCGCTGGGC

GATAGCCAACGTGCGCAGCTGGTTACGTGGATGAAGGGTAACACCACCGG

TGCGGCCAGCATTCAAGCGGGCCTGCCGGCCAGCTGGGTTGTTGGTGATA

AAACTGGCTCCGGTGGTTATGGTACCACGAATGACATCGCGGTTATTTGG

CCGAAGGACCGTGCGCCGTTGATCCTGGTGACCTACTTCACCCAGCCGCA

GCCGAAAGCTGAGTCTCGCCGTGACGTGCTGGCGAGCGCAGCTAAGATTG

TCACCGACGGTCTGTAACGCCGGCG

E226
(SEQ ID NO: 15)
cgctCTCGAGagcgtcccgctgtacgcacaaacg

E203,
(SEQ ID NO: 16)
aatcGAATTCttacagaccgtcggtgacaatc

The gene encoding AmpC was PCR amplified from the genome of strain *P. aeruginosa* PAO1 (NB52019) (GenBank ID U5R279) using primer pair E252 (gccCTCGAGggcgag-gccccggcggatcgc) (SEQ ID NO: 17) and E253 (tgaGAAT-TCtcagcgcttcagcggcacct) (SEQ ID NO: 18).

The PCR products were then digested with XhoI and EcoRI and ligated into similarly digested plasmid pAH63-pstS(BlaP). Plasmid pAH63-pstS(BlaP) is a derivative of plasmid pAH63 (J Bacteriol: 183(21): 6384-6393) made by cloning the TEM-1 (bla) promoter and signal peptide encoding region from plasmid pBAD (J Bacteriol. 1995 July 177(14):4121-30) into plasmid pAH63. This fragment was PCR amplified from pBAD using primer pair E192 (ttcaCT-GCAGtgaacgttgcgaagcaacggC) (SEQ ID NO:19) and E194 (TCGAggatcctcgagagcaaaaacaggaaggcaaaatgccg) (SEQ ID NO:20), digested with PstI and BamHI and inserted into similarly digested plasmid pAH63. Therefore, expression of beta-lactamases from pAH63-pstS(BlaP) based constructs is constitutive and the signal sequence is provided to direct these proteins to the periplasm. Plasmid pAH63 based vectors are used for insertion into the genome in single copy, however, to provide higher expression levels to allow more sensitive detection of the susceptibility of compounds to the expressed beta-lactamases, the expression inserts contained in these vectors were moved to the replicative multicopy vector pBAD-Kan (J Bacteriol. 1995 July 177(14):4121-30). To accomplish this, the inserts encompassing the beta-lactamase genes, with the associated TEM promoter and signal sequences, were PCR amplified from their corresponding vectors using primer E268 (ccgTCTAGAcggatg-gcctttttgcgtttc) (SEQ ID NO:21) and E202 (aatcGAATTCt-tactgaccattaacgcccaagc) (SEQ ID NO:22) for the KPC2 construct, E204 (aatcGAATTCttaacgctgccagtgctcaatc) (SEQ ID NO:23) for the SHV-12 construct and E203 (aatc-GAATTCttacagaccgtcggtgacaatc) (SEQ ID NO:24) for the CTX-M-15 construct. These fragments were then digested with XbaI and EcoRI, and each was inserted into pBAD18-kan that had been digested with the same enzymes to generate multicopy vectors expressing KPC-2, SHV-12 and CTX-M-15, respectively. These vectors were transformed into BW25113 pspB to generate strains NB27273-CDY0033 (expressing KPC-2), NB27273-CDY0030 (expressing SHV-12), NB27273-CDY0034 (expressing CTX-M-15) and NB27273-CDY0036 (expressing AmpC). The pBAD18-kan vector also contains the TEM promoter region and signal sequence, (but lacks any intact beta-lactamase genes) and was transformed into BW25113 pspB using standard protocols to generate the control strain NB27273-CDY0026. Expression of the beta-lactamases was confirmed by verifying decreased susceptibility to example test antibiotics that are known substrates of KPC-2, SHV-12, CTX-M-15 or AmpC.

Construction of E. coli isogenic strains, NB27273-CDY0105 (OXA-18) and NB27273-CDY0048 (TEM-10). The plasmid vector for expression of OXA-18, was constructed as follows: The genes encoding GIM-1 (GenBank ID Q704V1) and (OXA-18 (GenBank ID 007293) were synthesized by Life Technologies with 5'-tgccttcctgttttt-gctctcgag-3' (SEQ ID NO:40) and 5'-gaattcgctagc-ccaaaaaacgg-3' (SEQ ID NO:25) flanking sequences. The GIM-1 encoding fragment was digested with XhoI and EcoRI and inserted into the KPC-2 expression construct described above from which the KPC-2 encoding gene was removed by digestion with XhoI and EcoRI. Confirmatory nucleotide sequencing revealed a XhoI site in the vector backbone which was then removed by site directed mutagenesis using primer pair E396 (cgtcttgctccaggccgcgattaaat-tcc) (SEQ ID NO:26) and E397 (tcgcggcctggagcaagacgtttc) (SEQ ID NO:27). The gene encoding OXA-18 was then digested with XhoI and EcoRI and inserted into this vector, from which the gene for GIM-1 had been removed with XhoI and EcoRI.

To generate a vector expressing TEM-10, plasmid pBAD18 (J Bacteriol. 1995 July 177(14):4121-30), which contains the gene encoding TEM-1, was used as template for PCR based site directed mutagenesis to convert the gene encoding TEM-1 to one encoding TEM-10. From this template DNA, three fragments were generated by PCR using the following primer pairs;

B124 (tcacgtagcgatagcggag) (SEQ ID NO:28) and E387 (tggagccggtaagcgtgggtctcgcggt) (SEQ ID NO:1) to generate fragment A encoding an E237K substitution E389 (cgcgagacccacgcttaccggctccaga) (SEQ ID NO:29) and E391 (ctcgccttgatagttgggaaccgga) (SEQ ID NO:30) to generate fragment B encoding E237K and R162S substitutions E393 (cggttcccaactatcaaggcgagt) (SEQ ID NO:31) and E289 (gacattgccgtcactgcgtct) SEQ ID NO:32) to generate fragment C, also introducing an R162 substitution.

Fragments A, B and C were then used as template to generate a complete gene encoding TEM-10 as follows: Fragments A and B were used as template for PCR using primers B124 (tcacgtagcgatagcggag) (SEQ ID NO:33) and E390 (gtaactcgccttgatagttgggaaccggagctgaatgaagc) (SEQ ID NO:34) to combine fragments A and B into fragment D Fragments B and C were used as template for PCR using primers E290 (gcgggaccaaagccatgaca) (SEQ ID NO:35) and E388 (accgcgagacccacgcttaccggctccagatttatcagcaataaacc) (SEQ ID NO:36) to combine fragments B and C into fragment E Finally, Fragments D and E were used as template for PCR using primers E395 (gtaaGAATTCttaccaatgcttaatcagt-gaggc) (SEQ ID NO:37) E268 (ccgTCTAGAcggatggccttttt-gcgtttc) (SEQ ID NO:38) to combine fragments D and E into the intact TEM-10 encoding product. This fragment was then digested with XbaI and EcoRI and inserted into pBAD-kan which was also cut with the same enzymes.

These final vectors for expression of OXA-18 and TEM-10 were transformed into BW25113 pspB to generate strains NB27273-CDY0105 (expressing OXA-18) and NB27273-CDY0048 (expressing TEM-10). Beta-lactamase expression was confirmed by verifying decreased susceptibility to example test antibiotics that are known substrates of OXA-18 or TEM-10.

TABLE A

Minimal Inhibitory Concentrations (MIC), in μg/mL of selected BLIs

| BLI | E. coli ATCC 25922 | K. pneumoniae ATCC 43816 | P. aeruginosa ATCC 27853 |
|---|---|---|---|
| Avibactam | 16 | 32 | >64 |
| Relebactam | >64 | >64 | >64 |
| Example 1 | >64 | >64 | >64 |
| Example 2 | >64 | >64 | >64 |
| Example 3 | >64 | >64 | >64 |
| Example 4 | >64 | >64 | >64 |
| Example 5 | >64 | >64 | >64 |
| Example 6 | >64 | >64 | >64 |
| Example 7 | >64 | >64 | >64 |
| Example 8 | >64 | >64 | >64 |

Table 1 above demonstrates that while some beta-lactamase inhibitors such as avibactam exhibit direct antibacterial activity, the compounds of Formula (A) show little direct activity.

The following data demonstrate the potentiation effect or synergistic activity of compounds of the invention, as illustrated by the compound of Example 1, when used in combination with various beta-lactam antibiotics. Since the compound of Example 1 does not exhibit much direct antibiotic activity (see Table 1), synergy or potentiation is defined herein as a four-fold or greater reduction in the MIC of the beta-lactam antibiotic caused by the presence of the compound of formula (A), compared to the beta-lactam antibiotic alone. Preferably, combinations of the invention exhibit at least an 8-fold reduction in MIC when compared to the beta-lactam antibiotic alone.

Potentiation of Activity (MIC in μg/mL) of Aztreonam by Beta-Lactamase Inhibitors in Isogenic Strains of E. coli Expressing Individual Beta-Lactamases.

| AZTREONAM (AZ) | E. coli (KPC-2) | E. coli (TEM-10) | E. coli (SHV-12) | E. coli (CTX-M-15) | E. coli (AmpC) | E. coli (OXA-18) |
|---|---|---|---|---|---|---|
| AZ alone | 64 | 64 | >64 | 64 | 4 | >64 |
| AZ + Ex. 1 (2 μg/mL) | 0.125 | 0.125 | 0.25 | ≤0.06 | 0.125 | 1 |
| AZ + Avibactam (2 μg/mL) | 0.125 | 0.25 | 1 | 0.125 | ≤0.06 | 1 |
| AZ + Relebactam (2 μg/mL) | 1 | 2 | 32 | 0.5 | 0.125 | >64 |

Potentiation of Activity (MIC in μg/mL) of Ceftazidime by Beta-Lactamase Inhibitors in Isogenic Strains of E. coli Expressing Individual Beta-Lactamases.

| CEFTAZIDIME (Ceft) | E. coli (KPC-2) | E. coli (TEM-10) | E. coli (SHV-12) | E. coli (CTX-M-15) | E. coli (AmpC) | E. coli (OXA-18) |
|---|---|---|---|---|---|---|
| Ceftazidime Alone | 4 | >64 | >64 | 16 | 4 | >64 |
| Ceft + Ex. 1 (2 μg/mL) | 0.125 | 0.25 | 0.25 | 0.25 | 0.25 | 0.5 |
| Ceft + Avibactam (2 μg/mL) | 0.25 | 1 | 0.5 | 0.25 | 0.125 | 0.5 |
| Ceft + Relebactam (2 μg/mL) | 0.25 | 8 | 8 | 0.5 | 0.125 | >64 |

Potentiation of Activity (MIC in μg/mL) of Meropenem by Beta-Lactamase Inhibitors Isogenic Strains of E. coli Expressing Individual Beta-Lactamases.

| MEROPENEM (Mero) | E. coli (KPC-2) | E. coli (TEM-10) | E. coli (SHV-12) | E. coli (CTX-M-15) | E. coli (AmpC) | E. coli (OXA-18) |
|---|---|---|---|---|---|---|
| Mero alone | 1 | ≤0.06 | ≤0.06 | ≤0.06 | ≤0.06 | ≤0.06 |
| Mero + Ex. 1 (2 μg/mL) | ≤0.06 | ≤0.06 | ≤0.06 | ≤0.06 | ≤0.06 | ≤0.06 |
| Mero + Avibactam (2 μg/mL) | ≤0.06 | ≤0.06 | ≤0.06 | ≤0.06 | ≤0.06 | ≤0.06 |
| Mero + Relebactam (2 μg/mL) | ≤0.06 | ≤0.06 | ≤0.06 | ≤0.06 | ≤0.06 | ≤0.06 |

Potentiation of Activity (MIC in μg/mL) of Piperacillin by Beta-Lactamase Inhibitors in Isogenic Strains of E. coli Expressing Individual Beta-Lactamases.

| Piperacillin (Pip) | E. coli (KPC-2) | E. coli (TEM-10) | E. coli (SHV-12) | E. coli (CTX-M-15) | E. coli (AmpC) | E. coli (OXA-18) |
|---|---|---|---|---|---|---|
| Pip Alone | >32 | >32 | >32 | >32 | >32 | >32 |
| Pip + Tazobactam (4 μg/mL) | >32 | 4 | 32 | 4 | 8 | 8 |
| Pip + Avibactam (2 μg/mL) | 4 | 2 | 4 | 4 | 4 | 2 |
| Pip + Relebactam (2 μg/mL) | 4 | >32 | >32 | 16 | 4 | >32 |
| Pip + Ex. 1 (2 μg/mL) | 4 | 2 | 2 | 2 | 8 | 2 |
| Pip + Ex. 2 (2 μg/mL) | 2 | 4 | 4 | 4 | 8 | 4 |
| Pip + Ex. 3 (2 μg/mL) | 2 | 4 | 2 | 4 | 8 | 4 |
| Pip + Ex. 4 (4 μg/mL) | 2 | 4 | 4 | 2 | 4 | ND |
| Pip + Ex. 5 (4 μg/mL) | 1 | 2 | 2 | 2 | 16 | ND |
| Pip + Ex. 6 (4 μg/mL) | 2 | 4 | 4 | 4 | 4 | ND |
| Pip + Ex. 7 (2 μg/mL) | 2 | 2 | 4 | 4 | 8 | 8 |
| Pip + Ex. 8 (4 μg/mL) | 4 | 4 | 4 | 2 | 4 | ND |

Potentiation of Activity (μg/mL) of Beta-Lactam 5 by Beta-Lactamase Inhibitors in Isogenic Strains of E. coli Expressing Individual Beta-Lactamases.

| Beta-Lactam 5 (5) | E. coli (KPC-2) | E. coli (TEM-10) | E. coli (SHV-12) | E. coli (CTX-M-15) | E. coli (AmpC) | E. coli (OXA-18) |
|---|---|---|---|---|---|---|
| Beta-Lactam 5 Alone | 0.25 | 2 | 0.5 | 0.125 | 0.25 | 0.5 |
| 5 + Ex. 1 (2 μg/mL) | 0.25 | 0.125 | 0.25 | 0.25 | 0.25 | 0.25 |
| 5 + Avibactam (2 μg/mL) | 0.125 | 0.125 | 0.125 | 0.25 | 0.125 | 0.125 |
| 5 + Relebactam (2 μg/mL) | 0.125 | 0.25 | 0.125 | 0.25 | 0.25 | 0.25 |

Potentiation of Activity (μg/mL) of Aztreonam by Beta-Lactamase Inhibitors in Beta-Lactam Resistant Clinical Isolates.

| AZTREONAM | K. pneumoniae NB29323 (CTX-M-15, OXA-48, VEB-1) | Enterobacter cloacae NB25044 (CTX-M-12, ACT, KPC-2) |
|---|---|---|
| Aztreonam Alone | >64 | >64 |
| AZ + Ex. 1 (2 μg/mL) | 0.25 | 4 |
| AZ + Avibactam (2 μg/mL) | 2 | 8 |
| AZ + Relebactam (2 μg/mL) | 8 | >64 |

Potentiation of Activity (μg/mL) of Piperacillin by Beta-Lactamase-Inhibitors in Beta-Lactam Resistant Clinical Isolates.

| PIPERACILLIN | K. pneumoniae NB29082 (KPC-2) | Enterobacter cloacae NB25055 (CMY-2) | S. aureus NB01437 (BLA+) |
|---|---|---|---|
| Piperacillin | >64 | >64 | 64 |
| Pip + Tazobactam (4 μg/mL) | >64 | 64 | 1 |
| Pip + Ex. 1 (2 μg/mL) | 8 | 4 | 1 |

This data demonstrates that potentiation by the compounds of the invention is similar to or superior to that of some beta-lactamase inhibitors used in the clinic when it is used in combination with commercial beta-lactam antibiotics to treat infections caused by bacteria that are resistant to some known beta-lactam antibiotics.

Those skilled in the art will recognize, or be able to ascertain using no more than routine experimentation, many equivalents to the specific embodiments and methods described herein. Such equivalents are intended to be encompassed by the scope of the following claims.

The invention claimed is:

1. A compound of Formula (A):

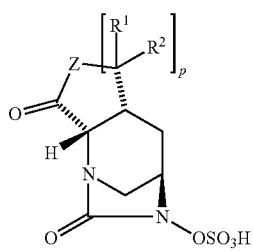

wherein p is 1 or 2;

R¹ and R² are independently selected from H and $C_1$-$C_4$ alkyl optionally substituted with up to three groups selected from halo, CN, —OR, oxo, and —NRR';

Z is $NR^3$ or N—$OR^3$;

$R^3$ is independently selected at each occurrence from H, Cy, and $C_1$-$C_4$ alkyl optionally substituted with up to three groups selected from Cy, halo, CN, —OR, and —NRR';

Cy is a $C_3$-$C_6$ cycloalkyl ring or 4-6 membered heterocyclic ring containing one or two heteroatoms selected from N, O and S as ring members, and Cy is optionally substituted with up to three groups selected from oxo, halo, $C_1$-$C_2$ alkyl, CN, —OR, and —NRR'; and R and R' are independently selected from H and $C_1$-$C_4$ alkyl optionally substituted with one or two groups selected from halo, —OH, —CN, —O—($C_1$-$C_4$ alkyl), oxo, —$NH_2$, —NH($C_1$-$C_4$ alkyl), and —N($C_1$-$C_4$ alkyl)$_2$, or R and R' taken together with the nitrogen atom to which both are attached can form a ring selected from piperidine, morpholine, pyrrolidine, and azetidine, wherein the ring is optionally substituted with one or two groups selected from halo, $C_1$-$C_2$ alkyl, —OH, —CN, —O—($C_1$-$C_4$ alkyl), oxo, —$NH_2$, —NH($C_1$-$C_4$ alkyl), and —N($C_1$-$C_4$ alkyl)$_2$;

or a salt or zwitterionic form thereof.

2. The compound of claim 1, which a compound of one of the following formulas:

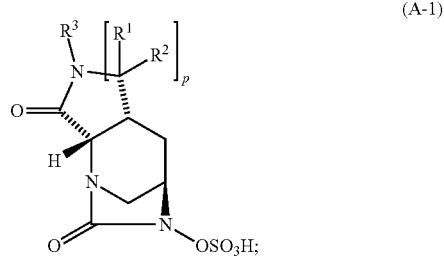

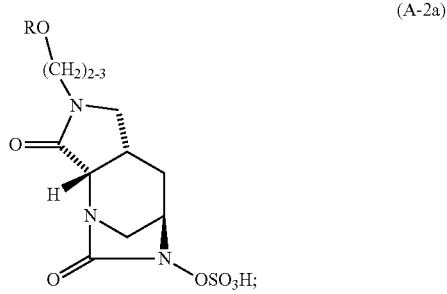

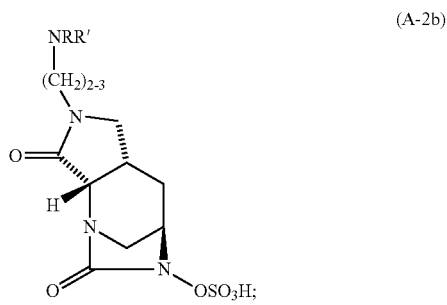

or a salt or zwitterionic form thereof.

3. The compound of claim 1, which is a compound of Formula (I):

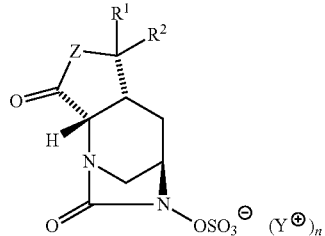

(I)

wherein:

R¹ and R² are independently selected from H and $C_1$-$C_4$ alkyl optionally substituted with up to three groups selected from halo, CN, —OR, oxo, and —NRR';

Z is $NR^3$ or N—$OR^3$;

$R^3$ is independently selected at each occurrence from H, Cy, and $C_1$-$C_4$ alkyl optionally substituted with up to three groups selected from Cy, halo, CN, —OR, and —NRR';

Cy is a $C_3$-$C_6$ cycloalkyl ring, or 4-6 membered heterocyclic ring containing one or two heteroatoms selected from N, O and S as ring members, and Cy is optionally substituted with up to three groups selected from oxo, halo, $C_1$-$C_2$ alkyl, CN, —OR, and —NRR'; and R and R' are independently selected from H and $C_1$-$C_4$ alkyl optionally substituted with one or two groups selected from halo, —OH, —CN, —O—($C_1$-$C_4$ alkyl), oxo, —$NH_2$, —NH($C_1$-$C_4$ alkyl), and —N($C_1$-$C_4$ alkyl)$_2$, or R and R' taken together with the nitrogen atom to which both are attached can form a ring selected from piperidine, morpholine, pyrrolidine, and azetidine, wherein the ring is optionally substituted with one or two groups selected from halo, $C_1$-$C_2$ alkyl, —OH, —CN, —O—($C_1$-$C_4$ alkyl), oxo, —$NH_2$, —NH($C_1$-$C_4$ alkyl), and —N($C_1$-$C_4$ alkyl)$_2$;

Y is a cationic group;

n is 0 or 1; and when n is 0 the compound of Formula I is in a zwitterionic form.

4. The compound of claim 1, wherein Z is $NR^3$, and $R^3$ is H or $C_1$-$C_4$ alkyl optionally substituted with —OR or —NRR', or a salt or zwitterionic form thereof.

5. The compound of claim 4, wherein $R^3$ is $C_1$-$C_2$ alkyl optionally substituted with —OR or —NRR', or a salt or zwitterionic form thereof.

6. The compound of claim 4, wherein $R^3$ is H, or a salt or zwitterionic form thereof.

7. The compound of claim 1, wherein R¹ and R² are both H, or a salt or zwitterionic form thereof.

8. The compound of claim 1, which has the structure:

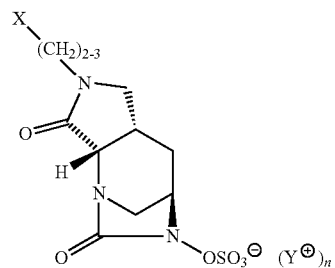

(II)

wherein X is —OR or —NRR';
as a salt or zwitterionic form thereof.

9. The compound of claim 1, which is selected from:

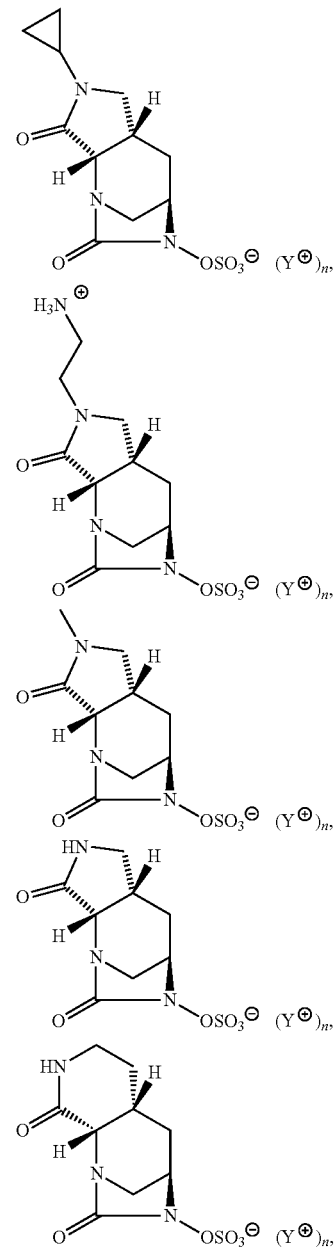

-continued

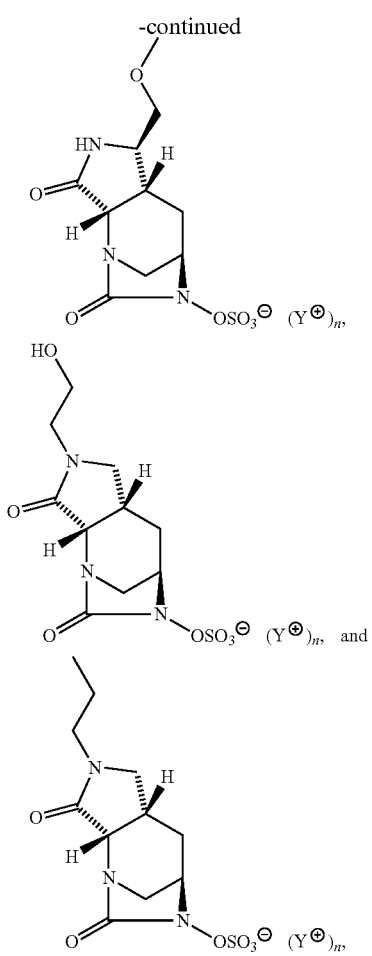

and the salt or zwitterionic forms thereof.

10. A compound of Formula (VI):

(VI)

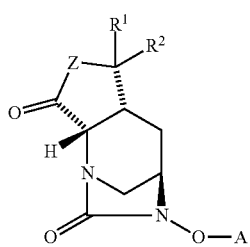

wherein:
R¹ and R² are independently selected from H and $C_1$-$C_4$ alkyl optionally substituted with up to three groups selected from halo, CN, —OR, oxo, and —NRR';
Z is $NR^3$ or N—$OR^3$;
$R^3$ is independently selected at each occurrence from H, Cy, and $C_1$-$C_4$ alkyl optionally substituted with up to three groups selected from Cy, halo, CN, —OR, and —NRR';
Cy is a $C_3$-$C_6$ cycloalkyl ring or 4-6 membered heterocyclic ring containing one or two heteroatoms selected from N, O and S as ring members, and Cy is optionally substituted with up to three groups selected from oxo, halo, $C_1$-$C_2$ alkyl, CN, —OR, and —NRR'; and R and R' are independently selected from H and $C_1$-$C_4$ alkyl optionally substituted with one or two groups selected from halo, $C_1$-$C_2$ alkyl, —OH, —CN, —O—($C_1$-$C_4$ alkyl), oxo, —$NH_2$, —NH($C_1$-$C_4$ alkyl), and —N($C_1$-$C_4$ alkyl)$_2$,
or R and R' taken together with the nitrogen atom to which both are attached can form a ring selected from piperidine, morpholine, pyrrolidine, and azetidine, wherein the ring is optionally substituted with one or two groups selected from halo, $C_1$-$C_2$ alkyl, —OH, —CN, —O—($C_1$-$C_4$ alkyl), oxo, —$NH_2$, —NH($C_1$-$C_4$ alkyl), and —N($C_1$-$C_4$ alkyl)$_2$;
A is H or —$CH_2$-Ph, where Ph represents phenyl optionally substituted with one or two groups selected from halo, $C_1$-$C_4$ alkyl, $C_1$-$C_4$ alkoxy;
or a salt thereof.

11. The compound of claim 1 having the formula (VII):

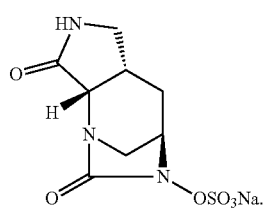

12. The compound of claim 11 in crystalline form.
13. The compound of claim 12, which exhibits an endotherm on differential scanning calorimetry between 283° C. and 350° C.
14. The compound of claim 12, characterized by XRPD peaks at diffraction angles (2Theta) of 8.3 and 16.6 degrees.
15. A process to make a compound of Formula (I), (I)

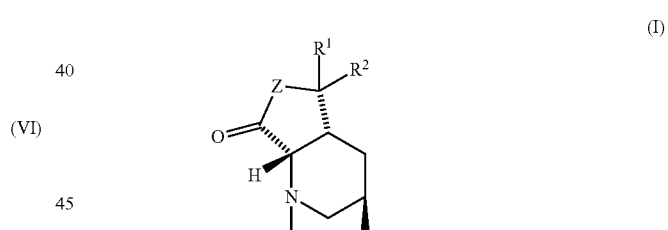

according to claim 3;
wherein the process comprises contacting a compound of Formula (III)

(III)

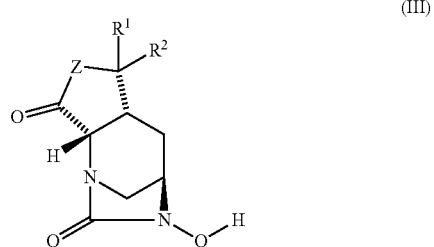

wherein Z, R¹ and R² and R³ are as defined in claim 3, with a sulfonylating agent in the presence of a base.

16. A pharmaceutical composition comprising a compound of claim 1 and at least one pharmaceutically acceptable excipient.

17. A pharmaceutical combination, comprising a compound according to claim 1 and a beta-lactam antibiotic.

18. A method to treat a subject having a Gram-negative bacterial infection, which comprises administering to the subject an effective amount of a beta-lactam antibiotic and a compound of Formula (A) according to claim 1.

* * * * *

SEQUENCE LISTING

<160> NUMBER OF SEQ ID NOS: 41

<210> SEQ ID NO 1
<211> LENGTH: 32
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 1
tcgcctcgag gcgactgcgc tgacgaattt gg                                 32

<210> SEQ ID NO 2
<211> LENGTH: 33
<212> TYPE: DNA
<213> ORGANISM: artificial sequence
<220> FEATURE:
<223> OTHER INFORMATION: /note="Description of Artificial Sequence:
      Synthetic polynucleotide"

<400> SEQUENCE: 2
aatcgaattc ttactgacca ttaacgccca agc                                33

<210> SEQ ID NO 3
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 3
tcgcctcgag gcgagcccgc aaccgctgga                                    30

<210> SEQ ID NO 4
<211> LENGTH: 32
<212> TYPE: DNA
<213> ORGANISM: Artificial Sequence
<220> FEATURE:

<223> OTHER INFORMATION: /note="Description of Artificial Sequence:
Synthetic polynucleotide"

<400> SEQUENCE: 4
aatcgaattc ttaacgctgc cagtgctcaa tc                                    32

<210> SEQ ID NO 5
<211> LENGTH: 34
<212> TYPE: DNA
<213> ORGANISM: Artificial Sequence
<220> FEATURE:
<223> OTHER INFORMATION: /note="Description of Artificial Sequence:
Synthetic polynucleotide"

<400> SEQUENCE: 5
cgctctcgag agcgtcccgc tgtacgcaca aacg                                  34

<210> SEQ ID NO 6
<211> LENGTH: 32
<212> TYPE: DNA
<213> ORGANISM: Artificial Sequence
<220> FEATURE:
<223> OTHER INFORMATION: /note="Description of Artificial Sequence:
Synthetic polynucleotide"

<400> SEQUENCE: 6
aatcgaattc ttacagaccg tcggtgacaa tc                                    32

<210> SEQ ID NO 7
<211> LENGTH: 884
<212> TYPE: DNA
<213> ORGANISM: Artificial Sequence
<220> FEATURE:
<223> OTHER INFORMATION: /note="Description of Artificial Sequence:
Synthetic polynucleotide"

<400> SEQUENCE: 7
atgggccatc atcatcatca tcacagcagc ggcctggaag ttctgttcca ggggcccgcg      60
actgcgctga cgaatttggt ggccgagccg ttcgcgaaat tggagcaaga ttttggtggt     120
tcgatcggtg tctacgcgat ggacaccggt agcggtgcca ccgtgagcta ccgtgccgaa     180
gagcgttttc cgctgtgtag ctctttcaag ggttttctgg ccgcagccgt gctggcacgc     240
agccaacagc aagcgggcct gctggacacc ccgatccgtt acggcaaaaa tgcgctggtt     300
ccgtggagcc cgattagcga aaagtacctg accaccggca tgacggtggc ggagttgagc     360
gctgcggcgg ttcagtattc cgataacgct cggcaaatc tgctgctgaa agaactgggc      420
ggtccagcgg gtctgacggc tttcatgcgt tctattggcg acaccacctt tcgcttggac     480
cgctgggagc tggagctgaa cagcgcgatt ccgggcgacg cacgtgatac gagcagcccg     540
cgtgcagtga ccgagagcct gcagaagctg accctgggca gcgcactggc cgcaccgcag     600
cgccaacagt tcgtcgattg gctgaaggga acaccaccg gtaaccatcg tattcgcgca      660
gcggtcccgg ctgattgggc agttggtgac aagactggta cgtgcggcgt ttatggtacg     720
gcgaatgact acgcggttgt ttggcctacg ggtcgtgcgc cgatcgtcct ggcggtgtat     780
acccgtgctc cgaacaaaga cgataaacac tccgaagcgg tcatcgccgc agcagcgcgt     840
ctggccctgg aaggcttggg cgttaatggt cagtaacgcc ggcg                      884

<210> SEQ ID NO 8
<211> LENGTH: 32
<212> TYPE: DNA
<213> ORGANISM: Artificial Sequence
<220> FEATURE:
<223> OTHER INFORMATION: /note="Description of Artificial Sequence:
    Synthetic polynucleotide"

<400> SEQUENCE: 8
tcgcctcgag gcgactgcgc tgacgaattt gg            32

<210> SEQ ID NO 9
<211> LENGTH: 33
<212> TYPE: DNA
<213> ORGANISM: Artificial Sequence
<220> FEATURE:
<223> OTHER INFORMATION: /note="Description of Artificial Sequence:
    Synthetic polynucleotide"

<400> SEQUENCE: 9
aatcgaattc ttactgacca ttaacgccca agc           33

<210> SEQ ID NO 10
<211> LENGTH: 33
<212> TYPE: DNA
<213> ORGANISM: Artificial Sequence
<220> FEATURE:
<223> OTHER INFORMATION: /note="Description of Artificial Sequence:
    Synthetic polynucleotide"

<400> SEQUENCE: 10
gcttgggcgt taatggtcag taagaattcg att           33

<210> SEQ ID NO 11
<211> LENGTH: 866
<212> TYPE: DNA
<213> ORGANISM: Artificial Sequence
<220> FEATURE:
<223> OTHER INFORMATION: /note="Description of Artificial Sequence:
    Synthetic polynucleotide"

<400> SEQUENCE: 11
atgggccatc atcatcatca tcacagcagc ggcctggaag ttctgttcca ggggcccgcg    60
agcccgcaac cgctggagca gatcaagcag tctgagagcc agctgagcgg ccgtgtgggt   120
atgatcgaga tggatctggc ttccggccgt acgctgacgg catggcgtgc cgacgaacgt   180
ttcccgatga tgtcgacctt taaagttgtt ctgtgtggtg cggtcttggc acgtgtagac   240
gcgggtgacg aacaactgga gcgcaagatc cattaccgcc aacaggactt ggtcgactac   300
agcccggtta gcgaaaagca cctggcggat ggcatgaccg tgggtgaatt gtgcgccgct   360
gcgattacca tgagcgacaa tagcgcggct aatctgctgt ggcgaccgt tggtggccca    420 gcgggcttga ccgcatttct gcgtcaaatc ggcgataatg ttacgcgtct ggatcgctgg   480
gaaacggagc tgaacgaggc actgccgggt gatgcccgtg ataccacgac tcctgctagc   540
atggcagcga ccctgcgtaa actgctgacc agccagcgtc tgagcgcacg tagccaacgc   600
cagctgctgc aatggatggt ggatgaccgc gtggcgggtc cgctgatccg ctccgtcctg   660
ccagcaggct ggttcattgc ggacaaaact ggtgcctcta agcgtggtgc gcgtggtatc   720
gtcgcgctgc tgggtccgaa caacaaagcc gaacgtattg tggttatcta tctgcgcgac   780 acccggcaa gcatggccga gcgcaaccag caaattgcgg gcattggtgc ggcactgatt   840
gagcactggc agcgttaacg ccggcg                                        866

<210> SEQ ID NO 12
<211> LENGTH: 30
<212> TYPE: DNA

```
<213> ORGANISM: Artificial Sequence
<220> FEATURE:
<223> OTHER INFORMATION: /note="Description of Artificial Sequence:
      Synthetic polynucleotide"

<400> SEQUENCE: 12
tcgcctcgag gcgagcccgc aaccgctgga                                    30

<210> SEQ ID NO 13
<211> LENGTH: 32
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 13
aatcgaattc ttaacgctgc cagtgctcaa tc                                 32

<210> SEQ ID NO 14
<211> LENGTH: 32
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 14
gattgagcac tggcagcgtt aagaattcga tt                                 32

<210> SEQ ID NO 15
<211> LENGTH: 34
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 15
cgctctcgag agcgtcccgc tgtacgcaca aacg                               34

<210> SEQ ID NO 16
<211> LENGTH: 32
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 16
aatcgaattc ttacagaccg tcggtgacaa tc                                 32

<210> SEQ ID NO 17
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 17
gccctcgagg gcgaggcccc ggcggatcgc                                    30

<210> SEQ ID NO 18
<211> LENGTH: 29
<212> TYPE: DNA
<213> ORGANISM: Artificial Sequence
```

```
<220> FEATURE:
<223> OTHER INFORMATION: /note="Description of Artificial Sequence:
      Synthetic polynucleotide"

<400> SEQUENCE: 18
tgagaattct cagcgcttca gcggcacct                                        29

<210> SEQ ID NO 19
<211> LENGTH: 31
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 19
ttcactgcag tgaacgttgc gaagcaacgg c                                     31

<210> SEQ ID NO 20
<211> LENGTH: 41
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 20
tcgaggatcc tcgagagcaa aaacaggaag gcaaaatgcc g                          41

<210> SEQ ID NO 21
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 21
ccgtctagac ggatggcctt tttgcgtttc                                       30

<210> SEQ ID NO 22
<211> LENGTH: 33
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 22
aatcgaattc ttactgacca ttaacgccca agc                                   33

<210> SEQ ID NO 23
<211> LENGTH: 32
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 23
aatcgaattc ttaacgctgc cagtgctcaa tc                                    32

<210> SEQ ID NO 24
<211> LENGTH: 32
<212> TYPE: DNA
<213> ORGANISM: Artificial Sequence
<220> FEATURE:
```

```
<223> OTHER INFORMATION: /note="Description of Artificial Sequence:
      Synthetic polynucleotide"

<400> SEQUENCE: 24
aatcgaattc ttacagaccg tcggtgacaa tc                                 32

<210> SEQ ID NO 25
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 25
gaattcgcta gcccaaaaaa acgg                                          24

<210> SEQ ID NO 26
<211> LENGTH: 29
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 26
cgtcttgctc caggccgcga ttaaattcc                                     29

<210> SEQ ID NO 27
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 27
tcgcggcctg gagcaagacg tttc                                          24

<210> SEQ ID NO 28
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 28
tcacgtagcg atagcggag                                                19

<210> SEQ ID NO 29
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 29
cgcgagaccc acgcttaccg gctccaga                                      28

<210> SEQ ID NO 30
<211> LENGTH: 25
<212> TYPE: DNA
<213> ORGANISM: Artificial Sequence
<220> FEATURE:
<223> OTHER INFORMATION: /note="Description of Artificial Sequence:
```

Synthetic polynucleotide"

<400> SEQUENCE: 30
ctcgccttga tagttgggaa ccgga    25

<210> SEQ ID NO 31
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 31
cggttcccaa ctatcaaggc gagt    24

<210> SEQ ID NO 32
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 32
gacattgccg tcactgcgtc t    21

<210> SEQ ID NO 33
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 33
tcacgtagcg atagcggag    19

<210> SEQ ID NO 34
<211> LENGTH: 41
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 34
gtaactcgcc ttgatagttg ggaaccggag ctgaatgaag c    41

<210> SEQ ID NO 35
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 35
gcgggaccaa agccatgaca    20

<210> SEQ ID NO 36
<211> LENGTH: 47
<212> TYPE: DNA
<213> ORGANISM: Artificial Sequence
<220> FEATURE:
<223> OTHER INFORMATION: /note="Description of Artificial Sequence:
      Synthetic polynucleotide"

```
<400> SEQUENCE: 36
accgcgagac ccacgcttac cggctccaga tttatcagca ataaacc                      47

<210> SEQ ID NO 37
<211> LENGTH: 34
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 37
gtaagaattc ttaccaatgc ttaatcagtg aggc                                    34

<210> SEQ ID NO 38
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 38
ccgtctagac ggatggcctt tttgcgtttc                                         30

<210> SEQ ID NO 39
<211> LENGTH: 875
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 39
atgggccatc atcatcatca tcacagcagc ggcctggaag ttctgttcca ggggcccagc        60
gtcccgctgt acgcacaaac ggccgacgtg caacagaaac tggcggagtt ggaacgtcag       120
agcggtggcc gtttgggtgt agccctgatc aataccgcgg acaatagcca aattctgtat       180
cgtgcggacg aacgcttcgc gatgtgcagc acgagcaagg tgatggccgc tgcggccgtt       240
ctgaagaaat ccgagagcga gccgaacttg ctgaatcagc gcgttgagat caagaagtcg       300
gatctggtga actataaccc tatcgcggaa aaacatgtca acggcaccat gtccctggca       360
gagctgagcg cggctgcgtt gcagtactct gataacgtcg caatgaataa actgatcgca       420
cacgtcggtg cccagcaag cgtgaccgcc tttgcgcgtc aactgggcga tgaaactttt        480
cgtctggatc gtaccgaacc gaccctgaat acggcaattc cgggtgatcc gcgcgacacg       540
acgagcccgc gtgcaatggc acagaccctg cgcaacctga ccctgggtaa agcgctgggc       600
gatagccaac gtgcgcagct ggttacgtgg atgaagggta acaccaccgg tgcggccagc       660
attcaagcgg gcctgccggc cagctgggtt gttggtgata aaactggctc cggtggttat       720
ggtaccacga atgacatcgc ggttatttgg ccgaaggacc gtgcgccgtt gatcctggtg       780
acctacttca cccagccgca gccgaaagct gagtctcgcc gtgacgtgct ggcgagcgca       840
gctaagattg tcaccgacgg tctgtaacgc cggcg                                 875

<210> SEQ ID NO 40
<211> LENGTH: 24
<212> TYPE: DNA
<213> ORGANISM: Artificial Sequence
<220> FEATURE:
<223> OTHER INFORMATION: /note="Description of Artificial Sequence:
```

```
            Synthetic polynucleotide"

<400> SEQUENCE: 40
tgccttcctg tttttgctct cgag                                          24

<210> SEQ ID NO 41
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 41
tggagccggt aagcgtgggt ctcgcggt                                      28
```